(12) United States Patent
Boock et al.

(10) Patent No.: US 9,693,721 B2
(45) Date of Patent: *Jul. 4, 2017

(54) POLYMER MEMBRANES FOR CONTINUOUS ANALYTE SENSORS

(71) Applicant: DexCom, Inc., San Diego, CA (US)

(72) Inventors: Robert J. Boock, Carlsbad, CA (US); Monica A. Rixman, Medford, MA (US); Huashi Zhang, San Diego, CA (US); Michael J. Estes, Poway, CA (US); Kristina Lawrence, Escondido, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/742,137

(22) Filed: Jun. 17, 2015

(65) Prior Publication Data
US 2015/0282750 A1 Oct. 8, 2015

Related U.S. Application Data

(63) Continuation of application No. 14/517,663, filed on Oct. 17, 2014, now Pat. No. 9,566,026, which is a
(Continued)

(51) Int. Cl.
*A61B 5/1486* (2006.01)
*A61B 5/1468* (2006.01)
(Continued)

(52) U.S. Cl.
CPC ........ *A61B 5/14865* (2013.01); *A61B 5/1468* (2013.01); *A61B 5/1473* (2013.01);
(Continued)

(58) Field of Classification Search
CPC . A61B 5/145; A61B 5/14503; A61B 5/14532; A61B 5/14546; A61B 5/1468;
(Continued)

(56) References Cited

U.S. PATENT DOCUMENTS 2,830,020 A 4/1958 Christmann et al.
3,220,960 A 11/1965 Lim et al.
(Continued)

FOREIGN PATENT DOCUMENTS

EP 0 098 592 1/1984
EP 0 127 958 12/1984
(Continued)

OTHER PUBLICATIONS

US 7,530,950, 05/2009, Brister et al. (withdrawn)
(Continued)

*Primary Examiner* — Navin Natnithithadha
(74) *Attorney, Agent, or Firm* — Knobbe Martens Olson & Bear, LLP

(57) ABSTRACT

Devices and methods are described for providing continuous measurement of an analyte concentration. In some embodiments, the device has a sensing mechanism and a sensing membrane that includes at least one surface-active group-containing polymer and that is located over the sensing mechanism. The sensing membrane may have a bioprotective layer configured to substantially block the effect and/or influence of non-constant noise-causing species.

19 Claims, 13 Drawing Sheets

Related U.S. Application Data continuation of application No. 14/058,154, filed on Oct. 18, 2013, now Pat. No. 8,954,128, which is a continuation of application No. 12/718,299, filed on Mar. 5, 2010, now Pat. No. 8,583,204, which is a continuation-in-part of application No. 12/413,231, filed on Mar. 27, 2009, now abandoned.

(60) Provisional application No. 61/040,594, filed on Mar. 28, 2008.

(51) Int. Cl.
```
G01N 27/40      (2006.01)
A61B 5/1473     (2006.01)
A61B 5/145      (2006.01)
C12Q 1/00       (2006.01)
A61B 5/00       (2006.01)
```

(52) U.S. Cl.
CPC ........ *A61B 5/1486* (2013.01); *A61B 5/14532* (2013.01); *A61B 5/14546* (2013.01); *C12Q 1/006* (2013.01); *G01N 27/40* (2013.01); *A61B 5/7203* (2013.01)

(58) Field of Classification Search
CPC .............. A61B 5/14685; A61B 5/1473; A61B 5/14735; A61B 5/1486; A61B 5/14865; A61B 5/1495; A61B 5/7203; C12Q 1/006; G01N 27/40
USPC ........................................ 600/309, 345–366
See application file for complete search history.

(56) References Cited

U.S. PATENT DOCUMENTS

| | | |
|---|---|---|
| 3,562,352 A | 2/1971 | Nyilas |
| 3,607,329 A | 9/1971 | Manjikian |
| 3,746,588 A | 7/1973 | Brown, Jr. |
| 3,837,339 A | 9/1974 | Aisenberg |
| 3,898,984 A | 8/1975 | Mandel et al. |
| 3,943,918 A | 3/1976 | Lewis |
| 4,040,908 A | 8/1977 | Clark, Jr. |
| 4,136,250 A | 1/1979 | Mueller et al. |
| 4,253,469 A | 3/1981 | Aslan |
| 4,256,561 A | 3/1981 | Schindler et al. |
| 4,260,725 A | 4/1981 | Keogh et al. |
| 4,267,145 A | 5/1981 | Wysong |
| 4,292,423 A | 9/1981 | Kaufmann et al. |
| 4,403,984 A | 9/1983 | Ash et al. |
| 4,415,666 A | 11/1983 | D'Orazio et al. |
| 4,418,148 A | 11/1983 | Oberhardt |
| 4,442,841 A | 4/1984 | Uehara et al. |
| 4,454,295 A | 6/1984 | Wittmann et al. |
| 4,482,666 A | 11/1984 | Reeves |
| 4,484,987 A | 11/1984 | Gough |
| 4,493,714 A | 1/1985 | Ueda et al. |
| 4,494,950 A | 1/1985 | Fischell |
| 4,527,999 A | 7/1985 | Lee |
| 4,545,382 A | 10/1985 | Higgins et al. |
| 4,554,927 A | 11/1985 | Fussell |
| 4,568,444 A | 2/1986 | Nakamura et al. |
| 4,589,873 A | 5/1986 | Schwartz et al. |
| 4,602,922 A | 7/1986 | Cabasso et al. |
| 4,632,968 A | 12/1986 | Yokota et al. |
| 4,644,046 A | 2/1987 | Yamada |
| 4,647,643 A | 3/1987 | Zdrabala et al. |
| 4,650,547 A | 3/1987 | Gough |
| 4,671,288 A | 6/1987 | Gough |
| 4,672,970 A | 6/1987 | Uchida et al. |
| 4,680,268 A | 7/1987 | Clark, Jr. |
| 4,684,538 A | 8/1987 | Klemarczyk |
| 4,685,463 A | 8/1987 | Williams |
| 4,686,137 A | 8/1987 | Ward, Jr. et al. |
| 4,689,149 A | 8/1987 | Kanno et al. |
| 4,689,309 A | 8/1987 | Jones |
| 4,703,756 A | 11/1987 | Gough et al. |
| 4,711,245 A | 12/1987 | Higgins |
| 4,721,677 A | 1/1988 | Clark |
| 4,726,381 A | 2/1988 | Jones |
| 4,731,726 A | 3/1988 | Allen |
| 4,739,380 A | 4/1988 | Lauks et al. |
| 4,757,022 A | 7/1988 | Shults et al. |
| 4,763,658 A | 8/1988 | Jones |
| 4,781,733 A | 11/1988 | Babcock et al. |
| 4,786,657 A | 11/1988 | Hammar et al. |
| 4,793,555 A | 12/1988 | Lee et al. |
| 4,795,542 A | 1/1989 | Ross et al. |
| 4,805,625 A | 2/1989 | Wyler |
| 4,813,424 A | 3/1989 | Wilkins |
| 4,822,336 A | 4/1989 | DiTraglia |
| 4,832,034 A | 5/1989 | Pizziconi |
| 4,852,573 A | 8/1989 | Kennedy |
| 4,861,830 A | 8/1989 | Ward, Jr. |
| 4,871,440 A | 10/1989 | Nagata et al. |
| 4,880,883 A | 11/1989 | Grasel et al. |
| 4,886,740 A | 12/1989 | Vadgama |
| 4,890,620 A | 1/1990 | Gough |
| 4,908,208 A | 3/1990 | Lee et al. |
| 4,909,908 A | 3/1990 | Ross et al. |
| 4,919,141 A | 4/1990 | Zier et al. |
| 4,938,860 A | 7/1990 | Wogoman |
| 4,951,657 A | 8/1990 | Pfister et al. |
| 4,952,618 A | 8/1990 | Olsen |
| 4,953,552 A | 9/1990 | DeMarzo |
| 4,954,381 A | 9/1990 | Cabasso et al. |
| 4,960,594 A | 10/1990 | Honeycutt |
| 4,961,954 A | 10/1990 | Goldberg et al. |
| 4,963,595 A | 10/1990 | Ward et al. |
| 4,970,145 A | 11/1990 | Bennetto et al. |
| 4,973,320 A | 11/1990 | Brenner et al. |
| 4,988,341 A | 1/1991 | Columbus et al. |
| 4,994,167 A | 2/1991 | Shults et al. |
| 5,002,572 A | 3/1991 | Picha |
| 5,002,590 A | 3/1991 | Friesen et al. |
| 5,010,141 A | 4/1991 | Mueller |
| 5,034,461 A | 7/1991 | Lai et al. |
| 5,045,601 A | 9/1991 | Capelli et al. |
| 5,050,612 A | 9/1991 | Matsumura |
| 5,063,081 A | 11/1991 | Cozzette et al. |
| 5,067,491 A | 11/1991 | Taylor, II et al. |
| 5,070,169 A | 12/1991 | Robertson et al. |
| 5,071,452 A | 12/1991 | Avrillon et al. |
| 5,094,876 A | 3/1992 | Goldberg et al. |
| 5,100,689 A | 3/1992 | Goldberg et al. |
| 5,108,819 A | 4/1992 | Heller et al. |
| 5,115,056 A | 5/1992 | Mueller et al. |
| 5,120,813 A | 6/1992 | Ward, Jr. |
| 5,128,408 A | 7/1992 | Tanaka et al. |
| 5,135,297 A | 8/1992 | Valint et al. |
| 5,137,028 A | 8/1992 | Nishimura |
| 5,147,725 A | 9/1992 | Pinchuk |
| 5,155,149 A | 10/1992 | Atwater et al. |
| 5,160,418 A | 11/1992 | Mullen |
| 5,165,407 A | 11/1992 | Wilson et al. |
| 5,169,906 A | 12/1992 | Cray et al. |
| 5,171,689 A | 12/1992 | Kawaguri et al. |
| 5,183,549 A | 2/1993 | Joseph et al. |
| 5,200,051 A | 4/1993 | Cozzette et al. |
| 5,202,261 A | 4/1993 | Musho et al. |
| 5,208,313 A | 5/1993 | Krishnan |
| 5,212,050 A | 5/1993 | Mier et al. |
| 5,219,965 A | 6/1993 | Valint et al. |
| 5,221,724 A | 6/1993 | Li et al. |
| 5,235,003 A | 8/1993 | Ward et al. |
| 5,242,835 A | 9/1993 | Jensen |
| 5,249,576 A | 10/1993 | Goldberger et al. |
| 5,250,439 A | 10/1993 | Musho et al. |
| 5,264,104 A | 11/1993 | Gregg et al. |
| 5,269,891 A | 12/1993 | Colin |
| 5,284,140 A | 2/1994 | Allen et al. |
| 5,286,364 A | 2/1994 | Yacynych et al. |
| 5,290,548 A | 3/1994 | Goldberg et al. |
| 5,296,144 A | 3/1994 | Sternina et al. |

(56) References Cited

U.S. PATENT DOCUMENTS

| | | |
|---|---|---|
| 5,299,571 A | 4/1994 | Mastrototaro |
| 5,316,008 A | 5/1994 | Suga et al. |
| 5,322,063 A | 6/1994 | Allen et al. |
| 5,324,322 A | 6/1994 | Grill et al. |
| 5,326,356 A | 7/1994 | Della Valle et al. |
| 5,326,449 A | 7/1994 | Cunningham |
| 5,331,555 A | 7/1994 | Hashimoto et al. |
| 5,334,681 A | 8/1994 | Mueller et al. |
| 5,342,693 A | 8/1994 | Winters et al. |
| 5,352,348 A | 10/1994 | Young et al. |
| 5,372,133 A | 12/1994 | Hogen Esch |
| 5,376,400 A | 12/1994 | Goldberg et al. |
| 5,384,028 A | 1/1995 | Ito |
| 5,387,327 A | 2/1995 | Khan |
| 5,387,329 A | 2/1995 | Foos et al. |
| 5,390,671 A | 2/1995 | Lord et al. |
| 5,391,250 A | 2/1995 | Cheney, II et al. |
| 5,393,401 A | 2/1995 | Knoll |
| 5,397,451 A | 3/1995 | Senda et al. |
| 5,411,866 A | 5/1995 | Luong |
| 5,426,158 A | 6/1995 | Mueller et al. |
| 5,428,123 A | 6/1995 | Ward et al. |
| 5,429,735 A | 7/1995 | Johnson et al. |
| 5,438,984 A | 8/1995 | Schoendorfer |
| 5,443,508 A | 8/1995 | Giampapa |
| 5,453,248 A | 9/1995 | Olstein |
| 5,462,051 A | 10/1995 | Oka et al. |
| 5,466,575 A | 11/1995 | Cozzette et al. |
| 5,469,846 A | 11/1995 | Khan |
| 5,476,094 A | 12/1995 | Allen et al. |
| 5,494,562 A | 2/1996 | Maley et al. |
| 5,497,772 A | 3/1996 | Schulman et al. |
| 5,507,288 A | 4/1996 | Bocker et al. |
| 5,508,509 A | 4/1996 | Yafuso et al. |
| 5,512,055 A | 4/1996 | Domb et al. |
| 5,513,636 A | 5/1996 | Palti |
| 5,518,601 A | 5/1996 | Foos et al. |
| 5,521,273 A | 5/1996 | Yilgor et al. |
| 5,531,878 A | 7/1996 | Vadgama et al. |
| 5,541,305 A | 7/1996 | Yokota et al. |
| 5,545,220 A | 8/1996 | Andrews et al. |
| 5,549,651 A | 8/1996 | Lynn |
| 5,552,112 A | 9/1996 | Schiffmann |
| 5,554,339 A | 9/1996 | Cozzette |
| 5,564,439 A | 10/1996 | Picha |
| 5,568,806 A | 10/1996 | Cheney, II et al. |
| 5,569,186 A | 10/1996 | Lord et al. |
| 5,575,930 A | 11/1996 | Tietje-Girault et al. |
| 5,582,184 A | 12/1996 | Ericson et al. |
| 5,584,813 A | 12/1996 | Livingston et al. |
| 5,584,876 A | 12/1996 | Bruchman et al. |
| 5,586,553 A | 12/1996 | Halili et al. |
| 5,589,563 A | 12/1996 | Ward et al. |
| 5,593,852 A | 1/1997 | Heller et al. |
| 5,611,900 A | 3/1997 | Worden |
| 5,624,537 A | 4/1997 | Turner et al. |
| 5,637,135 A | 6/1997 | Ottenstein et al. |
| 5,640,954 A | 6/1997 | Pfeiffer |
| 5,658,247 A | 8/1997 | Henley |
| 5,665,222 A | 9/1997 | Heller et al. |
| 5,670,097 A | 9/1997 | Duan et al. |
| 5,681,572 A | 10/1997 | Seare |
| 5,683,562 A | 11/1997 | Schaffar et al. |
| 5,695,623 A | 12/1997 | Michel et al. |
| 5,700,559 A | 12/1997 | Sheu et al. |
| 5,703,359 A | 12/1997 | Wampler, III |
| 5,711,861 A | 1/1998 | Ward et al. |
| 5,741,330 A | 4/1998 | Brauker et al. |
| 5,743,262 A | 4/1998 | Lepper, Jr. et al. |
| 5,746,898 A | 5/1998 | Priedel |
| 5,756,632 A | 5/1998 | Ward et al. |
| 5,760,155 A | 6/1998 | Mowrer et al. |
| 5,766,839 A | 6/1998 | Johnson et al. |
| 5,773,286 A | 6/1998 | Dionne et al. |
| 5,776,324 A | 7/1998 | Usala |
| 5,777,060 A | 7/1998 | Van Antwerp |
| 5,786,439 A | 7/1998 | Van Antwerp et al. |
| 5,791,344 A | 8/1998 | Schulman et al. |
| 5,795,453 A | 8/1998 | Gilmartin |
| 5,800,420 A | 9/1998 | Gross |
| 5,804,048 A | 9/1998 | Wong et al. |
| 5,807,375 A | 9/1998 | Gross et al. |
| 5,807,636 A | 9/1998 | Sheu et al. |
| 5,820,570 A | 10/1998 | Erickson |
| 5,820,622 A | 10/1998 | Gross et al. |
| 5,833,603 A | 11/1998 | Kovacs et al. |
| 5,834,583 A | 11/1998 | Hancock et al. |
| 5,837,377 A | 11/1998 | Sheu et al. |
| 5,837,454 A | 11/1998 | Cozzette et al. |
| 5,837,661 A | 11/1998 | Evans et al. |
| 5,843,069 A | 12/1998 | Butler et al. |
| 5,863,627 A | 1/1999 | Szycher et al. |
| 5,863,972 A | 1/1999 | Beckelmann et al. |
| 5,873,862 A | 2/1999 | Lopez |
| 5,879,713 A | 3/1999 | Roth et al. |
| 5,882,494 A | 3/1999 | Van Antwerp |
| 5,885,566 A | 3/1999 | Goldberg |
| 5,897,955 A | 4/1999 | Drumheller |
| 5,914,026 A | 6/1999 | Blubaugh, Jr. et al. |
| 5,914,182 A | 6/1999 | Drumheller |
| 5,931,814 A | 8/1999 | Alex et al. |
| 5,932,299 A | 8/1999 | Katoot |
| 5,945,498 A | 8/1999 | Hopken et al. |
| 5,947,127 A | 9/1999 | Tsugaya et al. |
| 5,954,643 A | 9/1999 | Van Antwerp et al. |
| 5,955,066 A | 9/1999 | Sako et al. |
| 5,957,854 A | 9/1999 | Besson et al. |
| 5,959,191 A | 9/1999 | Lewis et al. |
| 5,961,451 A | 10/1999 | Reber et al. |
| 5,964,993 A | 10/1999 | Blubaugh et al. |
| 5,965,380 A | 10/1999 | Heller et al. |
| 5,969,076 A | 10/1999 | Lai et al. |
| 5,972,199 A | 10/1999 | Heller |
| 5,977,241 A | 11/1999 | Koloski et al. |
| 5,985,129 A | 11/1999 | Gough et al. |
| 5,987,352 A | 11/1999 | Klein et al. |
| 6,001,067 A | 12/1999 | Shults et al. |
| 6,001,471 A | 12/1999 | Bries et al. |
| 6,002,954 A | 12/1999 | Van Antwerp et al. |
| 6,007,845 A | 12/1999 | Domb |
| 6,011,984 A | 1/2000 | Van Antwerp et al. |
| 6,018,013 A | 1/2000 | Yoshida et al. |
| 6,018,033 A | 1/2000 | Chen et al. |
| 6,022,463 A | 2/2000 | Leader et al. |
| 6,030,827 A | 2/2000 | Davis et al. |
| 6,039,913 A | 3/2000 | Hirt et al. |
| 6,043,328 A | 3/2000 | Domschke et al. |
| 6,051,389 A | 4/2000 | Ahl et al. |
| 6,059,946 A | 5/2000 | Yukawa et al. |
| 6,063,637 A | 5/2000 | Arnold et al. |
| 6,066,448 A | 5/2000 | Wohlstadter et al. |
| 6,071,406 A | 6/2000 | Tsou |
| 6,081,736 A | 6/2000 | Colvin et al. |
| 6,083,523 A | 7/2000 | Dionne et al. |
| 6,083,710 A | 7/2000 | Heller et al. |
| 6,088,608 A | 7/2000 | Schulman et al. |
| 6,091,975 A | 7/2000 | Daddona et al. |
| 6,093,172 A | 7/2000 | Funderburk et al. |
| 6,119,028 A | 9/2000 | Schulman et al. |
| 6,121,009 A | 9/2000 | Heller et al. |
| 6,122,536 A | 9/2000 | Sun et al. |
| 6,134,461 A | 10/2000 | Say et al. |
| 6,157,860 A | 12/2000 | Hauger et al. |
| 6,162,611 A | 12/2000 | Heller et al. |
| 6,175,752 B1 | 1/2001 | Say et al. |
| 6,200,772 B1 | 3/2001 | Vadgama et al. |
| 6,212,416 B1 | 4/2001 | Ward et al. |
| 6,231,879 B1 | 5/2001 | Li et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,256,522 B1 | 7/2001 | Schultz |
| 6,259,937 B1 | 7/2001 | Schulman et al. |
| 6,264,825 B1 | 7/2001 | Blackburn et al. |

(56) References Cited

U.S. PATENT DOCUMENTS

| | | |
|---|---|---|
| 6,271,332 B1 | 8/2001 | Lohmann et al. |
| 6,275,717 B1 | 8/2001 | Gross et al. |
| 6,281,015 B1 | 8/2001 | Mooney et al. |
| 6,284,478 B1 | 9/2001 | Heller et al. |
| 6,299,583 B1 | 10/2001 | Eggers et al. |
| 6,303,670 B1 | 10/2001 | Fujino et al. |
| 6,306,594 B1 | 10/2001 | Cozzette |
| 6,312,706 B1 | 11/2001 | Lai et al. |
| 6,325,978 B1 | 12/2001 | Labuda et al. |
| 6,329,161 B1 | 12/2001 | Heller et al. |
| 6,329,488 B1 | 12/2001 | Terry et al. |
| 6,343,225 B1 | 1/2002 | Clark, Jr. |
| 6,358,557 B1 | 3/2002 | Wang et al. |
| 6,368,658 B1 | 4/2002 | Schwarz et al. |
| 6,379,883 B2 | 4/2002 | Davis et al. |
| 6,387,379 B1 | 5/2002 | Goldberg et al. |
| 6,395,325 B1 | 5/2002 | Hedge et al. |
| 6,405,066 B1 | 6/2002 | Essenpreis et al. |
| 6,407,195 B2 | 6/2002 | Sherman et al. |
| 6,413,393 B1 | 7/2002 | Van Antwerp et al. |
| 6,424,847 B1 | 7/2002 | Mastrototaro et al. |
| 6,442,413 B1 | 8/2002 | Silver |
| 6,447,542 B1 | 9/2002 | Weadock |
| 6,459,917 B1 | 10/2002 | Gowda et al. |
| 6,461,496 B1 | 10/2002 | Feldman et al. |
| 6,466,810 B1 | 10/2002 | Ward et al. |
| 6,471,689 B1 | 10/2002 | Joseph et al. |
| 6,477,395 B2 | 11/2002 | Schulman et al. |
| 6,484,046 B1 | 11/2002 | Say et al. |
| 6,497,729 B1 | 12/2002 | Moussy |
| 6,498,043 B1 | 12/2002 | Schulman et al. |
| 6,512,939 B1 | 1/2003 | Colvin et al. |
| 6,514,718 B2 | 2/2003 | Heller et al. |
| 6,520,326 B2 | 2/2003 | McIvor et al. |
| 6,528,584 B2 | 3/2003 | Kennedy et al. |
| 6,551,496 B1 | 4/2003 | Moles et al. |
| 6,554,822 B1 | 4/2003 | Holschneider et al. |
| 6,554,982 B1 | 4/2003 | Shin et al. |
| 6,558,321 B1 | 5/2003 | Burd et al. |
| 6,565,509 B1 | 5/2003 | Say et al. |
| 6,565,807 B1 | 5/2003 | Patterson et al. |
| 6,569,521 B1 | 5/2003 | Sheridan et al. |
| 6,579,498 B1 | 6/2003 | Eglise |
| 6,596,294 B2 | 7/2003 | Lai et al. |
| 6,613,379 B2 | 9/2003 | Ward et al. |
| 6,618,934 B1 | 9/2003 | Feldman et al. |
| 6,633,772 B2 | 10/2003 | Ford et al. |
| 6,642,015 B2 | 11/2003 | Vachon et al. |
| 6,654,625 B1 | 11/2003 | Say et al. |
| 6,670,115 B1 | 12/2003 | Zhang |
| 6,673,596 B1 | 1/2004 | Sayler et al. |
| 6,689,265 B2 | 2/2004 | Heller et al. |
| 6,702,857 B2 | 3/2004 | Brauker et al. |
| 6,702,972 B1 | 3/2004 | Markle |
| 6,721,587 B2 | 4/2004 | Gough |
| 6,741,877 B1 | 5/2004 | Shults et al. |
| 6,784,274 B2 | 8/2004 | van Antwerp et al. |
| 6,789,634 B1 | 9/2004 | Denton |
| 6,793,789 B2 | 9/2004 | Choi et al. |
| 6,801,041 B2 | 10/2004 | Karinka et al. |
| 6,802,957 B2 | 10/2004 | Jung et al. |
| 6,809,653 B1 | 10/2004 | Mann et al. |
| 6,821,295 B1 | 11/2004 | Farrar |
| 6,858,218 B2 | 2/2005 | Lai et al. |
| 6,862,465 B2 | 3/2005 | Shults et al. |
| 6,867,262 B1 | 3/2005 | Angel et al. |
| 6,875,386 B1 | 4/2005 | Ward et al. |
| 6,881,551 B2 | 4/2005 | Heller et al. |
| 6,891,317 B2 | 5/2005 | Pei et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,895,265 B2 | 5/2005 | Silver |
| 6,908,681 B2 | 6/2005 | Terry et al. |
| 6,932,894 B2 | 8/2005 | Mao et al. |
| 6,965,791 B1 | 11/2005 | Hitchcock et al. |
| 6,969,451 B2 | 11/2005 | Shin et al. |
| 6,973,706 B2 | 12/2005 | Say et al. |
| 7,008,979 B2 | 3/2006 | Schottman et al. |
| 7,014,948 B2 | 3/2006 | Lee et al. |
| 7,033,322 B2 | 4/2006 | Silver |
| 7,052,131 B2 | 5/2006 | McCabe et al. |
| 7,074,307 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,118,667 B2 | 10/2006 | Lee |
| 7,120,483 B2 | 10/2006 | Russell et al. |
| 7,136,689 B2 | 11/2006 | Shults et al. |
| 7,144,496 B2 | 12/2006 | Meserol et al. |
| 7,146,202 B2 | 12/2006 | Ward et al. |
| 7,153,265 B2 | 12/2006 | Vachon |
| 7,157,528 B2 | 1/2007 | Ward |
| 7,172,075 B1 | 2/2007 | Ji |
| 7,192,450 B2 | 3/2007 | Brauker et al. |
| 7,226,978 B2 | 6/2007 | Tapsak et al. |
| 7,228,162 B2 | 6/2007 | Ward et al. |
| 7,229,471 B2 | 6/2007 | Gale et al. |
| 7,241,586 B2 | 7/2007 | Gulati |
| 7,247,138 B2 | 7/2007 | Reghabi et al. |
| 7,248,906 B2 | 7/2007 | Dirac et al. |
| 7,279,174 B2 | 10/2007 | Pacetti et al. |
| 7,316,662 B2 | 1/2008 | Delnevo et al. |
| 7,335,286 B2 | 2/2008 | Abel et al. |
| 7,336,984 B2 | 2/2008 | Gough et al. |
| 7,357,793 B2 | 4/2008 | Pacetti |
| 7,364,562 B2 | 4/2008 | Braig et al. |
| 7,366,556 B2 | 4/2008 | Brister et al. |
| 7,379,765 B2 | 5/2008 | Petisce et al. |
| 7,417,164 B2 | 8/2008 | Suri |
| 7,423,074 B2 | 9/2008 | Lai et al. |
| 7,433,727 B2 | 10/2008 | Ward et al. |
| 7,470,488 B2 | 12/2008 | Lee et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,613,491 B2 | 11/2009 | Boock et al. |
| 7,671,162 B2 | 3/2010 | Ward et al. |
| 7,687,586 B2 | 3/2010 | Ward et al. |
| 7,729,737 B2 | 6/2010 | Ward |
| 7,884,171 B2 | 2/2011 | Ward et al. |
| 7,920,907 B2 | 4/2011 | McGarraugh et al. |
| 7,970,449 B2 | 6/2011 | Ward |
| RE43,187 E | 2/2012 | Russell et al. |
| 8,160,670 B2 | 4/2012 | Ouyang et al. |
| 8,187,433 B2 | 5/2012 | Ward et al. |
| 8,346,335 B2 | 1/2013 | Harper et al. |
| 8,346,337 B2 | 1/2013 | Heller et al. |
| 8,583,204 B2 | 11/2013 | Boock et al. |
| 8,660,628 B2 | 2/2014 | Wang et al. |
| 8,682,408 B2 | 3/2014 | Boock et al. |
| 8,954,128 B2 * | 2/2015 | Boock ............... A61B 5/14532 600/347 |
| 2002/0009810 A1 | 1/2002 | O'Connor et al. |
| 2002/0018843 A1 | 2/2002 | Van Antwerp et al. |
| 2002/0023852 A1 | 2/2002 | McIvor et al. |
| 2002/0055673 A1 | 5/2002 | Van Antwerp et al. |
| 2002/0123087 A1 | 9/2002 | Vachon et al. |
| 2002/0128419 A1 | 9/2002 | Terry et al. |
| 2002/0128546 A1 | 9/2002 | Silver |
| 2002/0162792 A1 | 11/2002 | Zepf |
| 2002/0182241 A1 | 12/2002 | Boerenstein et al. |
| 2002/0185384 A1 | 12/2002 | Leong et al. |
| 2002/0193885 A1 | 12/2002 | Legeay et al. |
| 2003/0006669 A1 | 1/2003 | Pei et al. |
| 2003/0009093 A1 | 1/2003 | Silver |
| 2003/0023317 A1 | 1/2003 | Brauker et al. |
| 2003/0031699 A1 | 2/2003 | Van Antwerp |
| 2003/0031911 A1 | 2/2003 | Ritts et al. |
| 2003/0032874 A1 | 2/2003 | Rhodes et al. |
| 2003/0059631 A1 | 3/2003 | Al-Lamee |
| 2003/0065254 A1 | 4/2003 | Schulman et al. |
| 2003/0069383 A1 | 4/2003 | Van Antwerp et al. |
| 2003/0072741 A1 | 4/2003 | Berglund et al. |

(56) References Cited

U.S. PATENT DOCUMENTS

| | | |
|---|---|---|
| 2003/0078481 A1 | 4/2003 | McIvor et al. |
| 2003/0088166 A1 | 5/2003 | Say et al. |
| 2003/0096424 A1 | 5/2003 | Mao et al. |
| 2003/0104273 A1 | 6/2003 | Lee et al. |
| 2003/0125498 A1 | 7/2003 | McCabe et al. |
| 2003/0132227 A1 | 7/2003 | Geisler |
| 2003/0134100 A1 | 7/2003 | Mao et al. |
| 2003/0134347 A1 | 7/2003 | Heller et al. |
| 2003/0157409 A1 | 8/2003 | Huang et al. |
| 2003/0181794 A1 | 9/2003 | Rini et al. |
| 2003/0199745 A1 | 10/2003 | Burson et al. |
| 2003/0199878 A1 | 10/2003 | Pohjonen |
| 2003/0203991 A1 | 10/2003 | Schottman et al. |
| 2003/0211050 A1 | 11/2003 | Majeti et al. |
| 2003/0217966 A1 | 11/2003 | Tapsak et al. |
| 2003/0225324 A1 | 12/2003 | Anderson et al. |
| 2003/0228681 A1 | 12/2003 | Ritts et al. |
| 2003/0235817 A1 | 12/2003 | Bartkowiak et al. |
| 2004/0006263 A1 | 1/2004 | Anderson et al. |
| 2004/0011671 A1 | 1/2004 | Shults et al. |
| 2004/0023253 A1 | 2/2004 | Kunwar et al. |
| 2004/0030294 A1 | 2/2004 | Mahurkar |
| 2004/0045879 A1 | 3/2004 | Shults et al. |
| 2004/0063167 A1 | 4/2004 | Kaastrup et al. |
| 2004/0074785 A1 | 4/2004 | Holker |
| 2004/0078219 A1 | 4/2004 | Kaylor |
| 2004/0084306 A1 | 5/2004 | Shin et al. |
| 2004/0106741 A1 | 6/2004 | Kriesel et al. |
| 2004/0106857 A1 | 6/2004 | Gough |
| 2004/0111017 A1 | 6/2004 | Say et al. |
| 2004/0111144 A1 | 6/2004 | Lawin et al. |
| 2004/0120848 A1 | 6/2004 | Teodorczyk |
| 2004/0138543 A1 | 7/2004 | Russell et al. |
| 2004/0143173 A1 | 7/2004 | Reghabi et al. |
| 2004/0146909 A1 | 7/2004 | Duong et al. |
| 2004/0167801 A1 | 8/2004 | Say et al. |
| 2004/0176672 A1 | 9/2004 | Silver et al. |
| 2004/0180391 A1 | 9/2004 | Gratzl et al. |
| 2004/0186362 A1 | 9/2004 | Brauker et al. |
| 2004/0213985 A1 | 10/2004 | Lee et al. |
| 2004/0224001 A1 | 11/2004 | Pacetti et al. |
| 2004/0228902 A1 | 11/2004 | Benz |
| 2004/0234575 A1 | 11/2004 | Horres et al. |
| 2005/0003399 A1 | 1/2005 | Blackburn et al. |
| 2005/0013842 A1 | 1/2005 | Qiu et al. |
| 2005/0031689 A1 | 2/2005 | Shults et al. |
| 2005/0033132 A1 | 2/2005 | Shults et al. |
| 2005/0051440 A1 | 3/2005 | Simpson et al. |
| 2005/0054909 A1 | 3/2005 | Petisce et al. |
| 2005/0070770 A1 | 3/2005 | Dirac et al. |
| 2005/0077584 A1 | 4/2005 | Uhland et al. |
| 2005/0079200 A1 | 4/2005 | Rathenow et al. |
| 2005/0090607 A1 | 4/2005 | Tapsak et al. |
| 2005/0103625 A1 | 5/2005 | Rhodes et al. |
| 2005/0107677 A1 | 5/2005 | Ward et al. |
| 2005/0112169 A1 | 5/2005 | Brauker et al. |
| 2005/0112172 A1 | 5/2005 | Pacetti |
| 2005/0112358 A1 | 5/2005 | Potyrailo et al. |
| 2005/0115832 A1 | 6/2005 | Simpson et al. |
| 2005/0118344 A1 | 6/2005 | Pacetti |
| 2005/0119720 A1 | 6/2005 | Gale et al. |
| 2005/0121322 A1 | 6/2005 | Say |
| 2005/0124873 A1 | 6/2005 | Shults et al. |
| 2005/0139489 A1 | 6/2005 | Davies et al. |
| 2005/0143635 A1 | 6/2005 | Kamath et al. |
| 2005/0154272 A1 | 7/2005 | Dirac et al. |
| 2005/0173245 A1 | 8/2005 | Feldman et al. |
| 2005/0176136 A1 | 8/2005 | Burd et al. |
| 2005/0176678 A1 | 8/2005 | Horres et al. |
| 2005/0177036 A1 | 8/2005 | Shults et al. |
| 2005/0184641 A1 | 8/2005 | Armitage et al. |
| 2005/0196747 A1 | 9/2005 | Stiene |
| 2005/0197554 A1 | 9/2005 | Polcha |
| 2005/0209665 A1 | 9/2005 | Hunter et al. |
| 2005/0215871 A1 | 9/2005 | Feldman et al. |
| 2005/0221276 A1 | 10/2005 | Rozakis et al. |
| 2005/0233407 A1 | 10/2005 | Pamidi et al. |
| 2005/0239154 A1 | 10/2005 | Feldman et al. |
| 2005/0242479 A1 | 11/2005 | Petisce et al. |
| 2005/0245799 A1 | 11/2005 | Brauker et al. |
| 2005/0271546 A1 | 12/2005 | Gerber et al. |
| 2005/0274665 A1 | 12/2005 | Heilmann et al. |
| 2005/0282997 A1 | 12/2005 | Ward |
| 2006/0001550 A1 | 1/2006 | Mann et al. |
| 2006/0003398 A1 | 1/2006 | Heller et al. |
| 2006/0007391 A1 | 1/2006 | McCabe et al. |
| 2006/0008370 A1 | 1/2006 | Massaro et al. |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0047095 A1 | 3/2006 | Pacetti |
| 2006/0052745 A1 | 3/2006 | Van Antwerp et al. |
| 2006/0058868 A1 | 3/2006 | Gale et al. |
| 2006/0065527 A1 | 3/2006 | Samproni |
| 2006/0067908 A1 | 3/2006 | Ding |
| 2006/0068208 A1 | 3/2006 | Tapsak et al. |
| 2006/0078908 A1 | 4/2006 | Pitner et al. |
| 2006/0079740 A1 | 4/2006 | Silver et al. |
| 2006/0086624 A1 | 4/2006 | Tapsak et al. |
| 2006/0134165 A1 | 6/2006 | Pacetti |
| 2006/0142524 A1 | 6/2006 | Lai et al. |
| 2006/0142525 A1 | 6/2006 | Lai et al. |
| 2006/0142526 A1 | 6/2006 | Lai et al. |
| 2006/0142651 A1 | 6/2006 | Brister et al. |
| 2006/0148985 A1 | 7/2006 | Karthauser |
| 2006/0155180 A1 | 7/2006 | Brister et al. |
| 2006/0159718 A1 | 7/2006 | Rathenow et al. |
| 2006/0159981 A1 | 7/2006 | Heller |
| 2006/0171980 A1 | 8/2006 | Helmus et al. |
| 2006/0177379 A1 | 8/2006 | Asgari |
| 2006/0183178 A1 | 8/2006 | Gulati |
| 2006/0183871 A1 | 8/2006 | Ward et al. |
| 2006/0189856 A1 | 8/2006 | Petisce et al. |
| 2006/0189863 A1 | 8/2006 | Peyser et al. |
| 2006/0195029 A1 | 8/2006 | Shults et al. |
| 2006/0198864 A1 | 9/2006 | Shults et al. |
| 2006/0200019 A1 | 9/2006 | Petisce et al. |
| 2006/0200970 A1 | 9/2006 | Brister et al. |
| 2006/0204536 A1 | 9/2006 | Shults et al. |
| 2006/0229512 A1 | 10/2006 | Petisce et al. |
| 2006/0249381 A1 | 11/2006 | Petisce et al. |
| 2006/0249446 A1 | 11/2006 | Yeager |
| 2006/0249447 A1 | 11/2006 | Yeager |
| 2006/0252027 A1 | 11/2006 | Petisce et al. |
| 2006/0253012 A1 | 11/2006 | Petisce et al. |
| 2006/0258761 A1 | 11/2006 | Boock et al. |
| 2006/0258929 A1 | 11/2006 | Goode et al. |
| 2006/0263673 A1 | 11/2006 | Kim et al. |
| 2006/0263839 A1 | 11/2006 | Ward et al. |
| 2006/0269586 A1 | 11/2006 | Pacetti |
| 2006/0275857 A1 | 12/2006 | Kjaer et al. |
| 2006/0275859 A1 | 12/2006 | Kjaer |
| 2006/0289307 A1 | 12/2006 | Yu et al. |
| 2006/0293487 A1 | 12/2006 | Gaymans et al. |
| 2006/0293576 A1 | 12/2006 | Van Antwerp et al. |
| 2007/0003588 A1 | 1/2007 | Chinn et al. |
| 2007/0007133 A1 | 1/2007 | Mang et al. |
| 2007/0032717 A1 | 2/2007 | Brister et al. |
| 2007/0032718 A1 | 2/2007 | Shults et al. |
| 2007/0038044 A1 | 2/2007 | Dobbles et al. |
| 2007/0045902 A1 | 3/2007 | Brauker et al. |
| 2007/0059196 A1 | 3/2007 | Brister et al. |

(56) References Cited

U.S. PATENT DOCUMENTS

| | | |
|---|---|---|
| 2007/0123963 A1 | 5/2007 | Krulevitch |
| 2007/0129524 A1 | 6/2007 | Sunkara |
| 2007/0135696 A1 | 6/2007 | Ward |
| 2007/0135698 A1 | 6/2007 | Shah et al. |
| 2007/0142584 A1 | 6/2007 | Schorzman et al. |
| 2007/0155851 A1 | 7/2007 | Alii et al. |
| 2007/0161769 A1 | 7/2007 | Schorzman et al. |
| 2007/0163880 A1 | 7/2007 | Woo et al. |
| 2007/0166343 A1 | 7/2007 | Goerne et al. |
| 2007/0166364 A1 | 7/2007 | Beier et al. |
| 2007/0173709 A1 | 7/2007 | Petisce et al. |
| 2007/0173710 A1 | 7/2007 | Petisce et al. |
| 2007/0179436 A1 | 8/2007 | Braig et al. |
| 2007/0197889 A1 | 8/2007 | Brister et al. |
| 2007/0197890 A1 | 8/2007 | Boock et al. |
| 2007/0200267 A1 | 8/2007 | Tsai |
| 2007/0202562 A1 | 8/2007 | Curry |
| 2007/0203568 A1 | 8/2007 | Gale et al. |
| 2007/0203573 A1 | 8/2007 | Rudakov et al. |
| 2007/0213611 A1 | 9/2007 | Simpson et al. |
| 2007/0215491 A1 | 9/2007 | Heller et al. |
| 2007/0218097 A1 | 9/2007 | Heller et al. |
| 2007/0227907 A1 | 10/2007 | Shah et al. |
| 2007/0229757 A1 | 10/2007 | McCabe et al. |
| 2007/0233013 A1 | 10/2007 | Schoenberg |
| 2007/0235331 A1 | 10/2007 | Simpson et al. |
| 2007/0242215 A1 | 10/2007 | Schorzman et al. |
| 2007/0244379 A1 | 10/2007 | Boock et al. |
| 2007/0275193 A1 | 11/2007 | DeSimone et al. |
| 2007/0299385 A1 | 12/2007 | Santini et al. |
| 2007/0299409 A1 | 12/2007 | Whitbourne et al. |
| 2008/0001318 A1 | 1/2008 | Schorzman et al. |
| 2008/0021008 A1 | 1/2008 | Pacetti et al. |
| 2008/0027301 A1 | 1/2008 | Ward et al. |
| 2008/0029391 A1 | 2/2008 | Mao et al. |
| 2008/0031918 A1 | 2/2008 | Lawin et al. |
| 2008/0033254 A1 | 2/2008 | Kamath et al. |
| 2008/0033269 A1 | 2/2008 | Zhang |
| 2008/0034972 A1 | 2/2008 | Gough et al. |
| 2008/0038307 A1 | 2/2008 | Hoffmann |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0071027 A1 | 3/2008 | Pacetti |
| 2008/0071157 A1 | 3/2008 | McGarraugh et al. |
| 2008/0071158 A1 | 3/2008 | McGarraugh et al. |
| 2008/0076897 A1 | 3/2008 | Kunzler et al. |
| 2008/0081184 A1 | 4/2008 | Kubo et al. |
| 2008/0113207 A1 | 5/2008 | Pacetti et al. |
| 2008/0138497 A1 | 6/2008 | Pacetti et al. |
| 2008/0138498 A1 | 6/2008 | Pacetti et al. |
| 2008/0143014 A1 | 6/2008 | Tang |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0208026 A1 | 8/2008 | Noujaim et al. |
| 2008/0213460 A1 | 9/2008 | Benter et al. |
| 2008/0242961 A1 | 10/2008 | Brister et al. |
| 2008/0305009 A1 | 12/2008 | Gamsey et al. |
| 2008/0305506 A1 | 12/2008 | Suri |
| 2008/0312397 A1 | 12/2008 | Lai et al. |
| 2009/0004243 A1 | 1/2009 | Pacetti et al. |
| 2009/0012205 A1 | 1/2009 | Nakada et al. |
| 2009/0018418 A1 | 1/2009 | Markle et al. |
| 2009/0018424 A1 | 1/2009 | Kamath et al. |
| 2009/0018426 A1 | 1/2009 | Markle et al. |
| 2009/0030294 A1 | 1/2009 | Petisce et al. |
| 2009/0036763 A1 | 2/2009 | Brauker et al. |
| 2009/0045055 A1 | 2/2009 | Rhodes et al. |
| 2009/0061528 A1 | 3/2009 | Suri |
| 2009/0076356 A1 | 3/2009 | Simpson |
| 2009/0076360 A1 | 3/2009 | Brister et al. |
| 2009/0076361 A1 | 3/2009 | Kamath et al. |
| 2009/0081803 A1 | 3/2009 | Gamsey et al. |
| 2009/0099436 A1 | 4/2009 | Brister et al. |
| 2009/0177143 A1 | 7/2009 | Markle et al. |
| 2009/0247855 A1 | 10/2009 | Boock et al. |
| 2009/0247856 A1 | 10/2009 | Boock et al. |
| 2009/0264719 A1 | 10/2009 | Markle et al. |
| 2009/0281406 A1 | 11/2009 | McGarraugh et al. |
| 2010/0096259 A1 | 4/2010 | Zhang et al. |
| 2010/0119693 A1 | 5/2010 | Tapsak et al. |
| 2010/0274107 A1 | 10/2010 | Boock et al. |
| 2010/0280341 A1 | 11/2010 | Boock et al. |
| 2011/0152654 A1 | 6/2011 | Wang et al. |
| 2012/0108929 A1 | 5/2012 | Peyser et al. |
| 2014/0148666 A1 | 5/2014 | Boock et al. |
| 2014/0148667 A1 | 5/2014 | Boock et al. |
| 2015/0038815 A1* | 2/2015 | Boock ............. A61B 5/14532 600/347 |
| 2015/0112174 A1* | 4/2015 | Boock ............. A61B 5/14532 600/347 |
| 2015/0282750 A1 | 10/2015 | Boock et al. |

FOREIGN PATENT DOCUMENTS

| | | |
|---|---|---|
| EP | 0 286 118 | 10/1988 |
| EP | 0 291 130 | 11/1988 |
| EP | 0 313 951 | 5/1989 |
| EP | 0 320 109 | 6/1989 |
| EP | 0 351 892 | 1/1990 |
| EP | 0 353 328 | 2/1990 |
| EP | 0 362 145 | 4/1990 |
| EP | 0 390 390 | 10/1990 |
| EP | 0 396 788 | 11/1990 |
| EP | 0 477 501 | 4/1992 |
| EP | 0 535 898 | 4/1993 |
| EP | 0 351 891 | 9/1993 |
| EP | 0 563 795 | 10/1993 |
| EP | 0 747 069 | 12/1996 |
| EP | 0 817 809 | 1/1998 |
| EP | 0 862 648 | 9/1998 |
| EP | 0 885 932 | 12/1998 |
| EP | 1 112 717 | 7/2001 |
| EP | 1 112 718 | 7/2001 |
| EP | 1 120 084 | 8/2001 |
| EP | 1 120 085 | 8/2001 |
| EP | 0 789 540 | 9/2001 |
| EP | 0 515194 | 10/2001 |
| EP | 1 251 137 | 10/2002 |
| EP | 1 413 245 | 4/2004 |
| EP | 1 496 126 | 8/2005 |
| EP | 1 560 625 | 8/2007 |
| EP | 1 466 156 | 5/2008 |
| EP | 1 927 602 | 6/2008 |
| GB | 2149918 | 6/1985 |
| GB | 2209836 | 5/1989 |
| JP | 57156004 | 9/1982 |
| JP | 57156005 | 9/1982 |
| JP | 58163402 | 9/1983 |
| JP | 58163403 | 9/1983 |
| JP | 59029693 | 2/1984 |
| JP | 59049803 | 3/1984 |
| JP | 59049805 | 3/1984 |
| JP | 59059221 | 4/1984 |
| JP | 59087004 | 5/1984 |
| JP | 59209608 | 11/1984 |
| JP | 59209609 | 11/1984 |
| JP | 59209610 | 11/1984 |
| JP | 59211459 | 11/1984 |
| JP | 60245623 | 12/1985 |
| JP | 61238319 | 10/1986 |
| JP | 62074406 | 4/1987 |
| JP | 62102815 | 5/1987 |
| JP | 62227423 | 10/1987 |
| JP | 63130661 | 6/1988 |
| JP | 01018404 | 1/1989 |
| JP | 01018405 | 1/1989 |
| JP | 05279447 | 10/1993 |
| JP | 8196626 | 8/1996 |
| WO | WO 89-02720 | 4/1989 |
| WO | WO 89-05977 | 6/1989 |
| WO | WO 90-05910 | 5/1990 |
| WO | WO 90-07575 | 7/1990 |

(56) References Cited

FOREIGN PATENT DOCUMENTS

| WO | WO 90-10861 | 9/1990 |
|---|---|---|
| WO | WO 92-13271 | 8/1992 |
| WO | WO 93-13408 | 7/1993 |
| WO | WO 93-14185 | 7/1993 |
| WO | WO 93-14693 | 8/1993 |
| WO | WO 93-23744 | 11/1993 |
| WO | WO 94-03812 | 2/1994 |
| WO | WO 94-08236 | 4/1994 |
| WO | WO 95-06877 | 3/1995 |
| WO | WO 95-13838 | 5/1995 |
| WO | WO 95-17966 | 7/1995 |
| WO | WO 95-22051 | 8/1995 |
| WO | WO 95-22057 | 8/1995 |
| WO | WO 96-01611 | 1/1996 |
| WO | WO 96-09532 | 3/1996 |
| WO | WO 96-14026 | 5/1996 |
| WO | WO 96-025089 | 8/1996 |
| WO | WO 96-30431 | 10/1996 |
| WO | WO 97-01986 | 1/1997 |
| WO | WO 97-11067 | 3/1997 |
| WO | WO 98-24366 | 6/1998 |
| WO | WO 98-45427 | 10/1998 |
| WO | WO 99-13099 | 3/1999 |
| WO | WO 99-56613 | 4/1999 |
| WO | WO 99-38003 | 10/1999 |
| WO | WO 99-58709 | 11/1999 |
| WO | WO 00-19887 | 4/2000 |
| WO | WO 00-33065 | 6/2000 |
| WO | WO 00-45696 | 8/2000 |
| WO | WO 00-49940 | 8/2000 |
| WO | WO 00-59373 | 10/2000 |
| WO | WO 00-74753 | 12/2000 |
| WO | WO 01-12158 | 2/2001 |
| WO | WO 01-87151 | 11/2001 |
| WO | WO 02-053764 | 7/2002 |
| WO | WO 02-089666 | 11/2002 |
| WO | WO 03-022125 | 3/2003 |
| WO | WO 03-085372 | 10/2003 |
| WO | WO 03-101862 | 12/2003 |
| WO | WO 2004-011947 | 2/2004 |
| WO | WO 2004-042382 | 5/2004 |
| WO | WO 2004-052447 | 6/2004 |
| WO | WO 2004-104070 | 12/2004 |
| WO | WO 2005-032362 | 4/2005 |
| WO | 2005-044088 | 5/2005 |
| WO | WO 2005-045394 | 5/2005 |
| WO | WO 2005-048834 | 6/2005 |
| WO | WO 2005-121355 | 12/2005 |
| WO | WO 2006-002960 | 1/2006 |
| WO | WO 2006-018425 | 2/2006 |
| WO | WO 2006-029293 | 3/2006 |
| WO | WO 2006-071770 | 7/2006 |
| WO | WO 2006-076412 | 7/2006 |
| WO | WO 2006-088576 | 8/2006 |
| WO | WO 2007-070486 | 6/2007 |
| WO | WO 2007-079025 | 7/2007 |
| WO | WO 2007-114943 | 10/2007 |
| WO | WO 2007-121180 | 10/2007 |
| WO | WO 2007-127622 | 11/2007 |
| WO | WO 2007-147475 | 12/2007 |
| WO | WO 2008-013849 | 1/2008 |

OTHER PUBLICATIONS

Aalders et al. 1991. Development of a wearable glucose sensor; studies in healthy volunteers and in diabetic patients. The International Journal of Artificial Organs 14(2):102-108.

Abe et al. 1992. Characterization of glucose microsensors for intracellular measurements. Analytical Chemistry 64(18):2160-2163.

Abel et al. 1984. Experience with an implantable glucose sensor as a prerequisite of an artificial beta cell. Biomed. Biochim. Acta 43(5):577-584.

Abel et al. 2002. Biosensors for in vivo glucose measurement: can we cross the experimental stage. Biosensors & Bioelectronics 17:1059-1070.

Alcock & Turner. 1994. Continuous Analyte Monitoring to Aid Clinical Practice. IEEE Engineering in Med. & Biol. 13:319-325.

American Heritage Dictionary 4th Edition. 2000. Houghton Mifflin Company p. 82.

Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic." The American Heritage Stedman's Medical Dictionary. Houghton Mifflin Company 2002. Answers. com Nov. 7, 2006 http:--www. Answers.com-topic-xenogenic.

Armour et al. Dec. 1990. Application of Chronic Intravascular Blood Glucose Sensor in Dogs. Diabetes 39:1519-1526.

Asberg et al. 2003. Hydrogels of a Conducting Conjugated Polymer as 3-D Enzyme Electrode. Biosensors Bioelectronics 19:199-207.

Assolant-Vinet et al. 1986. New Immobilized Enzyme Membranes for Tailor-Made Biosensors. Anal Letters 19(7&8):875-885.

Atanasov et al. 1994. Biosensor for continuous glucose monitoring. Biotechnology and Bioengineering 43:262-266.

Atanasov et al. 1997. Implantation of a refillable glucose monitoring-telemetry device. Biosensors & Bioelectronics 12:669-680.

Aussedat et al. 1997. A user-friendly method for calibrating a subcutaneous glucose sensor-based hypoglycaemic alarm. Biosensors & Bioelectronics 12(11):1061-1071.

Bailey et al. 2007. Reduction in hemoglobin A1c with real-time continuous glucose monitoring: results from a 12-week observational study. Diabetes Technology & Therapeutics 9(3):203-210.

Baker R.W. 2008. Vapor and Gas Separation by Membranes in Advanced Membrane Technology and Applications [Eds. Li et al.] John Wiley & Sons Inc. Chapter 21 pp. 559-580.

Beach et al. 1999. Subminiature implantable potentiostat and modified commercial telemetry device for remote glucose monitoring. IEEE Transactions on Instrumentation and Measurement 48(6):1239-1245.

Bellucci et al. Jan. 1986. Electrochemical behavior of graphite-epoxy composite materials (GECM) in aqueous salt solutions. Journal of Applied Electrochemistry 16(1):15-22.

Bessman et al. 1973. Progress toward a glucose sensor for the artificial pancreas. Proceedings of a Workshop on Ion-Selective Microelectrodes Jun. 4-5, 1973 Boston MA pp. 189-197.

Biermann et al. 2008. How would patients behave if they were continually informed of their blood glucose levels? A simulation study using a "virtual" patient. Diabetes Technology & Therapeutics 10:178-187.

Bindra et al. 1989. Pulsed amperometric detection of glucose in biological fluids at a surface-modified gold electrode. Analytical Chemistry 61:2566-2570.

Bindra et al. 1991. Design and In Vitro Studies of a Needle-Type Glucose Senso for Subcutaneous Monitoring. Analytical Chemistry 63:1692-1696.

Bisenberger et al. 1995. A triple-step potential waveform at enzyme multisensors with thick-film gold electrodes for detection of glucose and sucrose. Sensors and Actuators B 28:181-189.

Bland et al. 1990. A note on the use of the intraclass correlation coefficient in the evaluation of agreement between two methods of measurement. Comput. Biol. Med. 20(5):337-340.

Bobbioni-Harsch et al. 1993. Lifespan of subcutaneous glucose sensors and their performances during dynamic glycaemia changes in rats. J. Biomedical Engineering 15:457-463.

Bode et al. 1999. Continuous glucose monitoring used to adjust diabetes therapy improves glycosylated hemoglobin: A pilot study. Diabetes Research and Clinical Practice 46:183-190.

Bode et al. 2000. Using the continuous glucose monitoring system to improve the management of type 1 diabetes. Diabetes Technology & Therapeutics 2(Suppl 1):S43-S48.

Bode B. W. 2000. Clinical utility of the continuous glucose monitoring system. Diabetes Technology & Therapeutics 2(Suppl 1):S35-S41.

Boedeker Plastics Inc. 2009. Polyethylene Specifications Data Sheet http:--www.boedeker.com-polye_p.htm [Aug. 19, 2009 3:36:33 PM].

(56) References Cited

OTHER PUBLICATIONS

Boland et al. 2001. Limitations of conventional methods of self-monitoring of blood glucose. Diabetes Care 24(11):1858-1862.
Bott A. W. 1997. A Comparison of Cyclic Voltammetry and Cyclic Staircase Voltammetry. Current Separations 16:1 23-26.
Bowman L.; Meindl J. D. 1986. The packaging of implantable integrated sensors. IEEE Transactions in Biomedical Engineering (BME)33(2):248-255.
Brauker et al. 1995. Neovascularization of synthetic membranes directed by membrane Microarchitecture. J. Biomed Mater Res 29:1517-1524.
Brauker et al. 1998. Sustained expression of high levels of human factor IX from human cells implanted within an immunoisolation device into athymic rodents. Hum Gene Ther 9:879-888.
Brauker et al. 2001. Unraveling Mysteries at the Biointerface: Molecular Mediator of Inhibition of Blood Vessel Formation in the Foreign Body Capsule Revealed. Surfacts Biomaterials 6. 1; 5.
Brauker et al. Jun. 27, 1996. Local Inflammatory Response Around Diffusion Chambers Containing Xenografts. Transplantation 61(12):1671-1677.
Braunwald 2008. Biomarkers in heart failure. N. Engl. J. Med. 358:2148-2159.
Bremer et al. 2001. Benchmark data from the literature for evaluation of new glucose sensing technologies. Diabetes Technology & Therapeutics 3(3):409-418.
Brooks et al. 1987-88. Development of an on-line glucose sensor for fermentation monitoring. Biosensors 3:45-56.
Bruckel et al. 1989. In vivo measurement of subcutaneous glucose concentrations with an enzymatic glucose sensor and a wick method. Klin Wochenschr 67:491-495.
Brunner et al. 1998. Validation of home blood glucose meters with respect to clinical and analytical approaches. Diabetes Care 21(4):585-590.
Cai et al. 2004. A wireless remote query glucose biosensor based on a pH-sensitive polymer. Analytical Chemistry 76(4):4038-4043.
Campanella et al. 1993. Biosensor for direct determination of glusose and lactate in undiluted biological fluids. Biosensors & Bioelectronics 8:307-314.
Candas et al 1994. An adaptive plasma glucose controller based on a nonlinear insulin-glucose model. IEEE Transactions on Biomedical Engineering (BME) 41(2):116-124.
Cass et al. 1984. Ferrocene-mediated enzyme electrodes for amperometric determination of glucose. Analytical Chemistry 36:667-671.
Cassidy et al. Apr. 1993. Novel electrochemical device for the detection of cholesterol or glucose. Analyst 118:415-418.
Cellulose Acetate Product Description Product No. 419028 Sigma-Aldrich Corp. St. Louis MO. 2005.
Chase et al. 2001. Continuous subcutaneous glucose monitoring in children with type 1 diabetes. Pediatrics 107:222-226.
Chatterjee et al. 1997. Poly(ether Urethane) and poly(ether urethane urea) membranes with high H2S-CH4 selectivity. Journal of Membrane Science 135:99-106.
Chen et al. 2006. A noninterference polypyrrole glucose biosensor. Biosensors and Bioelectronics 22:639-643.
Ciba® Irgacure® 2959 Photoinitiator Product Description. Apr. 2, 1998. Ciba Specialty Chemicals Inc. Basel Switzerland [3 pages].
Claremont et al. 1986. Subcutaneous implantation of a ferrocene-mediated glucose sensor in pigs. Diabetologia 29:817-821.
Claremont et al. Jul. 1986. Potentially-implantable ferrocene-mediated glucose sensor. J. Biomedical Engineering 8:272-274.
Clark et al. 1987. Configurational cyclic voltammetry: increasing the specificity and reliablity of implanted electrodes. IEEE-Ninth Annual Conference of the Engineering in Medicine and Biology Society (EMB) pp. 0782-0783.
Clark et al. 1988. Long-term stability of electroenzymatic glucose sensors implanted in mice. Trans Am Soc Artif Intern Organs 34:259-265.

Clark et al. 1981. One-minute electrochemical enzymic assay for cholesterol in biological materials. Clinical Chemistry 27(12):1978-1982.
CLSI. Performance metrics for continuous interstitial glucose monitoring; approved guideline CLSI Document POCT05-A. Wayne PA: Clinical and Laboratory Standards Institute: 2008 28(33) [72 pages].
Colangelo et al. 1967. Corrosion rate measurements in vivo. Journal of Biomedical Materials Research 1:405-414.
Colowick et al. 1976. Methods in Enzymlology vol. XLIV Immobilized Enzymes. New York: Academic Press.
Cox et al. 1985. Accuracy of perceiving blood glucose in IDDM. Diabetes Care 8(6):529-536.
Csoregi et al. 1994. Design characterization and one-point in vivo calibration of a subcutaneously implanted glucose electrode. Analytical Chemistry. 66(19):3131-3138.
Dai et al. 1999. Hydrogel Membranes with Mesh Size Asymmetry Based on the Gradient Crosslink of Poly(vinyl alcohol). Journal of Membrane Science 156:67-79.
Danielsson et al. 1988. Enzyme thermistors. Methods in Enzymology 137:181-197.
D'Arrigo et al. 2003. Porous-Si based bioreactors for glucose monitoring and drugs production. Proc. of SPIE 4982:178-184.
Dassau et al. 2009. In silico evaluation platform for artificial pancreatic (3-cell development—a dynamic simulator for closed loop control with hardware-in-the-loop. Diabetes Technology & Therapeutics 11(3):1-8.
Davies et al. 1992. Polymer membranes in clinical sensor applications. I. An overview of membrane function. Biomaterials 13(14):971-978.
Davis et al. 1983. Bioelectrochemical fuel cell and sensor based on a quinoprotein alcohol dehydrogenase. Enzyme Microb. Technol. 5:383-388.
Direct 30-30® Blood Glucose Sensor (Markwell Medical) Catalog ©1990 ELCO Diagnostics Company [1 page].
Dixon et al. 2002. Characterization in vitro and in vivo of the oxygen dependence of an enzyme-polymer biosensor for monitoring brain glucose. Journal of Neuroscience Methods 119:135-142.
DuPont Dimension AR®. 1998. The chemistry analyzer that makes the most of your time money and effort. Catalog. Dade International Chemistry Systems. Newark DE [18 pages].
Durliat et al. 1976. Spectrophotometric and electrochemical determinations of L(+)-lactate in blood by use of lactate dehydrogenase from yeast. Clinical Chemistry 22(11):1802-1805.
Edwards Lifesciences 2000. Accuracy for your and your patients. Marketing materials [4 pages].
Ekinci et al. 2006. Preparation and Characterization of an Aromatic Polyimide and Its Use as a Selective Membrane for H2O2. Turk J Chem. 30:277-285.
El Degheidy et al. 1986. Optimization of an implantable coated wire glucose sensor. J. Biomedical Engineering 8:121-129.
El-Khatib et al. 2007. Adaptive closed-loop control provides blood-glucose regulation using dual subcutaneous insulin and glucagon infusion in diabetic swine. Journal of Diabetes Science and Technology 1(2):181-192.
El-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Analytical and Bioanalytical Chemistry 373:758-761.
Fahy et al. 2008. An analysis: hyperglycemic intensive care patients need continuous glucose monitoring-easier said than done. Journal of Diabetes Science and Technology 2(2):201-204.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technology & Therapeuticsr 5(5):769-779.

(56) References Cited

OTHER PUBLICATIONS

Fischer et al. 1987. Assessment of subcutaneous glucose concentration: validation of the wick technique as a reference for implanted electrochemical sensors in normal and diabetic dogs. Diabetologia 30:940-945.
Fischer et al. 1989. Oxygen Tension at the Subcutaneous Implantation Site of Glucose Sensors. Biomed. Biochem 11-12:965-972.
Fischer et al. 1995. Hypoglycaemia-warning by means of subcutaneous electrochemical glucose sensors: an animal study. Horm. Metab. Rese. 27:53.
Freedman et al. 1991. Statistics Second Edition W.W. Norton & Company p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diabetes Technology & Therapeutics 10:188-193.
Ganesan et al. 2005. Gold layer-based dual crosslinking procedure of glucose oxidase with ferrocene monocarboxylic acid provides a stable biosensor. Analytical Biochemistry 343:188-191.
Ganesh et al. 2008. Evaluation of the VIA® blood chemistry monitor for glucose in healthy and diabetic volunteers. Journal of Diabetes Science and Technology 2(2):182-193.
Gao et al. 1989. Determination of Interfacial parameters of cellulose acetate membrane materials by HPLC. J. Liquid Chromatography 12(11):2083-2092.
Garg et al. 2004. Improved Glucose Excursions Using an Implantable Real-Time continuous Glucose Sensor in Adults with Type I Diabetes. Diabetes Care 27:734-738.
Geller et al. 1997. Use of an immunoisolation device for cell transplantation and tumor immunotherapy. Ann NY Acad Sci 831:438-451.
Gerritsen et al. 1999. Performance of subcutaneously implanted glucose sensors for continuous monitoring. The Netherlands Journal of Medicine 54:167-179.
Gerritsen M. 2000. Problems associated with subcutaneously implanted glucose sensors. Diabetes Care 23(2):143-145.
Gilligan et al. 1994. Evaluation of a subcutaneous glucose sensor out to 3 months in a dog model. Diabetes Care 17(8):882-887.
Gilligan et al. 2004. Feasibility of continuous long-term glucose monitoring from a subcutaneous glucose sensor in humans. Diabetes Technology & Therapeutics 6:378-386.
Godsland et al. 2001. Maximizing the Success Rate of Minimal Model Insulin Sensitivity Measurement in Humans: The Importance of Basal Glucose Levels. The Biochemical Society and the Medical Research Society 101:1-9.
Gouda et al. 2003 Thermal inactivation of glucose oxidase. The Journal of Biological Chemistry 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gregg et al. 1990. Cross-Linked Redox Gels Containing Glucose Oxidase for Amperometric Biosensor Applications. Analytical Chemistry 62:258-263.
Gross et al. 2000. Performance evaluation of the MiniMed® continuous glucose monitoring system during patient home use. Diabetes Technology & Therapeutics 2(1):49-56.
Gross et al. 2000. Efficacy and reliability of the continuous glucose monitoring system. Diabetes Technology & Therapeutics 2(Suppl 1):S19-S26.
Guerci et al. 2003. Clinical performance of CGMS in type 1 diabetic patients treated by continuous subcutaneous insulin infusion using insulin analogs. Diabetes Care 26:582-589.

Guo et al. 1998. Modification of cellulose acetate ultrafiltration membrane by gamma ray radiation Shuichuli Jishi Bianji Weiyuanhui 23(6):315-318 (Abstract only).
Hall et al. 1998. Electrochemical oxidation of hydrogen peroxide at platinum electrodes. Part II: Effect of potential. Electrochimica Acta 43(14-15):2015-2024.
Hall et al. 1998. Electrochemical oxidation of hydrogen peroxide at platinum electrodes. Part 1: An adsorption-controlled mechanism. Electrochimica Acta 43(5-6):579-588.
Hall et al. 1999. Electrochemical oxidation of hydrogen peroxide at platinum electrodes. Part III: Effect of temperature. Electrochimica Acta 44:2455-2462.
Hall et al. 1999. Electrochemical oxidation of hydrogen peroxide at platinum electrodes. Part IV: Phosphate buffer dependence. Electrochimica Acta 44:4573-4582.
Hall et al. 2000. Electrochemical oxidation of hydrogen peroxide at platinum electrodes. Part V: Inhibition by chloride. Electrochimica Acta 45:3573-3579.
Hamilton Syringe Selection Guide. 2006. Syringe Selection www.hamiltoncompany.com.
Harrison et al. 1988. Characterization of perfluorosulfonic acid polymer coated enzyme electrodes and a miniaturized integrated potentiostat for glucose analysis in whole blood. Analytical Chemistry 60:2002-2007.
Hashiguchi et al. 1994. Development of a miniaturized glucose monitoring system by combining a needle-type glucose sensor with microdialysis sampling method: Long-term subcutaneous tissue glucose monitoring in ambulatory diabetic patients. Diabetes Care 17(5):387-396.
Heller 1990. Electrical wiring of redox enzymes. Acc. Chem. Res. 23:128-134.
Heller A. 1992. Electrical Connection of Enzyme Redox Centers to Electrodes. J. Phys. Chem. 96:3579-3587.
Heller A. 1999. Implanted electrochemical glucose sensors for the management of diabetes. Annu Rev Biomed Eng 1:153-175.
Heller A. 2003. Plugging metal connectors into enzymes. Nature Biotechnology 21:631-632.
Hicks 1985. In Situ Monitoring. Clinical Chemistry 31(12):1931-1935.
Hitchman M. L. 1978. Measurement of Dissolved Oxygen. In Elving et al. (Eds.). Chemical Analysis vol. 49 Chap. 3 pp. 34-49 and 59-123. New York: John Wiley & Sons.
Hoel Paul G. 1976. Elementary Statistics Fourth Edition. John Wiley & Sons Inc.. pp. 113-114.
Hrapovic et al. 2003. Picoamperometric detection of glucose at ultrasmall platinum-based biosensors: preparation and characterization. Analytical Chemistry 75:3308-3315.
http:--www.merriam-webster.com-dictionary definition for "aberrant" Aug. 8-19, 2008 p. 1.
Hu et al. 1993. A needle-type enzyme-based lactate sensor for in vivo monitoring. Analytica Chimica Acta 281:503-511.
Huang et al. Aug. 1975. Electrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Electrode. U.S. Department of Commerce-NTIS pp. 1-116.
Huang et al. Sep. 1997. A 0.5mW Passive Telemetry IC for Biomedical Applications Proceedings of the 23rd European Solid-State Circuits Conference (ESSCIRC '97) pp. 172-175 Southampton UK.
Hunter et al. Mar. 31 2000. Minimally Invasive Glucose Sensor and Insulin Delivery System. MIT Home Automation and Healthcare Consortium. Progress Report No. 2-5 [17 pages].
Ishikawa et al. 1998. Initial evaluation of a 290-mm diameter subcutaneous glucose sensor: Glucose monitoring with a biocompatible flexible-wire enzyme-based amperometric microsensor in diabetic and nondiabetic humans. Journal of Diabetes and Its Complications 12:295-301.
ISP Corporation [Ashland Inc.] "PVP (Polyvinylpyrrolidone)" http:--online1 .ispcorp.com-Brochures-Performance%20Chemicals-PVP.pdf; accessed Jun. 18, 2013; pp. 13.
Jaffari et al. 1995. Recent advances in amperometric glucose biosensors for in vivo monitoring. Physiol. Meas. 16: 1-15.

(56) References Cited

OTHER PUBLICATIONS

Jensen et al. 1997. Fast wave forms for pulsed electrochemical detection of glucose by incorporation of reductive desorption of oxidation products. Analytical Chemistry 69(9):1776-1781.
Jeutter D. C. 1982. A transcutaneous implanted battery recharging and biotelemeter power switching system. IEEE Transactions in Biomedical Engineering (BME) 29:314-321.
Jobst et al. 1996. Thin-Film Microbiosensors for Glucose-Lactate Monitoring. Analytical Chemistry 8(18):3173-3179.
Johnson 1991. Reproducible electrodeposition of biomolecules for the fabrication of miniature electroenzymatic biosensors. Sensors and Actuators B 5:85-89.
Johnson et al. 1992. In vivo evaluation of an electroenzymatic glucose sensor implanted in subcutaneous tissue. Biosensors & Bioelectronics 7:709-714.
Jovanovic L. 2000. The role of continuous glucose monitoring in gestational diabetes mellitus. Diabetes Technology & Therapeutics 2(Suppl 1):S67-S71.
Kacaniklic May-Jun. 1994. Electroanalysis 6(5-6):381-390.
Kamath et al. 2008. Calibration of a continuous glucose monitor: effect of glucose rate of change. Eighth Annual Diabetes Technology Meeting Nov. 13-15, 2008 p. A88.
Kang et al. 2003. In vitro and short-term in vivo characteristics of a Kel-F thin film modified glucose sensor. Analytical Science 19:1481-1486.
Kargol et al. 2001. Studies on the structural properties of porous membranes: measurement of linear dimensions of solutes. Biophys Chem 91:263-271.
Karube et al. 1993. Microbiosensors for acetylcholine and glucose. Biosensors & Bioelectronics 8:219-228.
Kaufman et al. 2001. A pilot study of the continuous glucose monitoring system. Diabetes Care 24(12):2030-2034.
Kaufman. 2000. Role of the continuous glucose monitoring system in pediatric patients. Diabetes Technology & Therapeutics 2(1):S49-S52.
Kawagoe et al. 1991. Enzyme-modified organic conducting salt microelectrode. Analytical Chemistry 63:2961-2965.
Keedy et al. 1991. Determination of urate in undiluted whole blood by enzyme electrode. Biosensors & Bioelectronics 6:491-499.
Kerner et al. 1988. A potentially implantable enzyme electrode for amperometric measurement of glucose. Horm Metab Res Suppl. 20:8-13.
Kerner et al. 1993. The function of a hydrogen peroxide-detecting electroenzymatic glucose electrode is markedly impaired in human sub-cutaneous tissue and plasma. Biosensors & Bioelectronics 8:473-482.
Kiechle F.L. 2001. The impact of continuous glucose monitoring on hospital point-of-care testing programs. Diabetes Technology & Therapeutics 3:647-649.
Klueh et al. 2003. Use of Vascular Endothelia Cell Growth Factor Gene Transfer to Enhance Implantable Sensor Function in Vivo. J. Biomedical Materials Research 67A:1072-1086.
Klueh et al. 2007. Inflammation and glucose sensors: use of dexamethasone to extend glucose sensor function and life span in vivo. Journal of Diabetes Science and Technology 1 (4):496-504.
Kondo et al. 1982. A miniature glucose sensor implantable in the blood stream. Diabetes Care. 5(3):218-221.
Koschinsky et al. 1988. New approach to technical and clinical evaluation of devices for self-monitoring of blood glucose. Diabetes Care 11 (8): 619-619.
Koschinsky et al. 2001. Sensors for glucose monitoring: Technical and clinical aspects. Diabetes Metab. Res. Rev. 17:113-123.
Kost et al. 1985. Glucose-sensitive membranes containing glucose oxidase: activitiy swelling and permeability studies. Journal of Biomedical Materials Research 19:1117-1133.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Kraver et al. 2001. A mixed-signal sensor interface microinstrument. Sensors and Actuators A 91:266-277.
Kruger et al. 2000. Psychological motivation and patient education: A role for continuous glucose monitoring. Diabetes Technology & Therapeutics 2(Suppl 1):S93-S97.
Kulys et al. 1994. Carbon-paste biosensors array for long-term glucose measurement. Biosensors & Bioelectronics 9:491-500.
Kunjan et al. 2008. Automated blood sampling and glucose sensing in critical care settings. Journal of Diabetes Science and Technology 2(3):194-200.
Kunzler et al. 1993. Hydrogels based on hydrophilic side chain siloxanes. Poly Mat Sci and Eng 69:226-227.
Kunzler et al. 1995. Contact lens materials. Chemistry & Industry Aug. 21, 1995 pp. 651-655.
Kurtz et al. 2005. Recommendations for blood pressure measurement in humans and experimental animals Part 2: Blood pressure measurement in experimental animals a statement for professionals from the subcommittee of professional and public education of the American Heart Association Council on High Blood Pressure Research. Hypertension 45:299-310.
Ladd et al. 1996. Structure Determination by X-ray Crystallography 3rd ed. Plenum 1996 Ch. 1 pp. xxi-xxiv and 1-58.
Lee et al. 1999. Effects of pore size void volume and pore connectivity on tissue responses. Society for Biomaterials 25th Annual Meeting p. 171 [one page].
Lehmann et al. May 1994. Retrospective validation of a physiological model of glucose-iunsulin interaaction in tyhpe 1 diabetes mellitus. Med. Eng. Phys. 16:193-202.
Lerner et al. 1984. An implantable electrochemical glucose sensor. Ann. N. Y. Acad. Sci. 428:263-278.
Lewandowski et al. 1988. Evaluation of a miniature blood glucose sensor. Trans Am Soc Artif Intern Organs 34:255-258.
Leypoldt et al. 1984. Model of a two-substrate enzyme electrode for glucose. Analytical Chemistry 56:2896-2904.
Linke et al. 1994. Amperometric biosensor for in vivo glucose sensing based on glucose oxidase immobilized in a redox hydrogel. Biosensors & Bioelectronics 9:151-158.
Loffler et al. 1995. Separation and determination of traces of ammonia in air by means of chromatomembrane cells. Fresenius J Analytical Chemistry 352:613-614.
Lowe 1984. Biosensors. Trends in Biotechnology 2(3)59-65.
Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.
Lyandres et al. 2008. Progress toward an in vivo surface-enhanced raman spectroscopy glucose sensor. Diabetes Technology & Therapeutics 10(4):257-265.
Lyman D. 1960. Polyurethanes. I. The Solution Polymerization of Diisocyanates with Ethylene Glycol. J. Polymer Sci XLV:45:49.
Madaras et al. 1996. Microfabricated amperometric creatine and creatinine biosensors. Analytica Chimica Acta 319:335-345.
Maidan et al. 1992. Elimination of Electrooxidizable Interferant-Produced Currents in Amperometric Biosensors. Analytical Chemistry 64:2889-2896.
Makale et al. 2003. Tissue window chamber system for validation of implanted oxygen sensors. Am. J. Physiol. Heart Circ. Physiol. 284:H2288-2294.
Malin et al. 1999. Noninvasive Prediction of Glucose by Near-Infrared Diffuse Reflectance Spectroscopy. Clinical Chemistry 45(9):1651-1658.
Maran et al. 2002. Continuous subcutaneous glucose monitoring in diabetic patients: A multicenter analysis. Diabetes Care 25(2):347-352.
March W. F. 2002. Dealing with the delay. Diabetes Technology & Therapeutics 4(1):49-50.
Marena et al. 1993. The artificial endocrine pancreas in clinical practice and research. Panminerva Medica 35(2):67-74.
Mascini et al. 1989. Glucose electrochemical probe with extended linearity for whole blood. J Pharm Biomed Anal 7(12): 1507-1512.

(56) References Cited

OTHER PUBLICATIONS

Mastrototaro et al. 1991. An electroenzymatic glucose sensor fabricated on a flexible substrate. Sensors and Actuators B 5:139-144.
Mastrototaro et al. 2003. Reproducibility of the continuous glucose monitoring system matches previous reports and the intended use of the product. Diabetes Care 26:256; author reply p. 257.
Mastrototaro J. J. 2000. The MiniMed continuous glucose monitoring system. Diabetes Technology & Therapeutics 2(Suppl 1):S13-S18.
Matsumoto et al. 1998. A micro-planar amperometeric glucose sensor unsusceptible to interference species. Sensors and Actuators B 49:68-72.
Matsumoto et al. 2001. A long-term lifetime amperometric glucose sensor with a perfluorocarbon polymer coating. Biosensors & Bioelectronics 16:271-276.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diabetes Technology & Therapeutics 10:149-159.
McCartney et al. 2001. Near-infrared fluorescence lifetime assay for serum glucose based on allophycocyanin-labeled concanavalin A. Anal Biochem 292:216-221.
McGrath et al. 1995. The use of differential measurements with a glucose biosensor for interference compensation during glucose determinations by flow injection analysis. Biosensors & Bioelectronics 10:937-943.
McKean et al. Jul. 7, 1988. A Telemetry Instrumentation System for Chronically Implanted Glucose and Oxygen Sensors. Transactions on Biomedical Engineering 35:526-532.
MDDI "Thermoplastic Silicone-Urethane Copolymers: A New Class of Biomedical Elastomers" http:--www.mddionline.com accessed Jul. 1, 2013 pp. 9.
Medical Device & Diagnostic Industry Apr. 1, 2000. Thermoplastic Silicone-Urethane Copolymers: A new Class of Biomedical Elastomers, Printed from http:--www.middionline.com-print-112r.
Memoli et al. 2002. A comparison between different immobilised glucoseoxidase-based electrodes. J Pharm Biomed Anal 29:1045-1052.
Merriam-Webster Online Dictionary. Apr. 23, 2007. Definition of "nominal". http:--www.merriam-webster.com-dictionary-nominal.
Merriam-Webster Online Dictionary. Definition of "acceleration". http:--www.merriam-webster.com-dictionary-Acceleration Jan. 11, 2010.
Merriam-Webster Online Dictionary. Definition of "system". http:--www.merriam-webster.com-dictionary-System Jan. 11, 2010.
Meyerhoff et al. 1992. On line continuous monitoring of subcutaneous tissue glucose in men by combining portable glucosensor with microdialysis. Diabetologia 35:1087-1092.
Miller et al. 1989. Generation of IL1-like activity in response to biomedical polymer implants: a comparison of in vitro and in vivo models. J Biomed Mater Res 23:1007-1026.
Miller et al. 1989. In vitro stimulation of fibroblast activity by factors generated from human monocytes activated by biomedical polymers. Journal of J Biomed Mater Res 23:911-930.
Miller A. 1988. Human monocyte-macrophage activation and interleukin 1 generation by biomedical polymers. J Biomed Mater Res 23:713-731.
Moatti-Sirat et al. 1992. Evaluating in vitro and in vivo the interference of ascorbate and acetaminophen on glucose detection by a needle-type glucose sensor. Biosensors & Bioelectronics 7:345-352.
Moatti-Sirat et al. 1992. Towards continuous glucose monitoring: in vivo evaluation of a miniaturized glucose sensor implanted for several days in rat subcutaneous tissue. Diabetologia 35:224-230.
Moatti-Sirat et al. 1994. Reduction of acetaminophen interference in glucose sensors by a composite Nafion membrane: demonstration in rats and man. Diabetologia 37(6):610-616.

Morff et al. 1990. Microfabrication of reproducible economical electroenzymatic glucose sensors. Annual International Conference of the IEEE Engineering in Medicine and Biology Society 12(2):0483-0484.
Mosbach et al. 1975. Determination of heat changes in the proximity of immobilized enzymes with an enzyme termistor and its use for the assay of metabolites. Biochim. Biophys. Acta. (Enzymology) 403:256-265.
Motonaka et al. 1993. Determination of cholesterol and cholesterol ester with novel enzyme microsensors. Analytical Chemistry 65:3258-3261.
Moussy et al. 1993. Performance of subcutaneously implanted needle-type glucose sensors employing a novel trilayer coating. Analytical Chemistry 85: 2072-2077.
Moussy et al. 2000. Biomaterials community examines biosensor biocompatibility. Diabetes Technology & Therapeutics 2:473-477.
Moussy Francis 2002. Implantable Glucose Sensor: Progress and Problems. Sensors 1:270-273.
Mowery et al. 2000. Preparation and characterization of hydrophobic polymeric films that are thromboresistant via nitric oxide release. Biomaterials 21:9-21.
Murphy et al. 1992. Polymer membranes in clinical sensor applications. II. The design and fabrication of permselective hydrogels for electrochemical devices. Biomaterials 13(14):979-990.
Muslu. 1991. Trickling filter performance. Applied Biochemistry and Biotechnology 37:211-224.
Myler et al. 2002. Ultra-thin-polysiloxane-film-composite membranes for the optimisation of amperometric oxidase enzyme electrodes. Biosensors & Bioelectronics 17:35-43.
Nakayama et al. 1992. Surface fixation of hydrogels: heparin and glucose oxidase hydrogelated surfaces. ASAIO Journal M421-M424.
Nam et al. 2000. A novel fabrication method of macroporous biodegradable polymer scaffolds using gas foaming salt as a porogen additive. J Biomed Mater Res 53:1-7.
Nation® 117 Solution Product Description Product No. 70160 Sigma-Aldrich Corp. St. Louis MO. Downloaded from https:--www.signaaldrich.com-cgi- bin-hsrun-Suite7-Suite-HAHTpage-Suite.HsExternal Prod . . . on Apr. 7, 2005.
Ohara et al. 1994. "Wired" enzyme electrodes for amperometric determination of glucose or lactate in the presence of interfering substances. Analytical Chemistry 66:2451-2457.
Ohara et al. December 1993. Glucose electrodes based on cross-linked bis(22'-bipyridine)chloroosmium(+−2+) complexed poly(l-vinylimidazole) films. Analytical Chemistry 65:3512-3517.
Okuda et al. 1971. Mutarotase effect on micro determinations of D-glucose and its anomers with p-D-glucose oxidase. Anal Biochem 43:312-315.
Oxford English Dictionary Online. Definition of "impending". http:--www.askoxford.com-results-?view=dev dict&field-12668446 Impending&branch= Jan. 11, 2010.
Palmisano et al. 2000. Simultaneous monitoring of glucose and lactate by an interference and cross-talk free dual electrode amperometric biosensor based on electropolymerized thin films. Biosensors & Bioelectronics 15:531-539.
Panetti 2002. Differential effects of sphingosine 1-phosphate and lysophosphatidic acid on endothelial cells. Biochimica et Biophysica Acta 1582:190-196.
Park et al. 2002. Gas separation properties of polysiloxane-polyether mixed soft segment urethane urea membranes. J. Membrane Science 204: 257-269.
Patel et al. 2003. Amperometric glucose sensors based on ferrocene containing polymeric electron transfer systems—a preliminary report. Biosensors & Bioelectronics 18:1073-1076.
Peacock et al. 2008. Cardiac troponin and outcome in acute heart failure. N. Engl. J. Med. 358:2117-2126.
Pegoraro et al. 1995. Gas transport properties of siloxane polyurethanes. Journal of Applied Polymer Science 57:421-429.
Pfeiffer et al. 1992. On line continuous monitoring of subcutaneous tissue glucose is feasible by combining portable glucosensor with microdialysis. Horm. Metab. Res. 25:121-124.
Pfeiffer E.F. 1990. The glucose sensor: the missing link in diabetes therapy. Horm Metab Res Suppl. 24:154-164.

(56) References Cited

OTHER PUBLICATIONS

Phillips and Smith. 1988. Biomedical Applications of Polyurethanes: Implications of Failure Mechanisms. J. Biomat. Appl. 3:202-227.
Pichert et al. 2000. Issues for the coming age of continuous glucose monitoring. Diabetes Educator 26(6):969-980.
Pickup et al. 1987-88. Implantable glucose sensors: choosing the appropriate sensing strategy. Biosensors 3:335-346.
Pickup et al. 1988. Progress towards in vivo glucose sensing with a ferrocene-mediated amperometric enzyme electrode. pp. 34-36.
Pickup et al. 1989. Potentially-implantable amperometric glucose sensors with mediated electron transfer: improving the operating stability. Biosensors 4:109-119.
Pickup et al. 1993. Developing glucose sensors for in vivo use. Elsevier Science Publishers Ltd (UK) TIBTECH vol. 11: 285-291.
Pickup et al. 2989. In vivo molecular sensing in diabetes mellitus: an implantable glucose sensor with direct electron transfer. Diabetologia 32:213-217.
Pineda et al. 1996. Bone regeneration with resorbable polymeric membranes. III. Effect of poly(L-lactide) membrane pore size on the bone healing process in large defects. J. Biomedical Materials Research 31:385-394.
Pinner et al. 1959. Cross-linking of celluose acetate by ionizing radiation. Nature 184:1303-1304.
Pishko et al. 1991. Amperometric glucose microelectrodes prepared through immobilization of glucose oxidase in redox hydrogels. Analytical Chemistry 63:2268-72.
Pitzer et al. 2001. Detection of hypoglycemia with the GlucoWatch biographer. Diabetes Care 24(5):881-885.
Poitout et al. 1991. In Vitro and In Vivo Evaluation in Dogs of a Miniaturized Glucose Sensor. ASAIO Transactions 37:M298-M300.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxice at a platinum disc electrode. Electrochemica Acta 26(6):725-729.
Quinn et al. 1995. Kinetics of glucose delivery to subcutaneous tissue in rats measured with 0.3-mm amperometric microsensors. The American Physiological Society E155-E161.
Quinn et al. 1997. Biocompatible glucose-permeable hydrogel for in situ coating of implantable biosensors. Biomaterials 18:1665-1670.
Rabah et al. 1991. Electrochemical wear of graphite anodes during electrolysis of brine. Carbon 29(2): 165-171.
Ratner B.D. 2002. Reducing capsular thickness and enhancing angiogenesis around implant drug release systems. J Control Release 78:211-218.
Reach et al. 1986. A Method for Evaluating in vivo the Functional Characteristics of Glucose Sensors. Biosensors 2:211-220.
Reach et al. 1992. Can continuous glucose monitoring be used for the treatment of diabetes? Analytical Chemistry 64(5):381-386.
Reach G. 2001. Which threshold to detect hypoglycemia? Value of receiver-operator curve analysis to find a compromise between sensitivity and specificity. Diabetes Care 24(5):803-804.
Reach Gerard. 2001. Letters to the Editor Re: Diabetes Technology & Therapeutics 2000 2:49-56. Diabetes Technology & Therapeutics 3(1):129-130.
Rebrin et al. 1989. Automated feedback control of subcutaneous glucose concentration in diabetic dogs. Diabetologia 32:573-576.
Rebrin et al. 1992. Subcutaneous glucose monitoring by means of electrochemical sensors: fiction or reality? J. Biomed. Eng. 14:33-40.
Reusch. 2004. Chemical Reactivity. Organometallic Compounds. Virtual Textbook of Organic Chem. pp. 1-16 http:--www.cem.msu.edu-~reusch-VirtualText-orgmetal.htm.
Rhodes et al. 1994. Prediction of pocket-portable and implantable glucose enzyme electrode performance from combined species permeability and digital simulation analysis. Analytical Chemistry 66(9):1520-1529.
Rigla et al. 2008. Real-time continuous glucose monitoring together with telemedical assistance improves glycemic control and glucose stability in pump-treated patients. Diabetes. Technology & Therapeutics 10:194-199.
Rivers et al. 2001. Central venous oxygen saturation monitoring in the critically ill patient. Current Opinion in Critical Care 7:204-211.
Sachlos et al. 2003. Making Tissue Engineering Scaffolds Work. Review on the Application of Sold Freeform Fabrication Technology to the Production of Tissue Engineering Scaffolds. European Cells and Materials 5:29-40.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Sakakida et al. 1993. Ferrocene-Mediated Needle Type Glucose Sensor Covered with Newly Designed Biocompatible Membrane. Sensors and Actuators B 13-14:319-322.
Salardi et al. 2002. The glucose area under the profiles obtained with continuous glucose monitoring system relationships with HbA1c in pediatric type 1 diabetic patients. Diabetes Care 25(10):1840-1844.
Samuels M.P. 2004. The effects of flight and altitude. Arch Dis Child. 89: 448-455.
San Diego Plastics Inc. 2009. Polyethylene Data Sheet http:--www.sdplastics.com-polyeth.html.
Sanders et al. 2003. Fibrous Encapsulation of Single Polymer Microfibers Depends on their Vertical Dimension in subcutaneous Tissue. J. Biomedical Research Materials 67A:1181-1187.
Sansen et al. 1985. Glucose sensor with telemetry system. In Ko W. H. (Ed.). Implantable Sensors for Closed Loop Prosthetic Systems. Chap. 12 pp. 167-175 Mount Kisco NY: Future Publishing Co.
Sansen et al. 1990. A smart sensor for the voltammetric measurement of oxygen or glucose concentrations. Sensors and Actuators B 1:298-302.
Schmidt et al. 1993. Glucose concentration in subcutaneous extracellular space. Diabetes Care 16(5):695-700.
Schmidtke et al. 1998. Measurement and modeling of the transient difference between blood and subcutaneous glucose concentrations in the rat after injection of insulin. Proc Natl Acad Sci U S A 95:294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990. Development of a potentially wearable glucose sensor for patients with diabetes mellitus: design and in-vitro evaluation. Biosensors & Bioelectronics 5:37-46.
Schuler et al. 1999. Modified gas-permeable silicone rubber membranes for covalent immobilisation of enzymes and their use in biosensor development. Analyst 124:1181-1184.
Selam J. L. 1997. Management of diabetes with glucose sensors and implantable insulin pumps. From the dream of the 60s to the realities of the 90s. ASAIO J. 43:137-142.
Service et al. 1970. Mean amplitude of glycemic excursions a measure of diabetic instability. Diabetes 19:644-655.
Service et al. 1987. Measurements of glucose control. Diabetes Care 10: 225-237.
Service R. F. 2002. Can sensors make a home in the body? Science 297:962-963.
Sharkawy et al. 1996. Engineering the tissue which encapsulates subcutaneous implants. I. Diffusion properties. J Biomed Mater Res 37:401-412.
Shaw et al. 1991. In vitro testing of a simply constructed highly stable glucose sensor suitable for implantation in diabetic patients. Biosensors & Bioelectronics 6:401-406.
Shichiri et al. 1982. Wearable artificial endocrine pancreas with needle-type glucose sensor. Lancet 2:1129-1131.

(56) References Cited

OTHER PUBLICATIONS

Shichiri et al. 1983. Glycaemic Control in Pancreatectomized Dogs with a Wearable Artificial Endocrine Pancreas. Diabetologia 24:179-184.
Shichiri et al. 1985. Needle-type Glucose Sensor for Wearable Artificial Endocrine Pancreas in Implantable Sensors for Closed-Loop Prosthetic Systems Ed. Ko Futura Pub. Co. Inc. Mt. Kisco NY Chapter 15:197-210.
Shichiri et al. 1986. Telemetry Glucose Monitoring Device with Needle-Type Glucose Sensor: A Useful Tool for Blood Glucose Monitoring in Diabetic Individuals. Diabetic Care 9(3):298-301.
Shichiri et al. 1989. Membrane Design for Extending the Long-Life of an Implantable Glucose Sensor. Diab. Nutr. Metab. 2:309-313.
Shults et al. 1994. A telemetry-instrumentation system for monitoring multiple subcutaneously implanted glucose sensors. IEEE Transactions on Biomedical Engineering (BME) 41(10):937-942.
Sieminski et al. 2000. Biomaterial-microvasculature interactions. Biomaterials 21:2233-2241.
Skyler J. S. 2000. The economic burden of diabetes and the benefits of improved glycemic control: The potential role of a continuous glucose monitoring system. Diabetes Technology & Therapeutics 2(Suppl 1):S7-S12.
Slater-Maclean et al. 2008. Accuracy of glycemic measurements in the critically ill. Diab. Technology & Therapeutics 10:169-177.
Smith et al. 1991. A Comparison of Islet Transplantation and Subcutaneous Insulin Injections for the Treatment of Diabetes Mellitus. Comput Biol Med. 21(6):417-427.
Sokol et al. 1980. Immobilized-enzyme rate-determination method of glucose analysis. Clinical Chemistry 26(1):89-92.
Sriyudthsak et al. 1996. Enzyme-epoxy membrane based glucose analyzing system and medical applications. Biosensors & Bioelectronics 11:735-742.
Steil et al. 2003. Determination of plasma glucose during rapid glucose excursions with a subcutaneous glucose sensor. Diabetes Technology & Therapeutics 5(1):27-31.
Stern et al. 1957. Electrochemical polarization: 1. A theoretical analysis of the shape of polarization curves. Journal of the Electrochemical Society 104(1):56-63.
Sternberg et al. 1988. Covalent enzyme coupling on cellulose acetate membranes for glucose sensor development. Analytical Chemistry 69:2781-2786.
Sternberg et al. 1988. Study and Development of Multilayer Needle-type Enzyme-based Glucose Microsensors. Biosensors 4:27-40.
Stokes. 1988. Polyether Polyurethanes: Biostable or Not? J. Biomat. Appl. 3:228-259.
Street et al. Dec. 2004. Islet Graft Assessment in the Edmonton Protocol: Implications for Predicting Long-Term Clinical Outcome. Diabetes 53: 3107-3114.
Suh et al. 2002. Behavior of fibroblasts on a porous hyaluronic acid incorporated collagen matrix. Yonsei Medical Journal 43(2):193-202.
Sumino T. et al. 1998. Preliminary study of continuous glucose monitoring with a microdialysis technique. Proceedings of the IEEE 20(4):1775-1778.
Takegami et al. 1992. Pervaporation of ethanol water mixtures using novel hydrophobic membranes containing polydimethylsiloxane. Journal of Membrane Science 75:93-105.
Tanenberg et al. 2000. Continuous glucose monitoring system: A new approach to the diagnosis of diabetic gastroparesis. Diabetes Technology & Therapeutics 2(Suppl 1):S73-S80.
Tang et al. 1993. Fibrin(ogen) mediates acute inflammatory responses to biomaterials. J Exp Med 178:2147-2156.
Tang et al. 1995. Inflammatory responses to biomaterials. Am J Clin Pathol 103:466-471.
Tang et al. 1996. Molecular determinants of acute inflammatory responses to biomaterials. J Clin Invest 97:1329-1334.
Tang et al. 1998. Mast cells mediate acute inflammatory responses to implanted biomaterials. Proc Natl Acad Sci U S A 95:8841-8846.
Tatsuma et al. 1991. Oxidase-peroxidase bilayer-modified electrodes as sensors for lactate pyruvate cholesterol and uric acid. Analytica Chimica Acta 242:85-89.
Thome et al. 1995. Abstract—Can the decrease in subcutaneous glucose concentration precede the decrease in blood glucose level? Proposition for a push-pull kinetics hypothesis. Horm. Metab. Res. 27:53.
Thome-Duret et al. 1996. Modification of the sensitivity of glucose sensor implanted into subcutaneous tissue. Diabetes Metabolism 22:174-178.
Thome-Duret et al. 1996. Use of a subcutaneous glucose sensor to detect decreases in glucose concentration prior to observation in blood. Analytical Chemistry 68:3822-3826.
Thome-Duret et al. 1998. Continuous glucose monitoring in the free-moving rat. Metabolism 47:799-803.
Thompson et al. 1986. In Vivo Probes: Problems and Perspectives. Department of Chemistry University of Toronto Canada pp. 255-261.
Tibell et al. 2001. Survival of macroencapsulated allogeneic parathyroid tissue one year after transplantation in nonimmunosuppressed humans. Cell Transplant 10:591-599.
Tierney et al. 2000. Effect of acetaminophen on the accuracy of glucose measurements obtained with the GlucoWatch biographer. Diabetes Technology & Therapeutics 2:199-207.
Tierney et al. 2000. The GlucoWatch® biographer: A frequent automatic and noninvasive glucose monitor. Ann. Med. 32:632-641.
Torjman et al. 2008. Glucose monitoring in acute care: technologies on the horizon. Journal of Diabetes Science and Technology 2(2):178-181.
Trecroci D. 2002. A Glimpse into the Future—Continuous Monitoring of Glucose with a Microfiber. Diabetes Interview Jul. 2002 pp. 42-43.
Tse and Gough. 1987. Time-Dependent Inactivation of Immobilized Glucose Oxidase and Catalase. Biotechnol. Bioeng. 29:705-713.
Turner and Pickup 1985. Diabetes mellitus: biosensors for research and management. Biosensors 1:85-115.
Turner et al. 1984. Carbon Monoxide: Acceptor Oxidoreductase from Pseudomonas Thermocarboxydovorans Strain C2 and its use in a Carbon Monoxide Sensor. Analytica Chimica Acta 163: 161-174.
Turner A.P.F. 1988. Amperometric biosensor based on mediator-modified electrodes. Methods in Enzymology 137:90-103.
Unger et al. 2004. Glucose control in the hospitalized patient. Emerg Med 36(9):12-18.
Updike et al. 1967. The enzyme electrode. Nature 214:986-988.
Updike et al. 1988. Laboratory Evaluation of New Reusable Blood Glucose Sensor. Diabetes Care 11:801-807.
Updike et al. 1994. Enzymatic glucose sensor: Improved long-term performance in vitro and in vivo. ASAIO Journal 40(2):157-163.
Updike et al. 1997. Principles of long-term fully implanted sensors with emphasis on radiotelemetric monitoring of blood glucose form inside a subcutaneous foreign body capsule (FBC). In Fraser ed. Biosensors in the Body. New York. John Wiley & Sons.
Updike et al. 2000. A subcutaneous glucose sensor with improved longevity dynamic range and stability of calibration. Diabetes Care 23(2):208-214.
Utah Medical Products Inc. 2003. Blood Pressure Transducers product specifications. Downloaded from http:--www.utahmed.com-deltran.htm on Sep. 7, 2006 [6 pages].
Vadgama P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C Math and Phys. Sci. 226:359-377.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
Velho et al. 1989. Strategies for calibrating a subcutaneous glucose sensor. Biomed Biochim Acta 48(11-12):957-964.
von Woedtke et al. 1989. In situ calibration of implanted electrochemical glucose sensors. Biomed Biochim. Acta 48(11-12):943-952.

(56) References Cited

OTHER PUBLICATIONS

Wade Jr. L.G. Organic Chemistry Chapter 17 Reactions of Aromatic Compounds pp. 762-7631987.
Wagner et al. 1998. Continuous amperometric monitoring of glucose in a brittle diabetic chimpanzee with a miniature subcutaneous electrode. Proc. Natl. Acad. Sci. A 95:6379-6382.
Wang et al. 1994. Highly Selective Membrane-Free Mediator-Free Glucose Biosensor. Analytical Chemistry 66:3600-3603.
Wang et al. 1997. Improved ruggedness for membrane-based amperometric sensors using a pulsed amperometric method. Analytical Chemistry 69:4482-4489.
Wang J. 2007. Electrochemical Glucose Biosensors. American Chemical Society Chemical Reviews Published on Web Dec. 23, 2007 page est. 11.1 pp. 1-12; 10.1021-cr068123a.
Ward et al. 2000. Rise in background current overtime in a subcutaneous glucose sensor in the rabbit: Relevance to calibration and accuracy. Biosensors & Bioelectronics 15:53-61.
Ward et al. 2000. Understanding Spontaneous Output Fluctuations of an Amperometric Glucose Sensor: Effect of Inhalation Anesthesia and e of a Nonenzyme Containing Electrode. ASAIO Journal 46:540-546.
Ward et al. 2002. A new amperometric glucose microsensor: In vitro and short-term in vivo evaluation. Biosensors & Bioelectronics 17:181-189.
Ward et al. 2004. A wire-based dual-analyte sensor for Glucose and Lactate: In Vitro and In Vivo Evaluation. Diabetes Technology & Therapeutics 6(3): 389-401.
Wientjes K. J. C. 2000. Development of a glucose sensor for diabetic patients (Ph.D. Thesis).
Wikipedia 2006. "Intravenous therapy" http:--en.wikipedia.org-wiki-Intravenous_therapy Aug. 15, 2006 [6 pages].
Wiley Electrical and Electronics Engineering Dictionary. 2004. John Wiley & Sons Inc. pp. 141142 548 549.
Wilkins et al. 1988. The coated wire electrode glucose sensor. Horm Metab Res Suppl. 20:50-55.
Wilkins et al. 1995. Integrated implantable device for long-term glucose monitoring. Biosensors & Bioelectronics 10:485-494.
Wilkins et al. 1996. Glucose monitoring: state of the art and future possibilities. Med Eng Phys 18:273-288.
Wilson et al. 1992. Progress toward the development of an implantable sensor for glucose. Clinical Chemistry 38(9):1613-1617.
Wilson et al. 2000. Enzyme-based biosensors for in vivo measurements. Chem. Rev. 100:2693-2704.
Wilson R.; 1992. Review Article: Glucose oxidase: an ideal enzyme. Biosensors & Bioelectronics. 7:165-185.
Wood W. et al. March 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Worsley et al. 2008. Measurement of glucose in blood with a phenylboronic acid optical sensor. Journal of Diabetes Science and Technology 2(2):213-220.
Wright et al. 1999. Bioelectrochemical dehalogenations via direct electrochemistry of poly(ethylene oxide)-modified myoglobin. Electrochemistry Communications 1:603- 611.
Wu et al. 1999. In situ electrochemical oxygen generation with an immunoisolation device. Annals New York Academy of Sciences pp. 105-125.
Yamasaki et al. 1989. Direct measurement of whole blood glucose by a needle-type sensor. Clinica Chimica Acta. 93:93-98.
Yamasaki Yoshimitsu Sep. 1984. The development of a needle-type glucose sensor for wearable artificial endocrine pancreas. Medical Journal of Osaka University 35(1-2):25-34.
Yang et al. 1998. Development of needle-type glucose sensor with high selectivity. Science and Actuators B 46:249-256.
Yang et al. 2004. A Comparison of Physical Properties and Fuel Cell Performance of Nafion and Zirconium Phosphate-Nafion Composite Membranes. Journal of Membrane Science 237:145-161.
Yang et al. 1996. A glucose biosensor based on an oxygen electrode: In-vitro performances in a model buffer solution and in blood plasma. Biomedical Instrumentation & Technology 30:55-61.
Ye et al. 1993. High Current Density 'Wired' Quinoprotein Glucose Dehydrogenase Electrode. Analytical Chemistry 65:238-241.
Zamzow et al. 1990. Development and evaluation of a wearable blood glucose monitor. ASAIO Transactions 36(3):M588-M591.
Zethelius et al. 2008. Use of multiple biomarkers to improve the prediction of death from cardiovascular causes. N. Engl. J. Med. 358: 2107-2116.
Zhang et al 1993. Electrochemical oxidation of H202 on Pt and Pt + Ir electrodes in physiological buffer and its applicability to H202-based biosensors. J. ElectroAnalytical Chemistry 345:253-271.
Zhang et al. 1994. Elimination of the acetaminophen interference in an implantable glucose sensor. Analytical Chemistry 66(7): 1183-1188.
Zhu et al. 1994. Fabrication and characterization of glucose sensors based on a microarray H202 electrode. Biosensors & Bioelectronics 9: 295-300.
Zhu et al. 2002. Planar amperometric glucose sensor based on glucose oxidase immobilized by chitosan film on prussian blue layer. Sensors 2:127-136.
EP 097236772: Extended European Search Report dated Jul. 21, 2014 and Applicant Resposne filed Feb. 17, 2015.
PCT-US2009-038678 filed Mar. 27, 2009: International Preliminary Report on Patentability dated Oct. 7, 2010.
PCT-US2009-038678 filed Mar. 27, 2009: International Search Report and Written Opinion dated Jul. 7, 2009.
U.S. Appl. No. 12/628,095, filed Nov. 30, 2009: Office Action dated Nov. 13, 2012.

\* cited by examiner

POLYMER MEMBRANES FOR CONTINUOUS ANALYTE SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 14/517,663 filed Oct. 17, 2014, which is a continuation of U.S. application Ser. No. 14/058,154, filed Oct. 18, 2013, now U.S. Pat. No. 8,954,128, which is a continuation of U.S. application Ser. No. 12/718,299, filed Mar. 5, 2010, now U.S. Pat. No. 8,583,204, which is a continuation-in-part of U.S. application Ser. No. 12/413,231, filed Mar. 27, 2009, now abandoned, which claims the benefit of U.S. Provisional Application No. 61/040,594. Each of the aforementioned applications is incorporated by reference herein in its entirety, and each is hereby expressly made a part of this specification.

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events. A variety of intravascular, transcutaneous and implantable sensors have been developed for continuously detecting and quantifying blood glucose values. Many implantable glucose sensors suffer from complications within the body and provide only short-term or less-than-accurate sensing of blood glucose. Similarly, many transcutaneous and intravascular sensors have problems in accurately sensing and reporting back glucose values continuously over extended periods of time, for example, due to noise on the signal caused by interfering species or unknown noise-causing events.

SUMMARY OF THE INVENTION

In a first aspect, a device for continuous measurement of an analyte concentration is provided, the device comprising: a sensing mechanism configured to continuously measure a signal associated with an analyte concentration in a host; and a membrane located over the sensing mechanism, wherein the membrane comprises a polyurethane and a hydrophilic portion; wherein the device is configured to provide, at analyte concentrations of from about 40 mg/dL to about 400 mg/dL, a level of accuracy corresponding to a mean absolute relative difference of no more than about 8% over a sensor session of at least about 3 days, wherein one or more reference measurements associated with calculation of the mean absolute relative difference are determined by analysis of blood.

In an embodiment of the first aspect, the sensor session is at least about 5 days.

In an embodiment of the first aspect, the sensor session is at least about 6 days.

In an embodiment of the first aspect, the sensor session is at least about 7 days.

In an embodiment of the first aspect, the sensor session is at least about 10 days.

In an embodiment of the first aspect, the mean absolute relative difference is no more than about 7% over the sensor session.

In an embodiment of the first aspect, the membrane comprises an enzyme configured to react with the analyte.

In an embodiment of the first aspect, the membrane comprises a copolymer comprising a fluorocarbon segment.

In an embodiment of the first aspect, the membrane comprises a copolymer comprising a silicone segment.

In an embodiment of the first aspect, the membrane comprises a polycarbonate segment.

In a second aspect, a system for continuous measurement of an analyte concentration is provided, the system comprising: a sensor comprising: a sensing region configured to continuously produce sensor data associated with an analyte concentration in a host; and a membrane located over the sensing region, wherein the membrane comprises a polyurethane and a hydrophilic portion; a processor configured to process continuous sensor data; and a user interface configured to display information associated with continuous sensor data; wherein the sensor is configured to provide, at analyte concentrations of from about 40 mg/dL to about 400 mg/dL, a level of accuracy corresponding to a mean absolute relative difference of no more than about 8% over a sensor session of at least about 3 days, wherein one or more reference measurements associated with calculation of the mean absolute relative difference are determined by analysis of blood.

In an embodiment of the second aspect, the sensor session is at least about 5 days.

In an embodiment of the second aspect, the sensor session is at least about 6 days.

In an embodiment of the second aspect, the sensor session is at least about 7 days.

In an embodiment of the second aspect, the sensor session is at least about 10 days.

In an embodiment of the second aspect, the mean absolute relative difference is no more than about 7% over the sensor session.

In an embodiment of the second aspect, the membrane comprises an enzyme configured to react with the analyte.

In an embodiment of the second aspect, the membrane comprises a copolymer comprising a fluorocarbon segment.

In an embodiment of the second aspect, the membrane comprises a copolymer comprising a silicone segment.

In an embodiment of the second aspect, the membrane comprises a polycarbonate segment.

In a third aspect, a device for continuous measurement of an analyte concentration is provided, the device comprising: a sensing mechanism configured to continuously measure a signal associated with an analyte concentration in a host; and a membrane located over the sensing mechanism; wherein the device is configured to provide, at analyte concentrations of from about 40 mg/dL to about 80 mg/dL, a level of accuracy of a mean absolute relative difference of no more than about 10% over a sensor session of at least about 3 days, wherein one or more reference measurements associated with calculation of the mean absolute relative difference are determined by analysis of blood; and wherein the device is configured to provide, at analyte concentrations of from about 40 mg/dL to about 400 mg/dL, a level of accuracy of a mean absolute relative difference of no more than about 10% over the sensor session, wherein one or more reference measurements associated with calculation of the mean absolute relative difference are determined by analysis of blood.

In an embodiment of the third aspect, the membrane comprises an enzyme configured to react with the analyte.

In an embodiment of the third aspect, the membrane comprises a polyurethane and a hydrophilic portion.

In an embodiment of the third aspect, the membrane comprises a copolymer comprising a fluorocarbon segment.

In an embodiment of the third aspect, the membrane comprises a copolymer comprising a silicone segment.

In an embodiment of the third aspect, the membrane comprises a copolymer comprising a polycarbonate segment.

In a fourth aspect, a device for continuous measurement of an analyte concentration is provided, the device comprising: a sensing mechanism configured to continuously measure a signal associated with an analyte concentration in a host; and a membrane located over the sensing mechanism; wherein, over a sensor session of at least about 3 days, the device is configured to: provide a level of accuracy corresponding to a first mean absolute relative difference value at analyte concentrations of from about 40 mg/dL to about 80 mg/dL, wherein one or more reference measurements associated with calculation of the first mean absolute relative difference are determined by analysis of blood; and provide a level of accuracy corresponding to a second mean absolute relative difference value at analyte concentrations of from about 40 mg/dL to about 400 mg/dL, wherein one or more reference measurements associated with calculation of the second mean absolute relative difference are determined by analysis of blood; and wherein the first mean absolute relative difference value is less than or about equal to the second mean absolute relative difference value.

In an embodiment of the fourth aspect, the membrane comprises an enzyme configured to react with the analyte.

In an embodiment of the fourth aspect, the membrane comprises a polyurethane and a hydrophilic portion.

In an embodiment of the fourth aspect, the membrane comprises a copolymer comprising a fluorocarbon segment.

In an embodiment of the fourth aspect, the membrane comprises a copolymer comprising a silicone segment.

In an embodiment of the fourth aspect, the membrane comprises a copolymer comprising a polycarbonate segment.

In a fifth aspect, a system for continuous measurement of an analyte concentration is provided, the system comprising: a sensor comprising a sensing region configured to continuously produce sensor data associated with an analyte concentration in a host, wherein the sensor further comprises a membrane located over the sensing region; a processor configured to process continuous sensor data; and a user interface configured to display information associated with continuous sensor data; wherein the sensor is configured to provide, at analyte concentrations of from about 40 mg/dL to about 80 mg/dL, a level of accuracy of a mean absolute relative difference of no more than about 10% over a sensor session of at least about 3 days, wherein one or more reference measurements associated with calculation of the mean absolute relative difference are determined by analysis of blood; and wherein the sensor is configured to provide, at analyte concentrations of from about 40 mg/dL and about 400 mg/dL, a level of accuracy of a mean absolute relative difference of no more than about 10% over the sensor session, wherein one or more reference measurements associated with calculation of the mean absolute relative difference are determined by analysis of blood.

In an embodiment of the fifth aspect, the membrane comprises an enzyme configured to react with the analyte.

In an embodiment of the fifth aspect, the membrane comprises a polyurethane and a hydrophilic portion.

In an embodiment of the fifth aspect, the membrane comprises a copolymer comprising a fluorocarbon segment.

In an embodiment of the fifth aspect, the membrane comprises a copolymer comprising a silicone segment.

In an embodiment of the fifth aspect, the membrane comprises a copolymer comprising a polycarbonate segment.

In a sixth aspect, a system for continuous measurement of an analyte concentration is provided, the system comprising: a sensor comprising a sensing mechanism configured to continuously measure a signal associated with an analyte concentration in a host, wherein the sensor further comprises a membrane located over the sensing mechanism; a processor configured to process continuous sensor data; and a user interface configured to display information associated with continuous sensor data; wherein, over a sensor session of at least about 3 days, the system is configured to: provide a level of accuracy corresponding to a first mean absolute relative difference value at analyte concentrations of from about 40 mg/dL to about 80 mg/dL, wherein one or more reference measurements associated with calculation of the first mean absolute relative difference are determined by analysis of blood; and provide a level of accuracy corresponding to a second mean absolute relative difference value at analyte concentrations of from about 40 mg/dL to about 400 mg/dL, wherein one or more reference measurements associated with calculation of the second mean absolute relative difference are determined by analysis of blood; and wherein the first mean absolute relative difference value is less than or about equal to the second mean absolute relative difference value.

In an embodiment of the sixth aspect, the membrane comprises an enzyme configured to react with the analyte.

In an embodiment of the sixth aspect, the membrane comprises a polyurethane and a hydrophilic portion.

In an embodiment of the sixth aspect, the membrane comprises a copolymer comprising a fluorocarbon segment.

In an embodiment of the sixth aspect, the membrane comprises a copolymer comprising a silicone segment.

In an embodiment of the sixth aspect, the membrane comprises a copolymer comprising a polycarbonate segment.

BRIEF DESCRIPTION OF THE DRAWINGS

FIGS. 10A and 10B both also display glucose signal amplitudes and baseline signal amplitudes at certain glucose concentrations.

DETAILED DESCRIPTION OF THE PREFERRED EMBODIMENT

Figure 1:
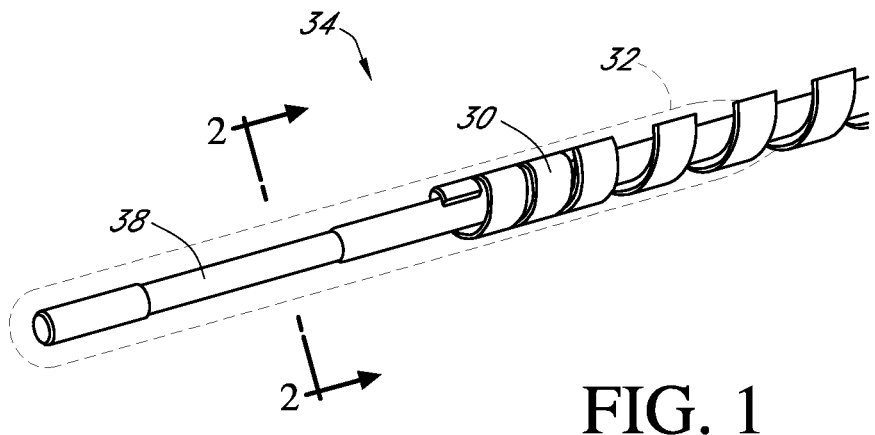
FIG. 1 is an expanded view of an exemplary embodiment of a continuous analyte sensor.

The following description and examples describe in detail some exemplary embodiments of devices and methods for providing continuous measurement of an analyte concentration. It should be appreciated that there are numerous variations and modifications of the devices and methods described herein that are encompassed by the present invention. Accordingly, the description of a certain exemplary embodiment should not be deemed to limit the scope of the present invention.

DEFINITIONS

In order to facilitate an understanding of the devices and methods described herein, a number of terms are defined below.

The term 'analyte' as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products. In some embodiments, the analyte for measurement by the sensing regions, devices, and methods is glucose. However, other analytes are contemplated as well, including, but not limited to: acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni, Toxoplasma gondii, Trepenoma pallidium, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to: insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The phrase 'continuous (or continual) analyte sensing' as used herein is a broad term, and is to be given its ordinary and customary meaning to a person of ordinary skill in the art (and is not to be limited to a special or customized meaning), and refers without limitation to the period in which monitoring of analyte concentration is continuously, continually, and or intermittently (but regularly) performed, for example, about every 5 to 10 minutes.

The terms 'operable connection,' 'operably connected,' and 'operably linked' as used herein are broad terms, and are to be given their ordinary and customary meaning to a person of ordinary skill in the art (and are not to be limited to a special or customized meaning), and refer without limitation to one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is 'operably linked' to the electronic circuitry.

The term 'host' as used herein is a broad term, and is to be given its ordinary and customary meaning to a person of ordinary skill in the art (and is not to be limited to a special or customized meaning), and refers without limitation to animals (e.g., humans) and plants.

The terms 'electrochemically reactive surface' and 'electroactive surface' as used herein are broad terms, and are to be given their ordinary and customary meaning to a person of ordinary skill in the art (and are not to be limited to a special or customized meaning), and refer without limitation to the surface of an electrode where an electrochemical reaction takes place. As one example, in a working electrode, $H_2O_2$ (hydrogen peroxide) produced by an enzyme-catalyzed reaction of an analyte being detected reacts and thereby creates a measurable electric current. For example, in the detection of glucose, glucose oxidase produces $H_2O_2$ as a byproduct. The $H_2O_2$ reacts with the surface of the working electrode to produce two protons ($2H^+$), two electrons ($2e^-$), and one molecule of oxygen ($O_2$), which produces the electric current being detected. In the case of the counter electrode, a reducible species, for example, $O_2$ is reduced at the electrode surface in order to balance the current being generated by the working electrode.

The terms 'sensing region,' 'sensor', and 'sensing mechanism' as used herein are broad terms, and are to be given their ordinary and customary meaning to a person of ordinary skill in the art (and are not to be limited to a special or customized meaning), and refer without limitation to the region or mechanism of a monitoring device responsible for the detection of a particular analyte.

The terms 'raw data stream' and 'data stream' as used herein are broad terms, and are to be given their ordinary and customary meaning to a person of ordinary skill in the art (and are not to be limited to a special or customized meaning), and refer without limitation to an analog or digital signal directly related to the measured glucose concentration from the glucose sensor. In one example, the raw data stream is digital data in 'counts' converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term 'counts' as used herein is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The term 'electrical potential' as used herein is a broad term, and is to be given its ordinary and customary meaning to a person of ordinary skill in the art (and is not to be limited to a special or customized meaning), and refers without limitation to the electrical potential difference between two points in a circuit which is the cause of the flow of a current.

The phrase 'distal to' as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a sensor include a membrane system having a bioprotective domain and an enzyme domain. If the sensor is deemed to be the point of reference and the bioprotective domain is positioned farther from the sensor than the enzyme domain, then the bioprotective domain is more distal to the sensor than the enzyme domain.

The phrase 'proximal to' as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a device include a membrane system having a bioprotective domain and an enzyme domain. If the sensor is deemed to be the point of reference and the enzyme domain is positioned nearer to the sensor than the bioprotective domain, then the enzyme domain is more proximal to the sensor than the bioprotective domain.

The terms 'interferents' and 'interfering species' as used herein are broad terms, and are to be given their ordinary and customary meaning to a person of ordinary skill in the art (and are not to be limited to a special or customized meaning), and refer without limitation to effects or species that interfere with the measurement of an analyte of interest in a sensor to produce a signal that does not accurately represent the analyte measurement. In an exemplary electrochemical sensor, interfering species can include compounds with an oxidation potential that overlaps with that of the analyte to be measured.

The term 'domain' as used herein is a broad term, and is to be given its ordinary and customary meaning to a person of ordinary skill in the art (and is not to be limited to a special or customized meaning), and refers without limitation to regions of a membrane that can be layers, uniform or non-uniform gradients (i.e., anisotropic) or provided as portions of the membrane.

The terms 'sensing membrane' and 'membrane system' as used herein are broad terms, and are to be given their ordinary and customary meaning to a person of ordinary skill in the art (and are not to be limited to a special or customized meaning), and refers without limitation to a permeable or semi-permeable membrane that can comprise one or more domains and constructed of materials of a few microns thickness or more, which are permeable to oxygen and may or may not be permeable to an analyte of interest. In one example, the sensing membrane or membrane system may comprise an immobilized glucose oxidase enzyme, which enables an electrochemical reaction to occur to measure a concentration of glucose.

The term 'baseline' as used herein is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation y=mx+b, the value of b represents the baseline of the signal.

The term 'sensitivity' as used herein is a broad term, and is to be given its ordinary and customary meaning to a person of ordinary skill in the art (and is not to be limited to a special or customized meaning), and refers without limitation to an amount of electrical current produced by a predetermined amount (unit) of the measured analyte. For example, in one embodiment, a sensor has a sensitivity (or slope) of from about 1 to about 100 picoAmps of current for every 1 mg/dL of glucose analyte.

The term 'sensor session' is a broad term, and is to be given its ordinary and customary meaning to a person of ordinary skill in the art (and is not to be limited to a special or customized meaning), and refers without limitation to the period of time the sensor is applied to (e.g., implanted in) the host or is being used to obtain sensor values. For example, in some embodiments, a sensor session extends from the time of sensor implantation (e.g., including insertion of the sensor into subcutaneous tissue and placing the sensor into fluid communication with a host's circulatory system) to the time when the sensor is removed.

As employed herein, the following abbreviations apply: Eq and Eqs (equivalents); mEq (milliequivalents); M (molar); mM (millimolar) µM (micromolar); N (Normal); mol (moles); mmol (millimoles); µmol (micromoles); nmol (nanomoles); g (grams); mg (milligrams); µg (micrograms); Kg (kilograms); L (liters); mL (milliliters); dL (deciliters); µL (microliters); cm (centimeters); mm (millimeters); µm (micrometers); nm (nanometers); h and hr (hours); min. (minutes); s and sec. (seconds); ° C. (degrees Centigrade).

Overview

Membrane systems of the preferred embodiments are suitable for use with implantable devices in contact with a biological fluid. For example, the membrane systems can be utilized with implantable devices, such as devices for monitoring and determining analyte levels in a biological fluid, for example, devices for monitoring glucose levels for individuals having diabetes. In some embodiments, the analyte-measuring device is a continuous device. The analyte-measuring device can employ any suitable sensing element to provide the raw signal, including but not limited to those involving enzymatic, chemical, physical, electrochemical, spectrophotometric, polarimetric, calorimetric, radiometric, immunochemical, or like elements.

Although some of the description that follows is directed at glucose-measuring devices, including the described membrane systems and methods for their use, these membrane systems are not limited to use in devices that measure or monitor glucose. These membrane systems are suitable for use in any of a variety of devices, including, for example, devices that detect and quantify other analytes present in biological fluids (e.g., cholesterol, amino acids, alcohol, galactose, and lactate), cell transplantation devices (see, for example, U.S. Pat. No. 6,015,572, U.S. Pat. No. 5,964,745, and U.S. Pat. No. 6,083,523), drug delivery devices (see, for example, U.S. Pat. No. 5,458,631, U.S. Pat. No. 5,820,589, and U.S. Pat. No. 5,972,369), and the like.

In one embodiment, the analyte sensor is an implantable glucose sensor, such as described with reference to U.S. Pat. No. 6,001,067 and U.S. Patent Publication No. US-2005-0027463-A1, each of which is incorporated herein by reference in its entirety. In another embodiment, the analyte sensor is a glucose sensor, such as described with reference to U.S. Patent Publication No. US-2006-0020187-A1, which is incorporated herein by reference in its entirety. In still other embodiments, the sensor is configured to be implanted in a host vessel or extra-corporeally, such as is described in U.S. Patent Publication No. US-2007-0027385-A1, U.S. Patent Publication No. US-2008-0119703-A1, U.S. Patent Publication No. US-20080108942-A1, and U.S. Patent Publication No. US-2007-0197890-A1, all of which are incorporated herein by reference in their entirety. In some embodiments, the sensor is configured as a dual-electrode sensor, such as described in U.S. Patent Publication No. US-2005-0143635-A1, U.S. Patent Publication No. US-2007-0027385-A1, U.S. Patent Publication No. US-2007-0213611-A1, and U.S. Patent Publication No. US-2008-0083617-A1, which are incorporated herein by reference in their entirety. In one alternative embodiment, the continuous glucose sensor comprises a sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In yet another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al. In some embodiments, the electrode system can be used with any of a variety of known in vivo analyte sensors or monitors, such as U.S. Pat. No. 7,157,528 to Ward; U.S. Pat. No. 6,212,416 to Ward et al.; U.S. Pat. No. 6,119,028 to Schulman et al.; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al.; U.S. Pat. No. 5,985,129 to Gough et al.; WO Patent Application Publication No. 04/021877 to Caduff; U.S. Pat. No. 5,494,562 to Maley et al.; U.S. Pat. No. 6,120,676 to Heller et al.; and U.S. Pat. No. 6,542,765 to Guy et al. In general, it is understood that the disclosed embodiments are applicable to a variety of continuous analyte measuring device configurations.

In some embodiments, a long term sensor (e.g., wholly implantable or intravascular) is configured to function for a time period of from about 30 days or less to about one year or more (e.g., a sensor session). In some embodiments, a short term sensor (e.g., one that is transcutaneous or intravascular) is configured and arranged to function for a time period of from about a few hours to about 30 days, including a time period of about 1, 2, 3, 4, 5, 6, 7, 8, 9, 10, 11, 12, 13, 14, 15, 16, 17, 18, 19, 20, 21, 22, 23, 24, 25, 26, 27, 28 or 29 days (e.g., a sensor session). As used herein, the term 'sensor session' is a broad term and refers without limitation to the period of time the sensor is applied to (e.g., implanted in) the host or is being used to obtain sensor values. For example, in some embodiments, a sensor session extends from the time of sensor implantation (e.g., including insertion of the sensor into subcutaneous tissue and placing the sensor into fluid communication with a host's circulatory system) to the time when the sensor is removed.

Exemplary Glucose Sensor Configuration

FIG. 1 is an expanded view of an exemplary embodiment of a continuous analyte sensor 34, also referred to as an analyte sensor, illustrating the sensing mechanism. In some embodiments, the sensing mechanism is adapted for insertion under the host's skin, and the remaining body of the sensor (e.g., electronics, etc.) can reside ex vivo. In the illustrated embodiment, the analyte sensor 34 includes two electrodes, i.e., a working electrode 38 and at least one additional electrode 30, which may function as a counter or reference electrode, hereinafter referred to as the reference electrode 30.

It is contemplated that the electrode may be formed to have any of a variety of cross-sectional shapes. For example, in some embodiments, the electrode may be formed to have a circular or substantially circular shape, but in other embodiments, the electrode may be formed to have a cross-sectional shape that resembles an ellipse, a polygon (e.g., triangle, square, rectangle, parallelogram, trapezoid, pentagon, hexagon, octagon), or the like. In various embodiments, the cross-sectional shape of the electrode may be symmetrical, but in other embodiments, the cross-sectional shape may be asymmetrical. In some embodiments, each electrode may be formed from a fine wire with a diameter of from about 0.001 or less to about 0.050 inches or more, for example, and is formed from, e.g., a plated insulator, a plated wire, or bulk electrically conductive material. In some embodiments, the wire used to form a working electrode may be about 0.002, 0.003, 0.004, 0.005, 0.006, 0.007, 0.008, 0.009, 0.01, 0.015, 0.02, 0.025, 0.03, 0.035, 0.04 or 0.045 inches in diameter. In some embodiments, the working electrode may comprise a wire formed from a conductive material, such as platinum, platinum-black, platinum-iridium, palladium, graphite, gold, carbon, conductive polymer, alloys, or the like. Although the illustrated electrode configuration and associated text describe one method of forming a sensor, any of a variety of known sensor configurations can be employed with the analyte sensor system.

The working electrode 38 is configured to measure the concentration of an analyte, such as, but not limited to glucose, uric acid, cholesterol, lactate, and the like. In an enzymatic electrochemical sensor for detecting glucose, for example, the working electrode may measure the hydrogen peroxide produced by an enzyme catalyzed reaction of the analyte being detected and creates a measurable electric current. For example, in the detection of glucose wherein glucose oxidase (GOX) produces $H_2O_2$ as a byproduct, the $H_2O_2$ reacts with the surface of the working electrode producing two protons ($2H^+$), two electrons ($2e^-$) and one molecule of oxygen ($O_2$), which produces the electric current being detected.

An insulator may be provided to electrically insulate the working and reference electrodes. In this exemplary embodiment, the working electrode 38 is covered with an insulating material, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating because of its strength, lubricity, and electrical insulation properties. Generally, parylene is produced by vapor deposition and polymerization of para-xylylene (or its substituted derivatives). However, any suitable insulating material can be used, for example, fluorinated polymers, polyethyleneterephthalate, polyurethane, polyimide, other nonconducting polymers, or the like. Glass or ceramic materials can also be employed. Other materials suitable for use include surface energy modified coating systems such as those marketed under the trade names AMC18, AMC148, AMC141, and AMC321 by Advanced Materials Components Express of Bellafonte, Pa. In some alternative embodiments, however, the working electrode may not require a coating of insulator.

In some embodiments, the reference electrode 30, which may function as a reference electrode alone, or as a dual reference and counter electrode, is formed from silver, silver/silver chloride, or the like. In some embodiments, the electrodes are juxtapositioned or twisted with or around each other, but it is contemplated, however, that other configurations are also possible. In one embodiment, the reference electrode 30 is helically wound around the working electrode 38. The assembly of wires may then be optionally coated together with an insulating material, similar to that described above, in order to provide an insulating attachment (e.g., securing together of the working and reference electrodes).

In embodiments wherein an outer insulator is disposed, a portion of the coated assembly structure can be stripped or otherwise removed, for example, by hand, excimer lasing, chemical etching, laser ablation, grit-blasting, or the like, to expose the electroactive surfaces. Alternatively, a portion of the electrode can be masked prior to depositing the insulator in order to maintain an exposed electroactive surface area.

In some embodiments, a radial window is formed through the insulating material to expose a circumferential electroactive surface of the working electrode. Additionally, sections of electroactive surface of the reference electrode are exposed. For example, the sections of electroactive surface can be masked during deposition of an outer insulating layer or etched after deposition of an outer insulating layer. In some applications, cellular attack or migration of cells to the sensor can cause reduced sensitivity or function of the device, particularly after the first day of implantation. However, when the exposed electroactive surface is distributed circumferentially about the sensor (e.g., as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

In some alternative embodiments, additional electrodes can be included within the assembly, for example, a three-electrode system (working, reference, and counter electrodes) and an additional working electrode (e.g., an electrode which can be used to generate oxygen, which is configured as a baseline subtracting electrode, or which is configured for measuring additional analytes). U.S. Pat. No.

7,081,195, U.S. Patent Publication No. US-2005-0143635-A1 and U.S. Patent Publication No. US-2007-0027385-A1, each of which are incorporated herein by reference, describe some systems and methods for implementing and using additional working, counter, and reference electrodes. In one implementation wherein the sensor comprises two working electrodes, the two working electrodes are juxtapositioned, around which the reference electrode is disposed (e.g., helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). The resulting electrode system can be configured with an appropriate membrane system, wherein the first working electrode is configured to measure a first signal comprising glucose and baseline signals, and the additional working electrode is configured to measure a baseline signal consisting of the baseline signal only. In these embodiments, the second working electrode may be configured to be substantially similar to the first working electrode, but without an enzyme disposed thereon. In this way, the baseline signal can be determined and subtracted from the first signal to generate a difference signal, i.e., a glucose-only signal that is substantially not subject to fluctuations in the baseline or interfering species on the signal, such as described in U.S. Patent Publication No. US-2005-0143635-A1, U.S. Patent Publication No. US-2007-0027385-A1, and U.S. Patent Publication No. US-2007-0213611-A1, and U.S. Patent Publication No. US-2008-0083617-A1, which are incorporated herein by reference in their entirety.

It has been found that in some electrode systems involving two working electrodes, i.e., in some dual-electrode systems, the working electrodes may be slightly different from each other. For instance, two working electrodes, even when manufactured from a single facility may slightly differ in thickness or permeability because of the electrodes' high sensitivity to environmental conditions (e.g., temperature, humidity) during fabrication. Accordingly, the working electrodes of a dual-electrode system may have varying diffusion, membrane thickness, and diffusion characteristics. As a result, the above-described difference signal (i.e., a glucose-only signal, generated from subtracting the baseline signal from the first signal) may not be completely accurate. To mitigate this, it is contemplated that in some dual-electrode systems, both working electrodes may be fabricated with one or more membranes that each includes a bioprotective layer, which is described in more detail elsewhere herein. Example 6 below describes in detail the results of reduction of interference-related signals achieved with one embodiment in which the sensor comprises two working electrodes, each of which is covered by a bioprotective layer.

It is contemplated that the sensing region may include any of a variety of electrode configurations. For example, in some embodiments, in addition to one or more glucose-measuring working electrodes, the sensing region may also include a reference electrode or other electrodes associated with the working electrode. In these particular embodiments, the sensing region may also include a separate reference or counter electrode associated with one or more optional auxiliary working electrodes. In other embodiments, the sensing region may include a glucose-measuring working electrode, an auxiliary working electrode, two counter electrodes (one for each working electrode), and one shared reference electrode. In yet other embodiments, the sensing region may include a glucose-measuring working electrode, an auxiliary working electrode, two reference electrodes, and one shared counter electrode.

U.S. Patent Publication No. US-2008-0119703-A1 and U.S. Patent Publication No. US-2005-0245799-A1 describe additional configurations for using the continuous sensor in different body locations. In some embodiments, the sensor is configured for transcutaneous implantation in the host. In alternative embodiments, the sensor is configured for insertion into the circulatory system, such as a peripheral vein or artery. However, in other embodiments, the sensor is configured for insertion into the central circulatory system, such as but not limited to the vena cava. In still other embodiments, the sensor can be placed in an extracorporeal circulation system, such as but not limited to an intravascular access device providing extracorporeal access to a blood vessel, an intravenous fluid infusion system, an extracorporeal blood chemistry analysis device, a dialysis machine, a heart-lung machine (i.e., a device used to provide blood circulation and oxygenation while the heart is stopped during heart surgery), etc. In still other embodiments, the sensor can be configured to be wholly implantable, as described in U.S. Pat. No. 6,001,067.

Figure 2A:
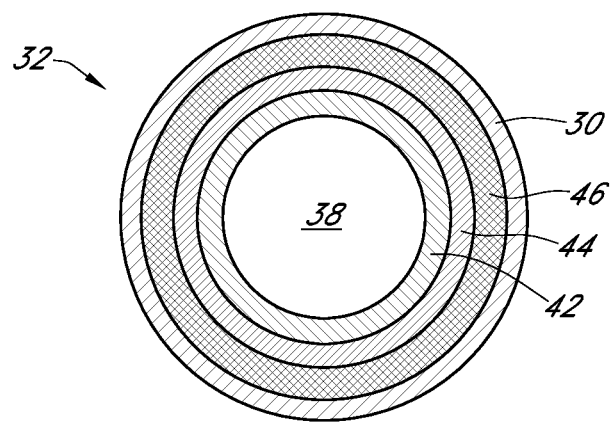
FIGS. 2A-2C are cross-sectional views through the sensor of FIG. 1 on line 2-2, illustrating various embodiments of the membrane system.

FIG. 2A is a cross-sectional view through the sensor of FIG. 1 on line 2-2, illustrating one embodiment of the membrane system 32. In this particular embodiment, the membrane system includes an enzyme domain 42, a diffusion resistance domain 44, and a bioprotective domain 46 located around the working electrode 38, all of which are described in more detail elsewhere herein. In some embodiments, a unitary diffusion resistance domain and bioprotective domain may be included in the membrane system (e.g., wherein the functionality of both domains is incorporated into one domain, i.e., the bioprotective domain). In some embodiments, the sensor is configured for short-term implantation (e.g., from about 1 to 30 days). However, it is understood that the membrane system 32 can be modified for use in other devices, for example, by including only one or more of the domains, or additional domains.

Figure 2B:
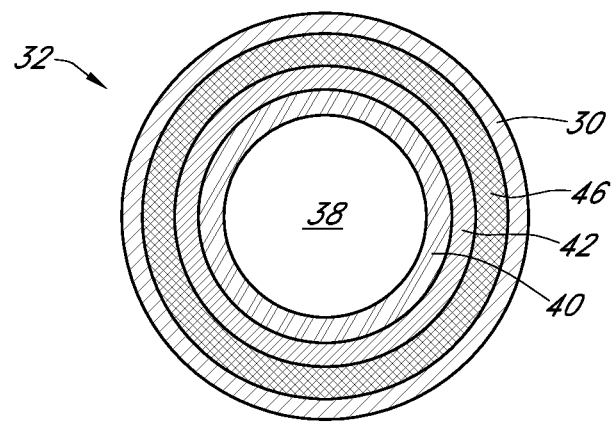

In some embodiments, the membrane system may include a bioprotective domain 46, also referred to as a cell-impermeable domain or biointerface domain, comprising a surface-modified base polymer as described in more detail elsewhere herein. However, the sensing membranes 32 of some embodiments can also include a plurality of domains or layers including, for example, an electrode domain (e.g., as illustrated in the FIG. 2C), an interference domain (e.g., as illustrated in FIG. 2B), or a cell disruptive domain (not shown), such as described in more detail elsewhere herein and in U.S. Patent Publication No. US-2006-0036145-A1, which is incorporated herein by reference in its entirety.

It is to be understood that sensing membranes modified for other sensors, for example, may include fewer or additional layers. For example, in some embodiments, the membrane system may comprise one electrode layer, one enzyme layer, and two bioprotective layers, but in other embodiments, the membrane system may comprise one electrode layer, two enzyme layers, and one bioprotective layer. In some embodiments, the bioprotective layer may be configured to function as the diffusion resistance domain and control the flux of the analyte (e.g., glucose) to the underlying membrane layers.

In some embodiments, one or more domains of the sensing membranes may be formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some embodiments, the sensing membrane can be deposited on the electroactive surfaces of the electrode material using known thin or thick film techniques (for example, spraying, electro-depositing, dipping, or the like). The sensing membrane located over the working electrode does not have to have the same structure as the sensing membrane located over the reference electrode; for example, the enzyme domain deposited over the working electrode does not necessarily need to be deposited over the reference or counter electrodes.

Figure 2C:
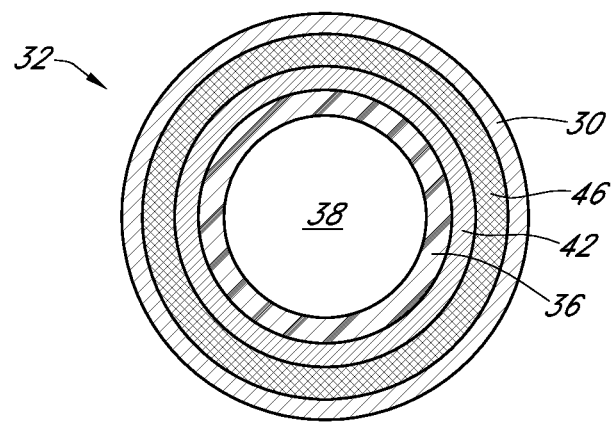

Although the exemplary embodiments illustrated in FIGS. 2A-2C involve circumferentially extending membrane systems, the membranes described herein may be applied to any planar or non-planar surface, for example, the substrate-based sensor structure of U.S. Pat. No. 6,565,509 to Say et al.

Sensor Electronics

In general, analyte sensor systems have electronics associated therewith, also referred to as a 'computer system' that can include hardware, firmware, or software that enable measurement and processing of data associated with analyte levels in the host. In one exemplary embodiment of an electrochemical sensor, the electronics include a potentiostat, a power source for providing power to the sensor, and other components useful for signal processing. In additional embodiments, some or all of the electronics can be in wired or wireless communication with the sensor or other portions of the electronics. For example, a potentiostat disposed on the device can be wired to the remaining electronics (e.g., a processor, a recorder, a transmitter, a receiver, etc.), which reside on the bedside. In another example, some portion of the electronics is wirelessly connected to another portion of the electronics (e.g., a receiver), such as by infrared (IR) or RF. It is contemplated that other embodiments of electronics may be useful for providing sensor data output, such as those described in U.S. Patent Publication No. US-2005-0192557-A1, U.S. Patent Publication No. US-2005-0245795-A1; U.S. Patent Publication No. US-2005-0245795-A1, and U.S. Patent Publication No. US-2005-0245795-A1, U.S. Patent Publication No. US-2008-0119703-A1, and U.S. Patent Publication No. US-2008-0108942-A1, each of which is incorporated herein by reference in its entirety.

In one preferred embodiment, a potentiostat is operably connected to the electrode(s) (such as described elsewhere herein), which biases the sensor to enable measurement of a current signal indicative of the analyte concentration in the host (also referred to as the analog portion). In some embodiments, the potentiostat includes a resistor that translates the current into voltage. In some alternative embodiments, a current to frequency converter is provided that is configured to continuously integrate the measured current, for example, using a charge counting device. In some embodiments, the electronics include an A/D converter that digitizes the analog signal into a digital signal, also referred to as 'counts' for processing. Accordingly, the resulting raw data stream in counts, also referred to as raw sensor data, is directly related to the current measured by the potentiostat.

In general, the electronics include a processor module that includes the central control unit that controls the processing of the sensor system. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing or replacement of signal artifacts such as is described in U.S. Patent Publication No. US-2005-0043598-A1). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like.

In some embodiments, the processor module comprises a digital filter, for example, an infinite impulse response (IIR) or finite impulse response (FIR) filter, configured to smooth the raw data stream. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter.

In some embodiments, the processor module is configured to build the data packet for transmission to an outside source, for example, an RF transmission to a receiver. Generally, the data packet comprises a plurality of bits that can include a preamble, a unique identifier identifying the electronics unit, the receiver, or both, (e.g., sensor ID code), data (e.g., raw data, filtered data, or an integrated value) or error detection or correction. Preferably, the data (transmission) packet has a length of from about 8 bits to about 128 bits, preferably about 48 bits; however, larger or smaller packets can be desirable in certain embodiments. The processor module can be configured to transmit any combination of raw or filtered data. In one exemplary embodiment, the transmission packet contains a fixed preamble, a unique ID of the electronics unit, a single five-minute average (e.g., integrated) sensor data value, and a cyclic redundancy code (CRC).

In some embodiments, the processor further performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, and the like. In such cases, the processor includes hardware and software that performs the processing described herein, for example flash memory provides permanent or semi-permanent storage of data, storing data such as sensor ID, receiver ID, and programming to process data streams (for example, programming for performing estimation and other algorithms described elsewhere herein) and random access memory (RAM) stores the system's cache memory and is helpful in data processing. Alternatively, some portion of the data processing (such as described with reference to the processor elsewhere herein) can be accomplished at another (e.g., remote) processor and can be configured to be in wired or wireless connection therewith.

In some embodiments, an output module, which is integral with or operatively connected with the processor, includes programming for generating output based on the data stream received from the sensor system and it's processing incurred in the processor. In some embodiments, output is generated via a user interface.

Noise

Generally, implantable sensors measure a signal related to an analyte of interest in a host. For example, an electrochemical sensor can measure glucose, creatinine, or urea in a host, such as an animal (e.g., a human). Generally, the signal is converted mathematically to a numeric value indicative of analyte status, such as analyte concentration, as described in more detail elsewhere herein. In general, the signal generated by conventional analyte sensors contains some noise. Noise is clinically important because it can induce error and can reduce sensor performance, such as by providing a signal that causes the analyte concentration to appear higher or lower than the actual analyte concentration. For example, upward or high noise (e.g., noise that causes the signal to increase) can cause the reading of the host's glucose concentration to appear higher than the actual value, which in turn can lead to improper treatment decisions. Similarly, downward or low noise (e.g., noise that causes the signal to decrease) can cause the reading of the host's glucose concentration to appear lower than its actual value, which in turn can also lead to improper treatment decisions. Accordingly, noise reduction is desirable.

In general, the signal detected by the sensor can be broken down into its component parts. For example, in an enzymatic electrochemical analyte sensor, preferably after sensor break-in is complete, the total signal can be divided into an 'analyte component,' which is representative of analyte (e.g., glucose) concentration, and a 'noise component,' which is caused by non-analyte-related species that have a redox potential that substantially overlaps with the redox potential of the analyte (or measured species, e.g., $H_2O_2$) at an applied voltage. The noise component can be further divided into its component parts, e.g., constant and non-constant noise. It is not unusual for a sensor to experience a certain level of noise. In general, 'constant noise' (also referred to as constant background or baseline) is caused by non-analyte-related factors that are relatively stable over time, including but not limited to electroactive species that arise from generally constant (e.g., daily) metabolic processes. Constant noise can vary widely between hosts. In contrast, 'non-constant noise' (also referred to as non-constant background) is generally caused by non-constant, non-analyte-related species (e.g., non-constant noise-causing electroactive species) that may arise during transient events, such as during host metabolic processes (e.g., wound healing or in response to an illness), or due to ingestion of certain compounds (e.g., certain drugs). In some circumstances, noise can be caused by a variety of noise-causing electroactive species, which are discussed in detail elsewhere herein.

Figure 3:
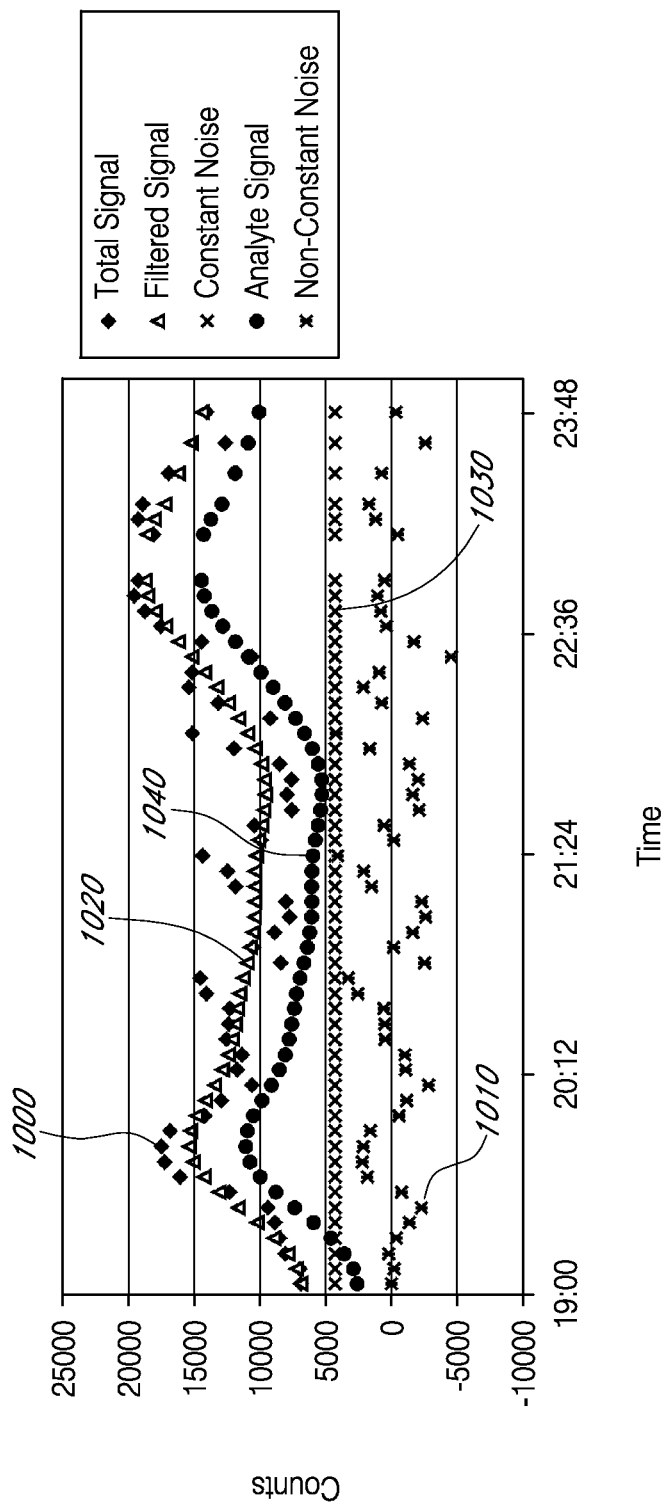
FIG. 3 is a graph illustrating the components of a signal measured by a glucose sensor (after sensor break-in was complete), in a non-diabetic volunteer host.

FIG. 3 is a graph illustrating the components of a signal measured by a transcutaneous glucose sensor (after sensor break-in was complete), in a non-diabetic volunteer host. The Y-axis indicates the signal amplitude (in counts) detected by the sensor. The total signal collected by the sensor is represented by line 1000, which includes components related to glucose, constant noise, and non-constant noise, which are described in more detail elsewhere herein. In some embodiments, the total signal is a raw data stream, which can include an averaged or integrated signal, for example, using a charge-counting device.

The non-constant noise component of the total signal is represented by line 1010. The non-constant noise component 1010 of the total signal 1000 can be obtained by filtering the total signal 1000 to obtain a filtered signal 1020 using any of a variety of known filtering techniques, and then subtracting the filtered signal 1020 from the total signal 1000. In some embodiments, the total signal can be filtered using linear regression analysis of the n (e.g., 10) most recent sampled sensor values. In some embodiments, the total signal can be filtered using non-linear regression. In some embodiments, the total signal can be filtered using a trimmed regression, which is a linear regression of a trimmed mean (e.g., after rejecting wide excursions of any point from the regression line). In this embodiment, after the sensor records glucose measurements at a predetermined sampling rate (e.g., every 30 seconds), the sensor calculates a trimmed mean (e.g., removes highest and lowest measurements from a data set) and then regresses the remaining measurements to estimate the glucose value. In some embodiments, the total signal can be filtered using a non-recursive filter, such as a finite impulse response (FIR) filter. An FIR filter is a digital signal filter, in which every sample of output is the weighted sum of past and current samples of input, using only some finite number of past samples. In some embodiments, the total signal can be filtered using a recursive filter, such as an infinite impulse response (IIR) filter. An IIR filter is a type of digital signal filter, in which every sample of output is the weighted sum of past and current samples of input. In some embodiments, the total signal can be filtered using a maximum-average (max-average) filtering algorithm, which smoothes data based on the discovery that the substantial majority of signal artifacts observed after implantation of glucose sensors in humans, for example, is not distributed evenly above and below the actual blood glucose levels. It has been observed that many data sets are actually characterized by extended periods in which the noise appears to trend downwardly from maximum values with occasional high spikes. To overcome these downward trending signal artifacts, the max-average calculation tracks with the highest sensor values, and discards the bulk of the lower values. Additionally, the max-average method is designed to reduce the contamination of the data with unphysiologically high data from the high spikes. The max-average calculation smoothes data at a sampling interval (e.g., every 30 seconds) for transmission to the receiver at a less frequent transmission interval (e.g., every 5 minutes), to minimize the effects of low non-physiological data. First, the microprocessor finds and stores a maximum sensor counts value in a first set of sampled data points (e.g., 5 consecutive, accepted, thirty-second data points). A frame shift time window finds a maximum sensor counts value for each set of sampled data (e.g., each 5-point cycle length) and stores each maximum value. The microprocessor then computes a rolling average (e.g., 5-point average) of these maxima for each sampling interval (e.g., every 30 seconds) and stores these data. Periodically (e.g., every $10^{th}$ interval), the sensor outputs to the receiver the current maximum of the rolling average (e.g., over the last 10 thirty-second intervals as a smoothed value for that time period (e.g., 5 minutes)). In some embodiments, the total signal can be filtered using a 'Cone of Possibility Replacement Method,' which utilizes physiological information along with glucose signal values in order define a 'cone' of physiologically feasible glucose signal values within a human. Particularly, physiological information depends upon the physiological parameters obtained from continuous studies in the literature as well as our own observations. A first physiological parameter uses a maximal sustained rate of change of glucose in humans (e.g., about 4 to 6 mg/dl/min) and a maximum sustained acceleration of that rate of change (e.g., about 0.1 to 0.2 mg/min/min). A second physiological parameter uses the knowledge that rate of change of glucose is lowest at the maxima and minima, which are the areas of greatest risk in patient treatment. A third physiological parameter uses the fact that the best solution for the shape of the curve at any point along the curve over a certain time period (e.g., about 20-25 minutes) is a straight line. The maximum rate of change can be narrowed in some instances. Therefore, additional physiological data can be used to modify the limits imposed upon the Cone of Possibility Replacement Method for sensor glucose values. For example, the maximum per minute rate of change can be lower when the subject is lying down or sleeping; on the other hand, the maximum per minute rate change can be higher when the subject is exercising, for example. In some embodiments, the total signal can be filtered using reference changes in electrode potential to estimate glucose sensor data during positive detection of signal artifacts from an electrochemical glucose sensor, the method hereinafter referred to as reference drift replacement; in this embodiment, the electrochemical glucose sensor comprises working, counter, and reference electrodes. This method exploits the function of the reference electrode as it drifts to compensate for counter electrode limitations during oxygen deficits, pH changes, or temperature changes. In alternative implementations of the reference drift method, a variety of algorithms can therefore be implemented based on the changes measured in the reference electrode. Linear algorithms, and the like, are suitable for interpreting the direct relationship between reference electrode drift and the non-glucose rate limiting signal noise such that appropriate conversion to signal noise compensation can be derived. Additional description of signal filtering can be found in U.S. Patent Publication No. US-2005-0043598-A1.

The constant noise signal component 1030 can be obtained by calibrating the sensor signal using reference data, such as one or more blood glucose values obtained from a hand-held blood glucose meter, or the like, from which the baseline 'b' of a regression can be obtained, representing the constant noise signal component 1030.

The analyte signal component 1040 can be obtained by subtracting the constant noise signal component 1030 from the filtered signal 1020.

In general, non-constant noise is caused by interfering species (non-constant noise-causing species), which can be compounds, such as drugs that have been administered to the host, or intermittently produced products of various host metabolic processes. Exemplary interferents include but are not limited to a variety of drugs (e.g., acetaminophen), $H_2O_2$ from exterior sources (e.g., produced outside the sensor membrane system), and reactive metabolic species (e.g., reactive oxygen and nitrogen species, some hormones, etc.). Some known interfering species for a glucose sensor include but are not limited to acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid.

In some experiments of implantable glucose sensors, it was observed that noise increased when some hosts were intermittently sedentary, such as during sleep or sitting for extended periods. When the host began moving again, the noise quickly dissipated. Noise that occurs during intermittent, sedentary periods (also referred to as intermittent sedentary noise) can occur during relatively inactive periods, such as sleeping. Non-constant, non-analyte-related factors can cause intermittent sedentary noise, such as was observed in one exemplary study of non-diabetic individuals implanted with enzymatic-type glucose sensors built without enzyme. These sensors (without enzyme) could not react with or measure glucose and therefore provided a signal due to non-glucose effects only (e.g., constant and non-constant noise). During sedentary periods (e.g., during sleep), extensive, sustained signal was observed on the sensors. Then, when the host got up and moved around, the signal rapidly corrected. As a control, in vitro experiments were conducted to determine if a sensor component might have leached into the area surrounding the sensor and caused the noise, but none was detected. From these results, it is believed that a host-produced non-analyte related reactant was diffusing to the electrodes and producing the unexpected non-constant noise signal.

Interferents

Interferents are molecules or other species that may cause a sensor to generate a false positive or negative analyte signal (e.g., a non-analyte-related signal). Some interferents are known to become reduced or oxidized at the electrochemically reactive surfaces of the sensor, while other interferents are known to interfere with the ability of the enzyme (e.g., glucose oxidase) used to react with the analyte being measured. Yet other interferents are known to react with the enzyme (e.g., glucose oxidase) to produce a byproduct that is electrochemically active. Interferents can exaggerate or mask the response signal, thereby leading to false or misleading results. For example, a false positive signal may cause the host's analyte concentration (e.g., glucose concentration) to appear higher than the true analyte concentration. False-positive signals may pose a clinically significant problem in some conventional sensors. For example in a severe hypoglycemic situation, in which the host has ingested an interferent (e.g., acetaminophen), the resulting artificially high glucose signal can lead the host to believe that he is euglycemic or hyperglycemic. In response, the host may make inappropriate treatment decisions, such as by injecting himself with too much insulin, or by taking no action, when the proper course of action would be to begin eating. In turn, this inappropriate action or inaction may lead to a dangerous hypoglycemic episode for the host. Accordingly, it is desired that a membrane system can be developed that substantially reduces or eliminates the effects of interferents on analyte measurements. As described in more detail elsewhere herein, it is contemplated that a membrane system having one or more domains capable of blocking or substantially reducing the flow of interferents onto the electroactive surfaces of the electrode may reduce noise and improve sensor accuracy.

With respect to analyte sensors, it is contemplated that a number of types of interferents may cause inaccurate readings. One type of interferents is defined herein as 'exogenous interferents.' The term 'exogenous interferents' as used herein is a broad term, and is to be given its ordinary and customary meaning to a person of ordinary skill in the art (and are not to be limited to a special or customized meaning), and refers without limitation to interferents that affect the measurement of glucose and that are present in the host, but that have origins outside of the body, and that can include items administered to a person, such as medicaments, drugs, foods or herbs, whether administered intravenously, orally, topically, etc. By way of example, acetaminophen ingested by a host or the lidocaine injected into a host would be considered herein as exogenous interferents.

Another type of interferents is defined herein as 'endogenous interferents.' The term 'endogenous interferents' as used herein is a broad term, and is to be given its ordinary and customary meaning to a person of ordinary skill in the art (and are not to be limited to a special or customized meaning), and refers without limitation to interferents that affect the measurement of glucose and that have origins within the body, and thus includes interferents derived from species or metabolites produced during cell metabolism (e.g., as a result of wound healing). While not wishing to be bound by theory, it is believed that a local build up of electroactive interferents, such as electroactive metabolites derived from cellular metabolism and wound healing, may interfere with sensor function and cause early intermittent, sedentary noise. Local lymph pooling, when parts of the body are compressed or when the body is inactive, may also cause, in part, this local build up of interferents (e.g., electroactive metabolites). Endogenous interferents may react with the membrane system in ways that are different from exogenous interferents. Endogenous interferents may include but are not limited to compounds with electroactive acidic, amine or sulfhydryl groups, urea (e.g., as a result of renal failure), lactic acid, phosphates, citrates, peroxides, amino acids (e.g., L-arginine), amino acid precursors or break-down products, nitric oxide (NO), NO-donors, NO-precursors, or other electroactive species or metabolites produced during cell metabolism or wound healing, for example.

Noise-Reducing Membrane System

In some embodiments, the continuous sensor may have a bioprotective domain which includes a polymer containing one or more surface-active groups configured to substantially reduce or block the effect or influence of non-constant noise-causing species. In some of these embodiments, the reduction or blocking of the effect or influence of non-constant noise-causing species may be such that the non-constant noise component of the signal is less than about 60%, 50%, 40%, 30%, 20%, or 10% of the total signal. In some embodiments, the sensor may include at least one electrode and electronics configured to provide a signal measured at the electrode. The measured signal can be broken down (e.g., after sensor break-in) into its component parts, which may include but are not limited to a substantially analyte-related component, a substantially constant non-analyte-related component (e.g., constant noise), and a substantially non-constant non-analyte-related component (e.g., non-constant noise). In some of these embodiments, the sensor may be configured such that the substantially non-constant non-analyte-related component does not substantially contribute to the signal for at least about one or two days. In some embodiments, the signal contribution of the non-constant noise may be less than about 60%, 50%, 40%, 30%, 20%, or 10% of the signal (i.e., total signal) over a time period of at least about one day, but in other embodiments, the time period may be at least about two, three, four, five, six, seven days or more, including weeks or months, and the signal contribution of the non-constant noise may be less than about 18%, 16%, 14%, 12%, 10%, 8%, 6%, 5%, 4%, 3%, 2%, or 1%. It is contemplated that in some embodiments, the sensor may be configured such that the signal contribution of the analyte-related component is at least about 50%, 60%, 70%, 80%, 90% or more of the total signal over a time period of at least about one day; but in some embodiments, the time period may be at least about two, three, four, five, six, seven days or more, including weeks or months, and the signal contribution of the analyte-related component may be at least about 50%, 55%, 60%, 65%, 70%, 75%, 80%, 82%, 84%, 86%, 88%, 90%, 91%, 92%, 93%, 94%, 95%, 96%, 97%, 98%, 99% or more.

A signal component's percentage of the total signal can be determined using a variety of methods of quantifying an amplitude of signal components and total signal, from which each component's percent contribution can be calculated. In some embodiments, the signal components can be quantified by comparing the peak-to-peak amplitudes of each signal component for a time period, whereby the peak-to-peak amplitudes of each component can be compared to the peak-to-peak amplitude of the total signal to determine its percentage of the total signal. In some embodiments, the signal components can be quantified by determining the Root Mean Square (RMS) of the signal component for a time period. In one exemplary of Root Mean Square analysis of signal components, the signal component(s) can be quantified using the formula:

$$RMS = \sqrt{\frac{\sum (x_1^2 + x_2^2 + x_3^2 + x_n^2)}{n}}$$

wherein there are a number (n) of data values (x) for a signal (e.g., analyte component, non-constant noise component, constant noise component, and total signal) during a predetermined time period (e.g., about 1 day, about 2 days, about 3 days, etc). Once the signal components and total signal are quantified, the signal components can be compared to the total signal to determine a percentage of each signal component within the total signal.

Bioprotective Domain

The bioprotective domain is the domain or layer of an implantable device configured to interface with (e.g., contact) a biological fluid when implanted in a host or connected to the host (e.g., via an intravascular access device providing extracorporeal access to a blood vessel). As described above, membranes of some embodiments may include a bioprotective domain 46 (see FIGS. 2A-2C), also referred to as a bioprotective layer, including at least one polymer containing a surface-active group. In some embodiments, the surface-active group-containing polymer is a surface-active end group-containing polymer. In some of these embodiments, the surface-active end group-containing polymer is a polymer having covalently bonded surface-active end groups. However, it is contemplated that other surface-active group-containing polymers may also be used and can be formed by modification of fully-reacted base polymers via the grafting of side chain structures, surface treatments or coatings applied after membrane fabrication (e.g., via surface-modifying additives), blending of a surface-modifying additive to a base polymer before membrane fabrication, immobilization of the surface-active-group-containing soft segments by physical entrainment during synthesis, or the like.

Base polymers useful for certain embodiments may include any linear or branched polymer on the backbone structure of the polymer. Suitable base polymers may include, but are not limited to, epoxies, polyolefins, polysiloxanes, polyethers, acrylics, polyesters, carbonates, and polyurethanes, wherein polyurethanes may include polyurethane copolymers such as polyether-urethane-urea, polycarbonate-urethane, polyether-urethane, silicone-polyether-urethane, silicone-polycarbonate-urethane, polyester-urethane, and the like. In some embodiments, base polymers may be selected for their bulk properties, such as, but not limited to, tensile strength, flex life, modulus, and the like. For example, polyurethanes are known to be relatively strong and to provide numerous reactive pathways, which properties may be advantageous as bulk properties for a membrane domain of the continuous sensor.

In some embodiments, a base polymer synthesized to have hydrophilic segments may be used to form the bioprotective layer. For example, a linear base polymer including biocompatible segmented block polyurethane copolymers comprising hard and soft segments may be used. In some embodiments, the hard segment of the copolymer may have a molecular weight of from about 160 daltons to about 10,000 daltons, and in certain embodiments from about 200 daltons to about 2,000 daltons. In some embodiments, the molecular weight of the soft segment may be from about 200 daltons to about 10,000,000 daltons, and in certain embodiments from about 500 daltons to about 5,000,000 daltons, and in certain embodiments from about 500,00 daltons to about 2,000,000 daltons. It is contemplated that polyisocyanates used for the preparation of the hard segments of the copolymer may be aromatic or aliphatic diisocyanates. The soft segments used in the preparation of the polyurethane may be a polyfunctional aliphatic polyol, a polyfunctional aliphatic or aromatic amine, or the like that may be useful for creating permeability of the analyte (e.g., glucose) therethrough, and may include, for example, polyvinyl acetate (PVA), poly(ethylene glycol) (PEG), polyacrylamide, acetates, polyethylene oxide (PEO), polyethylacrylate (PEA), polyvinylpyrrolidone (PVP), variations thereof (e.g., PVP vinyl acetate), and copolymers, mixtures, and/or combinations thereof (e.g., a blend of polyurethane-PVP vinyl acetate copolymer with a PVP polymer).

Alternatively, in some embodiments, the bioprotective layer may comprise a combination of a base polymer (e.g., polyurethane) and one or more hydrophilic polymers, such as, PVA, PEG, polyacrylamide, acetates, PEO, PEA, PVP, and variations thereof (e.g., PVP vinyl acetate), e.g., as a physical blend or admixture wherein each polymer maintains its unique chemical nature. It is contemplated that any of a variety of combination of polymers may be used to yield a blend with desired glucose, oxygen, and interference permeability properties. For example, in some embodiments, the bioprotective layer may be formed from a blend of a polycarbonate-urethane base polymer and PVP, but in other embodiments, a blend of a polyurethane, or another base polymer, and one or more hydrophilic polymers may be used instead. In some of the embodiments involving use of PVP, the PVP portion of the polymer blend may comprise from about 5% to about 50% by weight of the polymer blend, in certain embodiments from about 15% to 20%, and in other embodiments from about 25% to 40%. It is contemplated that PVP of various molecular weights may be used. For example, in some embodiments, the molecular weight of the PVP used may be from about 25,000 daltons to about 5,000,000 daltons, in certain embodiments from about 50,000 daltons to about 2,000,000 daltons, and in other embodiments from 6,000,000 daltons to about 10,000,000 daltons. In still other embodiments, the bioprotective layer may comprise a combination of a base polymer having one or more hydrophilic segments and a hydrophilic polymer. The hydrophilic segments of the base polymer and the hydrophilic polymer may include, but are not limited to, polyvinyl acetate (PVA), poly(ethylene glycol) (PEG), polyacrylamide, acetates, polyethylene oxide (PEO), poly ethyl acrylate (PEA), polyvinylpyrrolidone, and copolymers, variations, and combinations thereof (e.g., PVP vinyl acetate).

Membranes have been developed that are capable of controlling the flux of a particular analyte passing through the membrane. However, it is known that conventional membranes typically lack the capability of substantially reducing or blocking the flux of interferents passing therethrough. From a membrane design perspective, typically as a membrane is made more permeable (i.e., opened up) for an analyte to pass through, this increased permeability of the membrane for the analyte tends to also increase the permeability of interferents. As an example, a conventional membrane that allows for a flux of glucose (with a M.W. of 180 daltons) through the membrane will typically not substantially reduce or block the flux of interferents, such as acetaminophen (with a M.W. of 151.2 daltons) through the membrane. Accordingly, without a mechanism designed to reduce the flux of interferents, large levels of undesirable signal noise may be generated as a result of the interferents passing through the membrane. Advantageously, some embodiments described herein provide a membrane layer that overcomes the above-described deficiencies by providing a mechanism for selectively controlling the flux of a particular analyte, while also substantially reducing or blocking the flux of interferents through the membrane.

While not wishing to be bound by theory, it is believed that in some conventional membranes formed with various segmented block polyurethane copolymers, the hydrophobic portions of the copolymer (e.g., the hard segments) may tend to segregate from the hydrophilic portions (e.g., the soft segments), which in turn, may cause the hydrophilic portions to align and form channels, through which analytes, such as glucose, and other molecules, such as exogenous interferents like acetaminophen, may pass through the bioprotective layer from the distal surface to the proximal surface. While the diffusion of analytes through the bioprotective layer is desired, the diffusion of interferents is generally not. Through experiments, it has been unexpectedly found that the use of PVP blended with a base polymer, such as, silicone-polycarbonate-urethane, may provide the bioprotective layer with the capability of substantially reducing or blocking the flux of various interferents, such as acetaminophen, through the layer. While not wishing to be bound by theory, it is believed that the carbonyl groups of PVP molecules may form hydrogen bonds with various interferents. For example, acetaminophen molecules are known to be capable of hydrogen bonding via their hydroxyl (O—H) and amide (H—N—(C=O)) groups, and thus through these moieties may interact with PVP. Although PVP is described here to provide an example of a hydrophilic polymer capable of providing the hydrogen bonding effects described above, it is contemplated that any of a variety of other hydrophilic polymers known to have strong hydrogen bonding properties may also be used, such as, polyvinyl pyrrolidone-vinyl acetate (PVP-VA), hydroxypropyl cellulose (HPC), hydroxypropyl methylcellulose (HPMC), for example.

In some embodiments, the bioprotective domain is configured to substantially reduce or block the flux of at least one interferent, and exhibits a glucose-to-interferent permeability ratio of approximately 1 to 30, but in other embodiments the glucose-to-interferent permeability ratio (e.g., glucose-to-acetaminophen permeability ratio) may be less than approximately 1 to 1, 1 to 2, 1 to 5, 1 to 10, 1 to 15, 1 to 20, 1 to 35, 1 to 40, 1 to 45, 1 to 50, or 1 to 100. The glucose-to-interferent permeability ratios exhibited by these embodiments are an improvement over conventional polyurethane membranes which typically exhibit glucose-to-interferent permeability ratios (e.g., glucose-to-acetaminophen permeability ratios) greater than 1 to 300. In some embodiments, the equivalent peak glucose response to a 1,000 mg dose of acetaminophen is less than about 100 mg/dL, in certain embodiments less than 80 mg/dL, and in other embodiments less than about 50 mg/dL, and in still other embodiments less than about 20 mg/dL.

Figure 8:
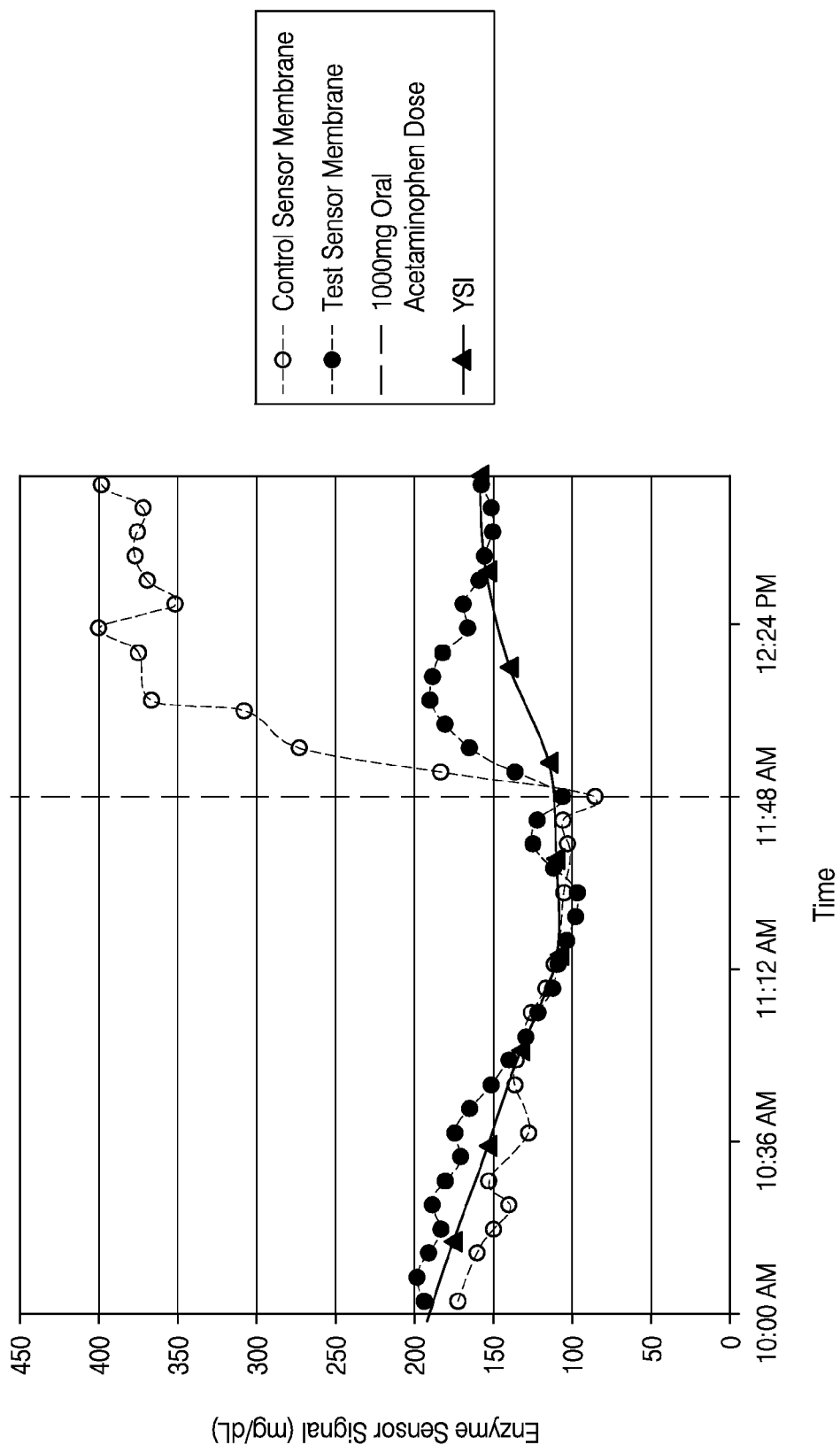
FIG. 8 is a graph illustrating signals, following administration of acetaminophen, received from an enzymatic electrode with a bioprotective layer formed with silicone-polycarbonate-urethane blended with PVP, compared to one formed with a conventional polyurethane membrane, as described in Example 5.

FIG. 8 illustrates and Example 5 describes the level of blocking of the interferent acetaminophen as exhibited by a bioprotective domain comprising PVP blended with silicone-polycarbonate-urethane base polymer. While this particular polymer was formed by blending a base silicone-polycarbonate-urethane polymer with PVP before membrane fabrication, it is contemplated that other methods, such as, surface treatments applied after membrane fabrication (e.g., via surface-modifying additives), immobilization of surface-active-group-containing segments by physical entrainment during synthesis of the polymer, for example, may also be used and may also provide similar results.

In some embodiments, the PVP portion of the polymer blend may comprise from about 5% to about 50% by weight of the polymer blend, in certain embodiments from about 15% to 20%, and in other embodiments from about 25% to 40%. It is contemplated that PVP of various molecular weights may be used. For example, in some embodiments, the molecular weight of the PVP used may be from about 25,000 daltons to about 5,000,000 daltons, in certain embodiments from about 50,000 daltons to about 2,000,000 daltons, and in other embodiments from 6,000,000 daltons to about 10,000,000 daltons.

The term 'surface-active group' and 'surface-active end group' as used herein are broad terms and are used in their ordinary sense, including, without limitation, surface-active oligomers or other surface-active moieties having surface-active properties, such as alkyl groups, which preferentially migrate towards a surface of a membrane formed there from. Surface-active groups preferentially migrate toward air (e.g., driven by thermodynamic properties during membrane formation). In some embodiments, the surface-active groups are covalently bonded to the base polymer during synthesis. In some preferred embodiments, surface-active groups may include silicone, sulfonate, fluorine, polyethylene oxide, hydrocarbon groups, and the like. The surface activity (e.g., chemistry, properties) of a membrane domain including a surface-active group-containing polymer reflects the surface activity of the surface-active groups rather than that of the base polymer. In other words, surface-active groups control the chemistry at the surface (e.g., the biological contacting surface) of the membrane without compromising the bulk properties of the base polymer. The surface-active groups of the preferred embodiments are selected for desirable surface properties, for example, non-constant noise-blocking ability, break-in time (reduced), ability to repel charged species, cationic or anionic blocking, or the like. In some preferred embodiments, the surface-active groups are located on one or more ends of the polymer backbone, and referred to as surface-active end groups, wherein the surface-active end groups are believed to more readily migrate to the surface of the bioprotective domain/layer formed from the surface-active group-containing polymer in some circumstances.

Figure 4A:
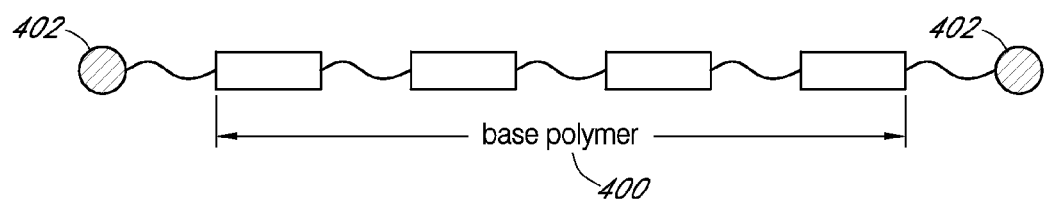
FIG. 4A is a schematic view of a base polymer containing surface-active end groups in one embodiment.

FIG. 4A is a schematic view of a base polymer 400 having surface-active end groups in one embodiment. In some preferred embodiments, the surface-active moieties 402 are restricted to the termini of the linear or branched base polymer(s) 400 such that changes to the base polymer's bulk properties are minimized. Because the polymers couple end groups to the backbone polymer during synthesis, the polymer backbone retains its strength and processability. The utility of surface-active end groups is based on their ability to accumulate at the surface of a formed article made from the surface-active end group-containing polymer. Such accumulation is driven by the minimization of interfacial energy of the system, which occurs as a result of it.

Figure 4B:
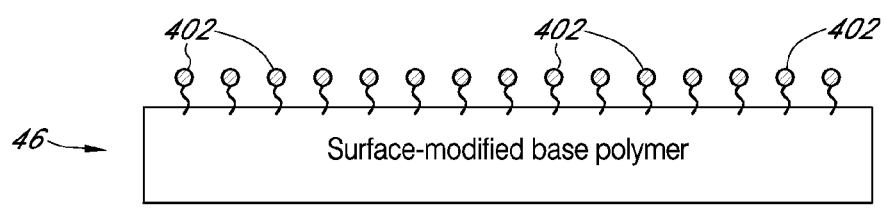
FIG. 4B is a schematic view of a bioprotective domain, showing an interface in a biological environment (e.g., interstitial space or vascular space).

FIG. 4B is a schematic view of a bioprotective domain, showing an interface in a biological environment (e.g., interstitial space or vascular space). The preferred surface-active group-containing polymer is shown fabricated as a membrane 46, wherein the surface-active end groups have migrated to the surface of the base polymer. While not wishing to be bound by theory, it is believed that this surface is developed by surface-energy-reducing migrations of the surface-active end groups to the air-facing surface during membrane fabrication. It is also believed that the hydrophobicity and mobility of the end groups relative to backbone groups facilitate the formation of this uniform over layer by the surface-active (end) blocks.

In some embodiments, the bioprotective domain 46 is formed from a polymer containing silicone as the surface-active group, for example, a polyurethane containing silicone end group(s). Some embodiments include a continuous analyte sensor configured for insertion into a host, wherein the sensor has a membrane located over the sensing mechanism, which includes a polyurethane comprising silicone end groups configured to substantially block the effect of non-constant noise-causing species on the sensor signal, as described in more detail elsewhere herein. In some embodiments, the polymer includes about 10%, 11%, 12%, 13%, 14%, 15%, 16%, 17%, 18%, 19%, 20%, 21%, 22%, 23%, 24%, 25%, 26%, 27%, 28%, 29%, 30%, to about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54% or 55% silicone by weight. In certain embodiments, the silicone (e.g., a precursor such as PDMS) has a molecular weight from about 500 to about 10,000 daltons, preferably at least about 200 daltons. In some embodiments, the base polymer includes at least about 10% silicone by weight, and preferably from about 19% to about 40% silicone by weight. These ranges are believed to provide an advantageous balance of noise-reducing functionality, while maintaining sufficient glucose permeability in embodiments wherein the sensor is a glucose sensor, for example.

In some embodiments, the bioprotective domain is formed from a polymer containing fluorine as a surface-active group, for example, a polyurethane that contains a fluorine end groups. In preferred embodiments, the polymer includes from about 1% to about 25% fluorine by weight. Some embodiments include a continuous analyte sensor configured for insertion into a host, wherein the sensor has a membrane located over the sensing mechanism, wherein the membrane includes a polyurethane containing fluorine surface-active groups, and wherein the membrane is configured and arranged to reduce a break-in time of a sensor as compared to a membrane formed from a similar base polymer without the surface-active group(s). For example, in preferred embodiments, a glucose sensor having a bioprotective domain of the preferred embodiments has a response time (e.g., $t_{90}$) of less than 120 seconds, in certain embodiments less than 60 seconds, and in still other embodiments less than about 45, 30, 20, or 10 seconds (across a physiological range of glucose concentration).

In some embodiments, the bioprotective domain may be formed from a polymer that contains sulfonate as a surface-active group, for example, a polyurethane containing sulfonate end group(s). In some embodiments, the continuous analyte sensor configured for insertion into a host may include a membrane located over the sensing mechanism, wherein the membrane includes a polymer that contains sulfonate as a surface-active group, and is configured to repel charged species, for example, due to the net negative charge of the sulfonated groups.

In some embodiments, a blend of two or more (e.g., two, three, four, five, or more) surface-active group-containing polymers is used to form a bioprotective membrane domain. For example, by blending a polyurethane with silicone end groups and a polyurethane with fluorine end groups, and forming a bioprotective membrane domain from that blend, a sensor can be configured to substantially block non-constant noise-causing species and reduce the sensor's $t_{90}$, as described in more detail elsewhere herein. Similarly, by blending a polyurethane containing silicone end groups, a polyurethane containing fluorine end groups, and a polyurethane containing sulfonate end groups, and forming a bioprotective membrane domain from that blend, a sensor can be configured to substantially block non-constant noise-causing species, to reduce the sensor's break-in time and to repel charged species, as described in more detail above. Although in some embodiments, blending of two or more surface-active group-containing polymers is used, in other embodiments, a single component polymer can be formed by synthesizing two or more surface-active groups with a base polymer to achieve similarly advantageous surface properties; however, blending may be preferred in some embodiments for ease of manufacture.

As described in Example 8 below, in some embodiments, sensors employing a bioprotective domain have not only demonstrated greater levels of overall accuracy, but also greater levels of accuracy at low glucose concentration levels (e.g., at glucose concentration levels from about 40 mg/dL to about 80 mg/dL), as compared to conventional continuous glucose sensors. The ability of certain sensor embodiments, incorporating a bioprotective domain, to measure accurately at low glucose concentration levels can not only be valuable, but at times can be critical to the user of the device. Whereas there is typically little immediate danger from hyperglycemia, there can be very real immediate danger from hypoglycemia. Severe hypoglycemia can lead to mental disorientation, unconsciousness, seizure, accidents, physical injury, and sometimes death. Thus, while there can be a large level of clinical tolerance for sensor errors at the euglycemic range and even at the hyperglycemic range, the tolerance level at low glucose concentration levels is generally much lower. Accordingly, it may be desirable to provide a sensor that can meet higher accuracy standards, particularly in the hypoglycemic range, in order to provide accurate feedback for appropriate and timely treatment decision.

Conventional sensors typically do not perform as accurately in the hypoglycemic range as they do in higher glucose concentration ranges. When a sensor is calibrated, the sensor is generally calibrated across an entire glucose concentration range. As a result, because the conversion function, as derived from the calibration and used to convert signal amplitude (counts) to glucose concentration, may contain error (e.g., because of inaccurate calibration or because of imperfection in the ideal linear relationship between the signal amplitude and actual glucose concentration), an inherent measurement inaccuracy may exist at any glucose concentration level. What's more, errors at low glucose concentrations can often be magnified, as compared to errors at other glucose concentration ranges. Accordingly, a sensor's overall accuracy (e.g., as measured in terms of mean absolute relative difference) is typically not representative of the sensor's accuracy at hypoglycemic levels, and in fact, is typically less accurate at these levels. While not wishing to be bound by theory, it is believed that this phenomenon occurs with conventional sensors in part because at low glucose concentrations a smaller glucose signal amplitude is generated (as compared to the signal amplitude associated with normal or high glucose concentrations), while the baseline signal (or background or constant noise) remain substantially constant and thus can in certain circumstances proportionally overwhelm the smaller glucose signal amplitude. Thus, the glucose-signal-to-baseline-signal ratio at a low glucose concentration is typically less than the glucose-signal-to-baseline-signal ratio at a high glucose concentration.

While not wishing to be bound by theory, it is believed that in certain types of sensors, accuracy in the hypoglycemic range may be improved by reducing the level of baseline signal without altering the sensitivity. This minimization of the baseline signal provides a gain in the glucose-signal-to-baseline-signal ratio, particularly at the hypoglycemic range. In turn, ceteris paribus, a much more accurate representation of the glucose signal is obtained, as the effect of the background signal, which may contain inaccuracies for the reasons described above, on the total signal is reduced. By way of example, a 5% error in the baseline signal will typically cause a higher level of inaccuracy and signal distortion in a sensor with a low glucose-signal-to-baseline-signal ratio than that of a sensor with a high glucose-signal-to-baseline-signal.

Figure 10A:
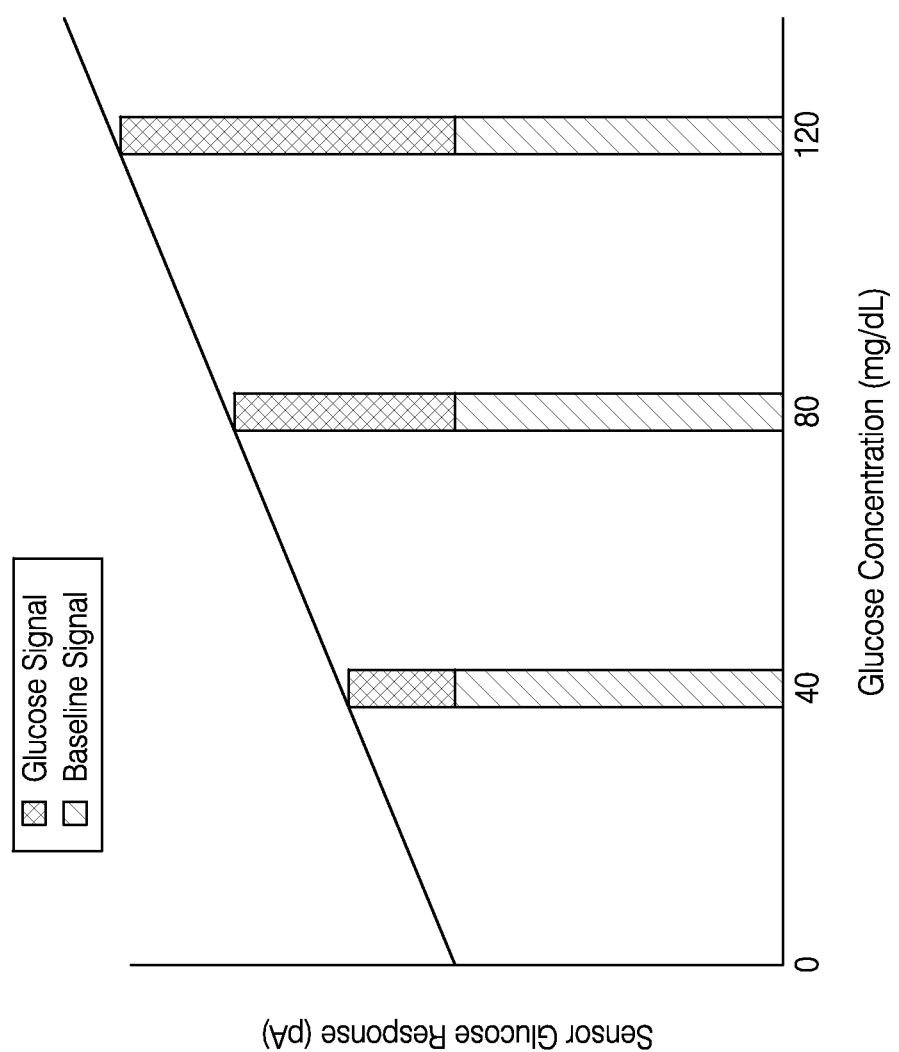
FIG. 10A is a graph illustrating the conversion function of a sensor with a substantial background signal.
Figure 10B:
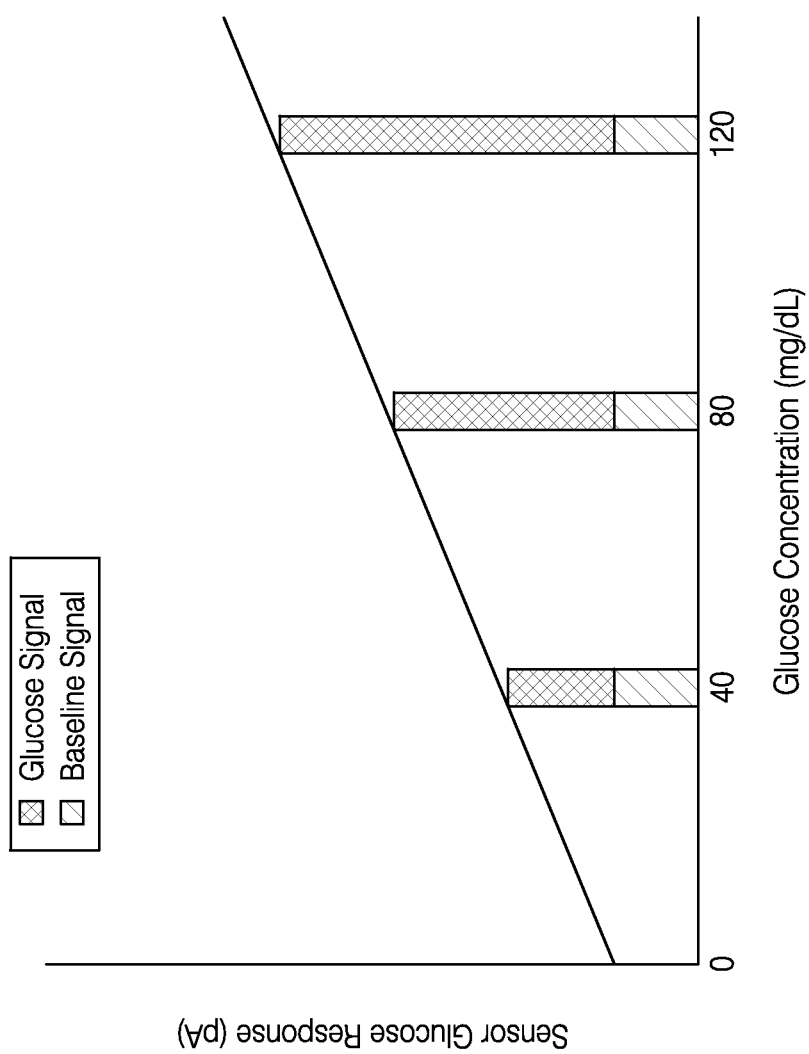
FIG. 10B is a graph illustrating the conversion function of a sensor similar to that associated with FIG. 10A, but with a substantial reduction in the background signal.

A comparison of FIGS. 10A with 10B (both of which are not necessarily drawn to scale) further illustrates this phenomenon. FIG. 10A displays the conversion function of a sensor with a high background signal, while FIG. 10B displays the conversion function of a sensor similar to the sensor associated with FIG. 10A, but with a low background signal. As illustrated, the sensitivities (i.e., the slopes of the conversion function as measured in units of mg/dLpA) of the two sensors are the same. While not wishing to be bound by theory, it is believed that the sensor associated with FIG. 10B, ceteris paribus, is capable of achieving better overall accuracy (and particularly better accuracy at the hypoglycemic range) than the sensor associated with FIG. 10A, because of its better glucose-signal-to-baseline-signal ratio. As can be realized from comparing FIG. 10A with FIG. 10B, the difference in the glucose-signal-to-baseline-signal ratios, between the two sensors, is particularly pronounced in the hypoglycemic range, and less so in the euglycemic range, and even less so in the hyperglycemic range. Accordingly, while not wishing to be bound by theory, it is believed that sensor accuracy improvement resulting from a reduction in baseline signal may in certain circumstances be greater at the hypoglycemic range than at other ranges of higher glucose concentration levels.

In some embodiments, sensor accuracy may be improved by using a membrane with a bioprotective layer that unexpectedly and substantially reduces the baseline signal, thereby providing not only better overall accuracy, but also better accuracy at the hypoglycemic range.

Membrane Fabrication

Preferably, polymers of the preferred embodiments may be processed by solution-based techniques such as spraying, dipping, casting, electrospinning, vapor deposition, spin coating, coating, and the like. Water-based polymer emulsions can be fabricated to form membranes by methods similar to those used for solvent-based materials. In both cases the evaporation of a volatile liquid (e.g. organic solvent or water) leaves behind a film of the polymer. Cross-linking of the deposited film may be performed through the use of multi-functional reactive ingredients by a number of methods well known to those skilled in the art. The liquid system may cure by heat, moisture, high-energy radiation, ultraviolet light, or by completing the reaction, which produces the final polymer in a mold or on a substrate to be coated.

Domains that include at least two surface-active group-containing polymers may be made using any of the methods of forming polymer blends known in the art. In one exemplary embodiment, a solution of a polyurethane containing silicone end groups is mixed with a solution of a polyurethane containing fluorine end groups (e.g., wherein the solutions include the polymer dissolved in a suitable solvent such as acetone, ethyl alcohol, DMAC, THF, 2-butanone, and the like). The mixture can then be drawn into a film or applied to a surface using any method known in the art (e.g., spraying, painting, dip coating, vapor depositing, molding, 3-D printing, lithographic techniques (e.g., photolithograph), micro- and nano-pipetting printing techniques, etc.). The mixture can then be cured under high temperature (e.g., 50-150° C.). Other suitable curing methods may include ultraviolet or gamma radiation, for example.

Some amount of cross-linking agent can also be included in the mixture to induce cross-linking between polymer molecules. Non-limiting examples of suitable cross-linking agents include isocyanate, carbodiimide, gluteraldehyde or other aldehydes, epoxy, acrylates, free-radical based agents, ethylene glycol diglycidyl ether (EGDE), poly(ethylene glycol) diglycidyl ether (PEGDE), or dicumyl peroxide (DCP). In one embodiment, from about 0.1% to about 15% w/w of cross-linking agent is added relative to the total dry weights of cross-linking agent and polymers added when blending the ingredients (in one example, about 1% to about 10%). During the curing process, substantially all of the cross-linking agent is believed to react, leaving substantially no detectable unreacted cross-linking agent in the final film.

In some embodiments, the bioprotective domain 46 is positioned most distally to the sensing region such that its outer most domain contacts a biological fluid when inserted in vivo. In some embodiments, the bioprotective domain is resistant to cellular attachment, impermeable to cells, and may be composed of a biostable material. While not wishing to be bound by theory, it is believed that when the bioprotective domain 46 is resistant to cellular attachment (for example, attachment by inflammatory cells, such as macrophages, which are therefore kept a sufficient distance from other domains, for example, the enzyme domain), hypochlorite and other oxidizing species are short-lived chemical species in vivo, and biodegradation does not generally occur. Additionally, the materials preferred for forming the bioprotective domain 46 may be resistant to the effects of these oxidative species and have thus been termed biodurable. In some embodiments, the bioprotective domain controls the flux of oxygen and other analytes (for example, glucose) to the underlying enzyme domain (e.g., wherein the functionality of the diffusion resistance domain is built-into the bioprotective domain such that a separate diffusion resistance domain is not required).

In certain embodiments, the thickness of the bioprotective domain may be from about 0.1, 0.5, 1, 2, 4, 6, 8 microns or less to about 10, 15, 20, 30, 40, 50, 75, 100, 125, 150, 175, 200 or 250 microns or more. In some of these embodiments, the thickness of the bioprotective domain may be in certain embodiments from about 1 to about 5 microns, and in other embodiments from about 2 to about 7 microns. In other embodiments, the bioprotective domain may be from about 20 or 25 microns to about 50, 55, or 60 microns thick. In some embodiments, the glucose sensor may be configured for transcutaneous or short-term subcutaneous implantation, and may have a thickness from about 0.5 microns to about 8 microns, or in certain embodiments from about 4 microns to about 6 microns. In one glucose sensor configured for fluid communication with a host's circulatory system, the thickness may be from about 1.5 microns to about 25 microns, and in certain embodiments from about 3 to about 15 microns. It is also contemplated that in some embodiments, the bioprotective layer or any other layer of the electrode may have a thickness that is consistent, but in other embodiments, the thickness may vary. For example, in some embodiments, the thickness of the bioprotective layer may vary along the longitudinal axis of the electrode end.

Diffusion Resistance Domain

In some embodiments, a diffusion resistance domain 44, also referred to as a diffusion resistance layer, may be used and is situated more proximal to the implantable device relative to the bioprotective domain. In some embodiments, the functionality of the diffusion resistance domain may be built into the bioprotective domain that comprises the surface-active group-containing base polymer. Accordingly, the description herein of the diffusion resistance domain may also apply to the bioprotective domain. The diffusion resistance domain serves to control the flux of oxygen and other analytes (for example, glucose) to the underlying enzyme domain. There typically exists a molar excess of glucose in a body relative to the amount of oxygen in interstitial fluid or blood, e.g., for every free oxygen molecule in extracellular fluid, there are typically more than 100 glucose molecules present (see Updike et al., *Diabetes Care* 5:207-21 (1982)). To achieve accurate sensor measurements of glucose concentration, the amount of oxygen present for the glucose-oxidase-catalyzed reaction has to be greater than that of glucose. Otherwise, an oxygen limiting reaction, instead of a glucose limiting reaction, may occur, especially in high glucose concentration levels. More specifically, when a glucose-monitoring reaction is oxygen-limited, linearity is not achieved above minimal concentrations of glucose. Without a semipermeable membrane situated over the enzyme domain to control the flux of glucose and oxygen, a linear response to glucose levels can be obtained only up to about 40 mg/dL. However, in a clinical setting, a linear response to glucose levels is desirable up to at least about 500 mg/dL.

The diffusion resistance domain 44 includes a semipermeable membrane that controls the flux of oxygen and glucose to the underlying enzyme domain 44, preferably rendering oxygen in non-rate-limiting excess. As a result, the upper limit of linearity of glucose measurement is extended to a much higher value than that which is achieved without the diffusion resistance domain. In some embodiments, the diffusion resistance domain exhibits an oxygen-to-glucose permeability ratio of approximately 200:1, but in other embodiments the oxygen-to-glucose permeability ratio may be approximately 100:1, 125:1, 130:1, 135:1, 150:1, 175:1, 225:1, 250:1, 275:1, 300:1, or 500:1. As a result of the high oxygen-to-glucose permeability ratio, one-dimensional reactant diffusion may provide sufficient excess oxygen at all reasonable glucose and oxygen concentrations found in the subcutaneous matrix (See Rhodes et al., *Anal. Chem.*, 66:1520-1529 (1994)). In some embodiments, a lower ratio of oxygen-to-glucose can be sufficient to provide excess oxygen by using a high oxygen soluble domain (for example, a silicone material) to enhance the supply/transport of oxygen to the enzyme membrane or electroactive surfaces. By enhancing the oxygen supply through the use of a silicone composition, for example, glucose concentration can be less of a limiting factor. In other words, if more oxygen is supplied to the enzyme or electroactive surfaces, then more glucose can also be supplied to the enzyme without creating an oxygen rate-limiting excess.

In some embodiments, the diffusion resistance domain is formed of a base polymer synthesized to include a polyurethane membrane with both hydrophilic and hydrophobic regions to control the diffusion of glucose and oxygen to an analyte sensor. A suitable hydrophobic polymer component may be a polyurethane or polyether urethane urea. Polyurethane is a polymer produced by the condensation reaction of a diisocyanate and a difunctional hydroxyl-containing material. A polyurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the diffusion resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In one embodiment of a polyurethane-based resistance domain, the hydrophilic polymer component is polyethylene oxide. For example, one useful hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

Alternatively, in some embodiments, the resistance domain may comprise a combination of a base polymer (e.g., polyurethane) and one or more hydrophilic polymers (e.g., PVA, PEG, polyacrylamide, acetates, PEO, PEA, PVP, and variations thereof). It is contemplated that any of a variety of combination of polymers may be used to yield a blend with desired glucose, oxygen, and interference permeability properties. For example, in some embodiments, the resistance domain may be formed from a blend of a silicone polycarbonate-urethane base polymer and a PVP hydrophilic polymer, but in other embodiments, a blend of a polyurethane, or another base polymer, and one or more hydrophilic polymers may be used instead. In some of the embodiments involving the use of PVP, the PVP portion of the polymer blend may comprise from about 5% to about 50% by weight of the polymer blend, in certain embodiments from about 15% to 20%, and in other embodiments from about 25% to 40%. It is contemplated that PVP of various molecular weights may be used. For example, in some embodiments, the molecular weight of the PVP used may be from about 25,000 daltons to about 5,000,000 daltons, in certain embodiments from about 50,000 daltons to about 2,000,000 daltons, and in other embodiments from 6,000,000 daltons to about 10,000,000 daltons.

In some embodiments, the diffusion resistance domain 44 can be formed as a unitary structure with the bioprotective domain 46; that is, the inherent properties of the diffusion resistance domain 44 are incorporated into bioprotective domain 46 such that the bioprotective domain 46 functions as a diffusion resistance domain 44.

In certain embodiments, the thickness of the resistance domain may be from about 0.05 microns or less to about 200 microns or more. In some of these embodiments, the thickness of the resistance domain may be from about 0.05, 0.1, 0.15, 0.2, 0.25, 0.3, 0.35, 0.4, 0.45, 0.5, 1, 1.5, 2, 2.5, 3, 3.5, 4, 6, 8 microns to about 9, 10, 11, 12, 13, 14, 15, 16, 17, 18, 19, 19.5, 20, 30, 40, 50, 60, 70, 75, 80, 85, 90, 95, or 100 microns. In some embodiments, the thickness of the resistance domain is from about 2, 2.5 or 3 microns to about 3.5, 4, 4.5, or 5 microns in the case of a transcutaneously implanted sensor or from about 20 or 25 microns to about 40 or 50 microns in the case of a wholly implanted sensor.

Enzyme Domain

In some embodiments, an enzyme domain 42, also referred to as the enzyme layer, may be used and is situated less distal from the electrochemically reactive surfaces than the diffusion resistance domain 44. The enzyme domain comprises a catalyst configured to react with an analyte. In one embodiment, the enzyme domain is an immobilized enzyme domain 42 including glucose oxidase. In other embodiments, the enzyme domain 42 can be impregnated with other oxidases, for example, galactose oxidase, cholesterol oxidase, amino acid oxidase, alcohol oxidase, lactate oxidase, or uricase. For example, for an enzyme-based electrochemical glucose sensor to perform well, the sensor's response should neither be limited by enzyme activity nor cofactor concentration.

In some embodiments, the catalyst (enzyme) can be impregnated or otherwise immobilized into the bioprotective or diffusion resistance domain such that a separate enzyme domain 42 is not required (e.g., wherein a unitary domain is provided including the functionality of the bioprotective domain, diffusion resistance domain, and enzyme domain). In some embodiments, the enzyme domain 42 is formed from a polyurethane, for example, aqueous dispersions of colloidal polyurethane polymers including the enzyme.

In some embodiments, the thickness of the enzyme domain may be from about 0.01, 0.05, 0.6, 0.7, or 0.8 microns to about 1, 1.2, 1.4, 1.5, 1.6, 1.8, 2, 2.1, 2.2, 2.5, 3, 4, 5, 10, 20, 30 40, 50, 60, 70, 80, 90, or 100 microns. In more preferred embodiments, the thickness of the enzyme domain is from about 0.05, 0.1, 0.15, 0.2, 0.25, 0.3, 0.35, 0.4, 0.45, 0.5, 1, 1.5, 2, 2.5, 3, 4, or 5 microns to about 6, 7, 8, 9, 10, 11, 12, 13, 14, 15, 16, 17, 18, 19, 19.5, 20, 25, or 30 microns. In even more preferred embodiments, the thickness of the enzyme domain is from about 2, 2.5, or 3 microns to about 3.5, 4, 4.5, or 5 microns in the case of a transcutaneously implanted sensor or from about 6, 7, or 8 microns to about 9, 10, 11, or 12 microns in the case of a wholly implanted sensor.

Interference Domain

It is contemplated that in some embodiments, such as the embodiment illustrated in FIG. 2B, an optional interference domain 40, also referred to as the interference layer, may be provided, in addition to the bioprotective domain and the enzyme domain. The interference domain 40 may substantially reduce the permeation of one or more interferents into the electrochemically reactive surfaces. Preferably, the interference domain 40 is configured to be much less permeable to one or more of the interferents than to the measured species. It is also contemplated that in some embodiments, where interferent blocking may be provided by the bioprotective domain (e.g., via a surface-active group-containing polymer of the bioprotective domain), a separate interference domain may not be used.

In some embodiments, the interference domain is formed from a silicone-containing polymer, such as a polyurethane containing silicone, or a silicone polymer. While not wishing to be bound by theory, it is believed that, in order for an enzyme-based glucose sensor to function properly, glucose would not have to permeate the interference layer, where the interference domain is located more proximal to the electroactive surfaces than the enzyme domain. Accordingly, in some embodiments, a silicone-containing interference domain, comprising a greater percentage of silicone by weight than the bioprotective domain, may be used without substantially affecting glucose concentration measurements. For example, in some embodiments, the silicone-containing interference domain may comprise a polymer with a high percentage of silicone (e.g., from about 25%, 30%, 35%, 40%, 45%, or 50% to about 60%, 70%, 80%, 90% or 95%).

In one embodiment, the interference domain may include ionic components incorporated into a polymeric matrix to reduce the permeability of the interference domain to ionic interferents having the same charge as the ionic components. In another embodiment, the interference domain may include a catalyst (for example, peroxidase) for catalyzing a reaction that removes interferents. U.S. Pat. No. 6,413,396 and U.S. Pat. No. 6,565,509 disclose methods and materials for eliminating interfering species.

In certain embodiments, the interference domain may include a thin membrane that is designed to limit diffusion of certain species, for example, those greater than 34 kD in molecular weight. In these embodiments, the interference domain permits certain substances (for example, hydrogen peroxide) that are to be measured by the electrodes to pass through, and prevents passage of other substances, such as potentially interfering substances. In one embodiment, the interference domain is constructed of polyurethane. In an alternative embodiment, the interference domain comprises a high oxygen soluble polymer, such as silicone.

In some embodiments, the interference domain is formed from one or more cellulosic derivatives. In general, cellulosic derivatives may include polymers such as cellulose acetate, cellulose acetate butyrate, 2-hydroxyethyl cellulose, cellulose acetate phthalate, cellulose acetate propionate, cellulose acetate trimellitate, or blends and combinations thereof.

In some alternative embodiments, other polymer types that can be utilized as a base material for the interference domain include polyurethanes, polymers having pendant ionic groups, and polymers having controlled pore size, for example. In one such alternative embodiment, the interference domain includes a thin, hydrophobic membrane that is non-swellable and restricts diffusion of low molecular weight species. The interference domain is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S. Pat. No. 7,074,307, U.S. Patent Publication No. US-2005-0176136-A1, U.S. Pat. No. 7,081,195, and U.S. Patent Publication No. US-2005-0143635-A1, each of which is incorporated by reference herein in its entirety.

It is contemplated that in some embodiments, the thickness of the interference domain may be from about 0.01 microns or less to about 20 microns or more. In some of these embodiments, the thickness of the interference domain may be from about 0.01, 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns. In some of these embodiments, the thickness of the interference domain may be from about 0.2, 0.4, 0.5, or 0.6, microns to about 0.8, 0.9, 1, 1.5, 2, 3, or 4 microns.

In general, the membrane system may be formed or deposited on the exposed electroactive surfaces (e.g., one or more of the working and reference electrodes) using known thin film techniques (for example, casting, spray coating, drawing down, electro-depositing, dip coating, and the like), however casting or other known application techniques can also be utilized. In some embodiments, the interference domain may be deposited by spray or dip coating. In one exemplary embodiment, the interference domain is formed by dip coating the sensor into an interference domain solution using an insertion rate of from about 0.5 inch/min to about 60 inches/min, and in certain embodiments about 1 inch/min; a dwell time of from about 0.01 minutes to about 2 minutes, and in certain embodiments about 1 minute; and a withdrawal rate of from about 0.5 inch/minute to about 60 inches/minute, and in certain embodiments about 1 inch/minute; and curing (drying) the domain from about 1 minute to about 14 hours, and in certain embodiments from about 3 minutes to about 15 minutes (and can be accomplished at room temperature or under vacuum (e.g., 20 to 30 mmHg)). In one exemplary embodiment including a cellulose acetate butyrate interference domain, a 3-minute cure (i.e., dry) time is used between each layer applied. In another exemplary embodiment employing a cellulose acetate interference domain, a 15 minute cure time is used between each layer applied.

In some embodiments, the dip process can be repeated at least one time and up to 10 times or more. In other embodiments, only one dip is preferred. The preferred number of repeated dip processes may depend upon the cellulosic derivative(s) used, their concentration, conditions during deposition (e.g., dipping) and the desired thickness (e.g., sufficient thickness to provide functional blocking of certain interferents), and the like. In one embodiment, an interference domain is formed from three layers of cellulose acetate butyrate. In another embodiment, an interference domain is formed from 10 layers of cellulose acetate. In yet another embodiment, an interference domain is formed from 1 layer of a blend of cellulose acetate and cellulose acetate butyrate. In alternative embodiments, the interference domain can be formed using any known method and combination of cellulose acetate and cellulose acetate butyrate, as will be appreciated by one skilled in the art.

Electrode Domain

It is contemplated that in some embodiments, such as the embodiment illustrated in FIG. 2C, an optional electrode domain 36, also referred to as the electrode layer, may be provided, in addition to the bioprotective domain and the enzyme domain; however, in other embodiments, the functionality of the electrode domain may be incorporated into the bioprotective domain so as to provide a unitary domain that includes the functionality of the bioprotective domain, diffusion resistance domain, enzyme domain, and electrode domain.

In some embodiments, the electrode domain is located most proximal to the electrochemically reactive surfaces. To facilitate electrochemical reaction, the electrode domain may include a semipermeable coating that maintains hydrophilicity at the electrochemically reactive surfaces of the sensor interface. The electrode domain can enhance the stability of an adjacent domain by protecting and supporting the material that makes up the adjacent domain. The electrode domain may also assist in stabilizing the operation of the device by overcoming electrode start-up problems and drifting problems caused by inadequate electrolyte. The buffered electrolyte solution contained in the electrode domain may also protect against pH-mediated damage that can result from the formation of a large pH gradient between the substantially hydrophobic interference domain and the electrodes due to the electrochemical activity of the electrodes.

In some embodiments, the electrode domain includes a flexible, water-swellable, substantially solid gel-like film (e.g., a hydrogel) having a 'dry film' thickness of from about 0.05 microns to about 100 microns, and in certain embodiments from about 0.05, 0.1, 0.15, 0.2, 0.25, 0.3, 0.35, 0.4, 0.45, 0.5, 1 microns to about 1.5, 2, 2.5, 3, or 3.5, 4, 4.5, 5, 6, 6.5, 7, 7.5, 8, 8.5, 9, 9.5, 10, 10.5, 11, 11.5, 12, 13, 14, 15, 16, 17, 18, 19, 19.5, 20, 30, 40, 50, 60, 70, 80, 90, or 100 microns. In some embodiments, the thickness of the electrode domain may be from about 2, 2.5 or 3 microns to about 3.5, 4, 4.5, or 5 microns in the case of a transcutaneously implanted sensor, or from about 6, 7, or 8 microns to about 9, 10, 11, or 12 microns in the case of a wholly implanted sensor. The term 'dry film thickness' as used herein is a broad term, and is to be given its ordinary and customary meaning to a person of ordinary skill in the art (and is not to be limited to a special or customized meaning), and refers without limitation to the thickness of a cured film cast from a coating formulation onto the surface of the membrane by standard coating techniques. The coating formulation may comprise a premix of film-forming polymers and a cross-linking agent and may be curable upon the application of moderate heat.

In certain embodiments, the electrode domain may be formed of a curable mixture of a urethane polymer and a hydrophilic polymer. In some of these embodiments, coatings are formed of a polyurethane polymer having anionic carboxylate functional groups and non-ionic hydrophilic polyether segments, which are crosslinked in the presence of polyvinylpyrrolidone and cured at a moderate temperature of about 50° C.

Particularly suitable for this purpose are aqueous dispersions of fully-reacted colloidal polyurethane polymers having cross-linkable carboxyl functionality (e.g., BAYBOND®; Mobay Corporation). These polymers are supplied in dispersion grades having a polycarbonate-polyurethane backbone containing carboxylate groups identified as XW-121 and XW-123; and a polyester-polyurethane backbone containing carboxylate groups, identified as XW-110-2. In some embodiments, BAYBOND® 123, an aqueous anionic dispersion of an aliphate polycarbonate urethane polymer sold as a 35 weight percent solution in water and co-solvent N-methyl-2-pyrrolidone, may be used.

In some embodiments, the electrode domain is formed from a hydrophilic polymer that renders the electrode domain substantially more hydrophilic than an overlying domain (e.g., interference domain, enzyme domain). Such hydrophilic polymers may include, a polyamide, a polylactone, a polyimide, a polylactam, a functionalized polyamide, a functionalized polylactone, a functionalized polyimide, a functionalized polylactam or combinations thereof, for example.

In some embodiments, the electrode domain is formed primarily from a hydrophilic polymer, and in some of these embodiments, the electrode domain is formed substantially from PVP. PVP is a hydrophilic water-soluble polymer and is available commercially in a range of viscosity grades and average molecular weights ranging from about 18,000 to about 500,000, under the PVP K® homopolymer series by BASF Wyandotte and by GAF Corporation. In certain embodiments, a PVP homopolymer having an average molecular weight of about 360,000 identified as PVP-K90 (BASF Wyandotte) may be used to form the electrode domain. Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

In certain embodiments, the electrode domain is formed entirely from a hydrophilic polymer. Useful hydrophilic polymers contemplated include, but are not limited to, poly-N-vinylpyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinylimidazole, poly-N,N-dimethylacrylamide, polyvinyl alcohol, polyacrylic acid, polyethylene oxide, poly-2-ethyl-oxazoline, copolymers thereof and mixtures thereof. A blend of two or more hydrophilic polymers may be preferred in some embodiments.

It is contemplated that in certain embodiments, the hydrophilic polymer used may not be crosslinked, but in other embodiments, crosslinking may be used and achieved by any of a variety of methods, for example, by adding a crosslinking agent. In some embodiments, a polyurethane polymer may be crosslinked in the presence of PVP by preparing a premix of the polymers and adding a cross-linking agent just prior to the production of the membrane. Suitable cross-linking agents contemplated include, but are not limited to, carbodiimides (e.g., 1-ethyl-3-(3-dimethylaminopropyl)carbodiimide hydrochloride, UCARLNK®. XL-25 (Union Carbide)), epoxides and melamine/formaldehyde resins. Alternatively, it is also contemplated that cross-linking may be achieved by irradiation at a wavelength sufficient to promote crosslinking between the hydrophilic polymer molecules, which is believed to create a more tortuous diffusion path through the domain.

The flexibility and hardness of the coating can be varied as desired by varying the dry weight solids of the components in the coating formulation. The term 'dry weight solids' as used herein is a broad term, and is to be given its ordinary and customary meaning to a person of ordinary skill in the art (and is not to be limited to a special or customized meaning), and refers without limitation to the dry weight percent based on the total coating composition after the time the crosslinker is included. In one embodiment, a coating formulation can contain about 6 to about 20 dry weight percent, preferably about 8 dry weight percent, PVP; about 3 to about 10 dry weight percent, in certain embodiments about 5 dry weight percent cross-linking agent; and about 70 to about 91 weight percent, in certain embodiments about 87 weight percent of a polyurethane polymer, such as a polycarbonate-polyurethane polymer, for example. The reaction product of such a coating formulation is referred to herein as a water-swellable cross-linked matrix of polyurethane and PVP.

In some embodiments, underlying the electrode domain is an electrolyte phase that when hydrated is a free-fluid phase including a solution containing at least one compound, typically a soluble chloride salt, which conducts electric current. In one embodiment wherein the membrane system is used with a glucose sensor such as is described herein, the electrolyte phase flows over the electrodes and is in contact with the electrode domain. It is contemplated that certain embodiments may use any suitable electrolyte solution, including standard, commercially available solutions. Generally, the electrolyte phase can have the same osmotic pressure or a lower osmotic pressure than the sample being analyzed. In preferred embodiments, the electrolyte phase comprises normal saline.

Bioactive Agents

It is contemplated that any of a variety of bioactive (therapeutic) agents can be used with the analyte sensor systems described herein, such as the analyte sensor system shown in FIG. 1. In some embodiments, the bioactive agent is an anticoagulant. The term 'anticoagulant' as used herein is a broad term, and is to be given its ordinary and customary meaning to a person of ordinary skill in the art (and is not to be limited to a special or customized meaning), and refers without limitation to a substance the prevents coagulation (e.g., minimizes, reduces, or stops clotting of blood). In these embodiments, the anticoagulant included in the analyte sensor system may prevent coagulation within or on the sensor. Suitable anticoagulants for incorporation into the sensor system include, but are not limited to, vitamin K antagonists (e.g., Acenocoumarol, Clorindione, Dicumarol (Dicoumarol), Diphenadione, Ethyl biscoumacetate, Phenprocoumon, Phenindione, Tioclomarol, or Warfarin), heparin group anticoagulants (e.g., Platelet aggregation inhibitors: Antithrombin III, Bemiparin, Dalteparin, Danaparoid, Enoxaparin, Heparin, Nadroparin, Parnaparin, Reviparin, Sulodexide, Tinzaparin), other platelet aggregation inhibitors (e.g., Abciximab, Acetylsalicylic acid (Aspirin), Aloxiprin, Beraprost, Ditazole, Carbasalate calcium, Cloricromen, Clopidogrel, Dipyridamole, Epoprostenol, Eptifibatide, Indobufen, Iloprost, Picotamide, Ticlopidine, Tirofiban, Treprostinil, Triflusal), enzymes (e.g., Alteplase, Ancrod, Anistreplase, Brinase, Drotrecogin alfa, Fibrinolysin, Protein C, Reteplase, Saruplase, Streptokinase, Tenecteplase, Urokinase), direct thrombin inhibitors (e.g., Argatroban, Bivalirudin, Desirudin, Lepirudin, Melagatran, Ximelagatran, other antithrombotics (e.g., Dabigatran, Defibrotide, Dermatan sulfate, Fondaparinux, Rivaroxaban), and the like.

In one embodiment, heparin is incorporated into the analyte sensor system, for example by dipping or spraying. While not wishing to be bound by theory, it is believed that heparin coated on the catheter or sensor may prevent aggregation and clotting of blood on the analyte sensor system, thereby preventing thromboembolization (e.g., prevention of blood flow by the thrombus or clot) or subsequent complications. In another embodiment, an antimicrobial is coated on the catheter (inner or outer diameter) or sensor.

In some embodiments, an antimicrobial agent may be incorporated into the analyte sensor system. The antimicrobial agents contemplated may include, but are not limited to, antibiotics, antiseptics, disinfectants and synthetic moieties, and combinations thereof, and other agents that are soluble in organic solvents such as alcohols, ketones, ethers, aldehydes, acetonitrile, acetic acid, methylene chloride and chloroform. The amount of each antimicrobial agent used to impregnate the medical device varies to some extent, but is at least of an effective concentration to inhibit the growth of bacterial and fungal organisms, such as staphylococci, gram-positive bacteria, gram-negative bacilli and *Candida*.

In some embodiments, an antibiotic may be incorporated into the analyte sensor system. Classes of antibiotics that can be used include tetracyclines (e.g., minocycline), rifamycins (e.g., rifampin), macrolides (e.g., erythromycin), penicillins (e.g., nafeillin), cephalosporins (e.g., cefazolin), other beta-lactam antibiotics (e.g., imipenem, aztreonam), aminoglycosides (e.g., gentamicin), chloramphenicol, sufonamides (e.g., sulfamethoxazole), glycopeptides (e.g., vancomycin), quinolones (e.g., ciprofloxacin), fusidic acid, trimethoprim, metronidazole, clindamycin, mupirocin, polyenes (e.g., amphotericin B), azoles (e.g., fluconazole), and beta-lactam inhibitors (e.g., sulbactam).

Examples of specific antibiotics that can be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin.

In some embodiments, an antiseptic or disinfectant may be incorporated into the analyte sensor system. Examples of antiseptics and disinfectants are hexachlorophene, cationic bisiguanides (e.g., chlorhexidine, cyclohexidine) iodine and iodophores (e.g., povidoneiodine), para-chloro-meta-xylenol, triclosan, furan medical preparations (e.g., nitrofurantoin, nitrofurazone), methenamine, aldehydes (glutaraldehyde, formaldehyde) and alcohols. Other examples of antiseptics and disinfectants will readily suggest themselves to those of ordinary skill in the art.

In some embodiments, an anti-barrier cell agent may be incorporated into the analyte sensor system. Anti-barrier cell agents may include compounds exhibiting affects on macrophages and foreign body giant cells (FBGCs). It is believed that anti-barrier cell agents prevent closure of the barrier to solute transport presented by macrophages and FBGCs at the device-tissue interface during FBC maturation. Anti-barrier cell agents may provide anti-inflammatory or immunosuppressive mechanisms that affect the wound healing process, for example, healing of the wound created by the incision into which an implantable device is inserted. Cyclosporine, which stimulates very high levels of neovascularization around biomaterials, can be incorporated into a bioprotective membrane of a preferred embodiment (see, e.g., U.S. Pat. No. 5,569,462 to Martinson et al.). Alternatively, Dexamethasone, which abates the intensity of the FBC response at the tissue-device interface, can be incorporated into a bioprotective membrane of a preferred embodiment. Alternatively, Rapamycin, which is a potent specific inhibitor of some macrophage inflammatory functions, can be incorporated into a bioprotective membrane of a preferred embodiment.

In some embodiments, an, anti-inflammatory agent may be incorporated into the analyte sensor system to reduce acute or chronic inflammation adjacent to the implant or to decrease the formation of a FBC capsule to reduce or prevent barrier cell layer formation, for example. Suitable anti-inflammatory agents include but are not limited to, for example, nonsteroidal anti-inflammatory drugs (NSAIDs) such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

In some embodiments, an immunosuppressive or immunomodulatory agent may be incorporated into the analyte sensor system in order to interfere directly with several key mechanisms necessary for involvement of different cellular elements in the inflammatory response. Suitable immunosuppressive and immunomodulatory agents include, but are not limited to, anti-proliferative, cell-cycle inhibitors, (for example, paclitaxel, cytochalasin D, infliximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), *E. coli* heat-labile enterotoxin, and advanced coatings.

In some embodiments, an anti-infective agent may be incorporated into the analyte sensor system. In general, anti-infective agents are substances capable of acting against infection by inhibiting the spread of an infectious agent or by killing the infectious agent outright, which can serve to reduce an immuno-response without an inflammatory response at the implant site, for example. Anti-infective agents include, but are not limited to, anthelmintics (e.g., mebendazole), antibiotics (e.g., aminoclycosides, gentamicin, neomycin, tobramycin), antifungal antibiotics (e.g., amphotericin b, fluconazole, griseofulvin, itraconazole, ketoconazole, nystatin, micatin, tolnaftate), cephalosporins (e.g., cefaclor, cefazolin, cefotaxime, ceftazidime, ceftriaxone, cefuroxime, cephalexin), beta-lactam antibiotics (e.g., cefotetan, meropenem), chloramphenicol, macrolides (e.g., azithromycin, clarithromycin, erythromycin), penicillins (e.g., penicillin G sodium salt, amoxicillin, ampicillin, dicloxacillin, nafcillin, piperacillin, ticarcillin), tetracyclines (e.g., doxycycline, minocycline, tetracycline), bacitracin, clindamycin, colistimethate sodium, polymyxin b sulfate, vancomycin, antivirals (e.g., acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine), quinolones (e.g., ciprofloxacin, levofloxacin); sulfonamides (e.g., sulfadiazine, sulfisoxazole), sulfones (e.g., dapsone), furazolidone, metronidazole, pentamidine, sulfanilamidum crystallinum, gatifloxacin, and sulfamethoxazole/trimethoprim.

In some embodiments, a vascularization agent may be incorporated into the analyte sensor system. Vascularization agents generally may include substances with direct or indirect angiogenic properties. In some cases, vascularization agents may additionally affect formation of barrier cells in vivo. By indirect angiogenesis, it is meant that the angiogenesis can be mediated through inflammatory or immune stimulatory pathways. It is not fully known how agents that induce local vascularization indirectly inhibit barrier-cell formation; however, while not wishing to be bound by theory, it is believed that some barrier-cell effects can result indirectly from the effects of vascularization agents.

Vascularization agents may provide mechanisms that promote neovascularization and accelerate wound healing around the membrane or minimize periods of ischemia by increasing vascularization close to the tissue-device interface. Sphingosine-1-Phosphate (S1P), a phospholipid possessing potent angiogenic activity, may be incorporated into the bioprotective membrane. Monobutyrin, a vasodilator and angiogenic lipid product of adipocytes, may also be incorporated into the bioprotective membrane. In another embodiment, an anti-sense molecule (for example, thrombospondin-2 anti-sense), which may increase vascularization, is incorporated into a bioprotective membrane.

Vascularization agents may provide mechanisms that promote inflammation, which is believed to cause accelerated neovascularization and wound healing in vivo. In one embodiment, a xenogenic carrier, for example, bovine collagen, which by its foreign nature invokes an immune response, stimulates neovascularization, and is incorporated into a bioprotective membrane of some embodiments. In another embodiment, Lipopolysaccharide, an immunostimulant, may be incorporated into a bioprotective membrane. In another embodiment, a protein, for example, α bone morphogenetic protein (BMP), which is known to modulate bone healing in tissue, may be incorporated into the bioprotective membrane.

In some embodiments, an angiogenic agent may be incorporated into the analyte sensor system. Angiogenic agents are substances capable of stimulating neovascularization, which can accelerate and sustain the development of a vascularized tissue bed at the tissue-device interface, for example. Angiogenic agents include, but are not limited to, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-β), Transforming Growth Factor Alpha (TGF-Alpha), Hepatocyte Growth Factor, Tumor Necrosis Factor-Alpha (TNFα), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Copper Sulphate, Estradiol, prostaglandins, cox inhibitors, endothelial cell binding agents (for example, decorin or vimentin), glenipin, hydrogen peroxide, nicotine, and Growth Hormone.

In some embodiments, a pro-inflammatory agent may be incorporated into the analyte sensor system. Pro-inflammatory agents are generally substances capable of stimulating an immune response in host tissue, which can accelerate or sustain formation of a mature vascularized tissue bed. For example, pro-inflammatory agents are generally irritants or other substances that induce chronic inflammation and chronic granular response at the wound-site. While not wishing to be bound by theory, it is believed that formation of high tissue granulation induces blood vessels, which supply an adequate or rich supply of analytes to the device-tissue interface. Pro-inflammatory agents include, but are not limited to, xenogenic carriers, Lipopolysaccharides, *S. aureus* peptidoglycan, and proteins.

These bioactive agents can be used alone or in combination. The bioactive agents can be dispersed throughout the material of the sensor, for example, incorporated into at least a portion of the membrane system, or incorporated into the device (e.g., housing) and adapted to diffuse through the membrane.

There are a variety of systems and methods by which a bioactive agent may be incorporated into the sensor membrane. In some embodiments, the bioactive agent may be incorporated at the time of manufacture of the membrane system. For example, the bioactive agent can be blended prior to curing the membrane system, or subsequent to membrane system manufacture, for example, by coating, imbibing, solvent-casting, or sorption of the bioactive agent into the membrane system. Although in some embodiments the bioactive agent is incorporated into the membrane system, in other embodiments the bioactive agent can be administered concurrently with, prior to, or after insertion of the device in vivo, for example, by oral administration, or locally, by subcutaneous injection near the implantation site. A combination of bioactive agent incorporated in the membrane system and bioactive agent administration locally or systemically can be preferred in certain embodiments.

In general, a bioactive agent can be incorporated into the membrane system, or incorporated into the device and adapted to diffuse therefrom, in order to modify the in vivo response of the host to the membrane. In some embodiments, the bioactive agent may be incorporated only into a portion of the membrane system adjacent to the sensing region of the device, over the entire surface of the device except over the sensing region, or any combination thereof, which can be helpful in controlling different mechanisms or stages of in vivo response (e.g., thrombus formation). In some alternative embodiments however, the bioactive agent may be incorporated into the device proximal to the membrane system, such that the bioactive agent diffuses through the membrane system to the host circulatory system.

The bioactive agent can include a carrier matrix, wherein the matrix includes one or more of collagen, a particulate matrix, a resorbable or non-resorbable matrix, a controlled-release matrix, or a gel. In some embodiments, the carrier matrix includes a reservoir, wherein a bioactive agent is encapsulated within a microcapsule. The carrier matrix can include a system in which a bioactive agent is physically entrapped within a polymer network. In some embodiments, the bioactive agent is cross-linked with the membrane system, while in others the bioactive agent is sorbed into the membrane system, for example, by adsorption, absorption, or imbibing. The bioactive agent can be deposited in or on the membrane system, for example, by coating, filling, or solvent casting. In certain embodiments, ionic and nonionic surfactants, detergents, micelles, emulsifiers, demulsifiers, stabilizers, aqueous and oleaginous carriers, solvents, preservatives, antioxidants, or buffering agents are used to incorporate the bioactive agent into the membrane system. The bioactive agent can be incorporated into a polymer using techniques such as described above, and the polymer can be used to form the membrane system, coatings on the membrane system, portions of the membrane system, or any portion of the sensor system.

The membrane system can be manufactured using techniques known in the art. The bioactive agent can be sorbed into the membrane system, for example, by soaking the membrane system for a length of time (for example, from about an hour or less to about a week, or more preferably from about 4, 8, 12, 16, or 20 hours to about 1, 2, 3, 4, 5, or 7 days).

The bioactive agent can be blended into uncured polymer prior to forming the membrane system. The membrane system is then cured and the bioactive agent thereby cross-linked or encapsulated within the polymer that forms the membrane system.

In yet another embodiment, microspheres are used to encapsulate the bioactive agent. The microspheres can be formed of biodegradable polymers, most preferably synthetic polymers or natural polymers such as proteins and polysaccharides. As used herein, the term polymer is used to refer to both to synthetic polymers and proteins. U.S. Pat. No. 6,281,015, discloses some systems and methods that can be used in conjunction with the preferred embodiments. In general, bioactive agents can be incorporated in (1) the polymer matrix forming the microspheres, (2) microparticle(s) surrounded by the polymer which forms the microspheres, (3) a polymer core within a protein microsphere, (4) a polymer coating around a polymer microsphere, (5) mixed in with microspheres aggregated into a larger form, or (6) a combination thereof. Bioactive agents can be incorporated as particulates or by co-dissolving the factors with the polymer. Stabilizers can be incorporated by addition of the stabilizers to the factor solution prior to formation of the microspheres.

The bioactive agent can be incorporated into a hydrogel and coated or otherwise deposited in or on the membrane system. Some hydrogels suitable for use in the preferred embodiments include cross-linked, hydrophilic, three-dimensional polymer networks that are highly permeable to the bioactive agent and are triggered to release the bioactive agent based on a stimulus.

The bioactive agent can be incorporated into the membrane system by solvent casting, wherein a solution including dissolved bioactive agent is disposed on the surface of the membrane system, after which the solvent is removed to form a coating on the membrane surface.

The bioactive agent can be compounded into a plug of material, which is placed within the device, such as is described in U.S. Pat. No. 4,506,680 and U.S. Pat. No. 5,282,844. In some embodiments, it is preferred to dispose the plug beneath a membrane system; in this way, the bioactive agent is controlled by diffusion through the membrane, which provides a mechanism for sustained-release of the bioactive agent in the host.

Release of Bioactive Agents

Numerous variables can affect the pharmacokinetics of bioactive agent release. The bioactive agents of the preferred embodiments can be optimized for short- or long-term release. In some embodiments, the bioactive agents of the preferred embodiments are designed to aid or overcome factors associated with short-term effects (e.g., acute inflammation or thrombosis) of sensor insertion. In some embodiments, the bioactive agents of the preferred embodiments are designed to aid or overcome factors associated with long-term effects, for example, chronic inflammation or build-up of fibrotic tissue or plaque material. In some embodiments, the bioactive agents of the preferred embodiments combine short- and long-term release to exploit the benefits of both.

As used herein, 'controlled,' 'sustained or 'extended' release of the factors can be continuous or discontinuous, linear or non-linear. This can be accomplished using one or more types of polymer compositions, drug loadings, selections of excipients or degradation enhancers, or other modifications, administered alone, in combination or sequentially to produce the desired effect.

Short-term release of the bioactive agent in the preferred embodiments generally refers to release over a period of from about a few minutes or hours to about 2, 3, 4, 5, 6, or 7 days or more.

Loading of Bioactive Agents

The amount of loading of the bioactive agent into the membrane system can depend upon several factors. For example, the bioactive agent dosage and duration can vary with the intended use of the membrane system, for example, the intended length of use of the device and the like; differences among patients in the effective dose of bioactive agent; location and methods of loading the bioactive agent; and release rates associated with bioactive agents and optionally their carrier matrix. Therefore, one skilled in the art will appreciate the variability in the levels of loading the bioactive agent, for the reasons described above.

In some embodiments, in which the bioactive agent is incorporated into the membrane system without a carrier matrix, the preferred level of loading of the bioactive agent into the membrane system can vary depending upon the nature of the bioactive agent. The level of loading of the bioactive agent is preferably sufficiently high such that a biological effect (e.g., thrombosis prevention) is observed. Above this threshold, the bioactive agent can be loaded into the membrane system so as to imbibe up to 100% of the solid portions, cover all accessible surfaces of the membrane, or fill up to 100% of the accessible cavity space. Typically, the level of loading (based on the weight of bioactive agent(s), membrane system, and other substances present) is from about 1 ppm or less to about 1000 ppm or more, preferably from about 2, 3, 4, or 5 ppm up to about 10, 25, 50, 75, 100, 200, 300, 400, 500, 600, 700, 800, or 900 ppm. In certain embodiments, the level of loading can be 1 wt. % or less up to about 50 wt. % or more, preferably from about 2, 3, 4, 5, 6, 7, 8, 9, 10, 15, or 20 wt. % up to about 25, 30, 35, 40, or 45 wt. %.

When the bioactive agent is incorporated into the membrane system with a carrier matrix, such as a gel, the gel concentration can be optimized, for example, loaded with one or more test loadings of the bioactive agent. It is generally preferred that the gel contain from about 0.1 or less to about 50 wt. % or more of the bioactive agent(s), preferably from about 0.2, 0.3, 0.4, 0.5, 0.6, 0.7, 0.8, or 0.9 wt. % to about 6, 7, 8, 9, 10, 15, 20, 25, 30, 35, 40, or 45 wt. % or more bioactive agent(s), more preferably from about 1, 2, or 3 wt. % to about 4 or 5 wt. % of the bioactive agent(s). Substances that are not bioactive can also be incorporated into the matrix.

Referring now to microencapsulated bioactive agents, the release of the agents from these polymeric systems generally occurs by two different mechanisms. The bioactive agent can be released by diffusion through aqueous filled channels generated in the dosage form by the dissolution of the agent or by voids created by the removal of the polymer solvent or a pore forming agent during the original micro-encapsulation. Alternatively, release can be enhanced due to the degradation of the encapsulating polymer. With time, the polymer erodes and generates increased porosity and microstructure within the device. This creates additional pathways for release of the bioactive agent.

In some embodiments, the sensor is designed to be bioinert, e.g., by the use of bioinert materials. Bioinert materials do not substantially cause any response from the host. As a result, cells can live adjacent to the material but do not form a bond with it. Bioinert materials include but are not limited to alumina, zirconia, titanium oxide or other bioinert materials generally used in the 'catheter/catheterization' art. While not wishing to be bound by theory, it is believed that inclusion of a bioinert material in or on the sensor can reduce attachment of blood cells or proteins to the sensor, thrombosis or other host reactions to the sensor.

EXAMPLES

Example 1

Sensors were built to test the ability of a silicone end group-containing polyurethane to reduce or block non-constant noise on a glucose sensor signal. Transcutaneous sensors, with electrode, enzyme and bioprotective domains, were built and tested. The control and test sensors were built as described in the section entitled 'Exemplary Glucose Sensor Configuration,' including an electrode domain, an enzyme domain and an integral bioprotective domain with one difference: the test sensors were built with a bioprotective domain comprising a silicone-polycarbonate-urethane including about 19% silicone by weight, and further including PVP added thereto (about 25% by weight to provide glucose permeability to the membrane); and the control sensors were built with a bioprotective domain comprising a polyurethane membrane with both hydrophilic and hydrophobic regions to control the diffusion of glucose and oxygen to the glucose sensor. Namely, the bioprotective domain of the test sensors included a polyurethane with silicone end groups (~19% by weight silicone) as compared to the control sensors, which did not include silicone in the bioprotective domain.

Six of the control sensors and six of the test sensors were placed in a solution containing 200 mg/dL glucose, and then subsequently placed in a solution containing 200 mg/dL of glucose and a therapeutic does of acetaminophen (165 µM). When the control sensors were moved to the glucose and acetaminophen containing solution, the signal increased on average by 622%. When the test sensors were moved to the glucose and acetaminophen containing solution, the signal increased on average by 4%. Accordingly, a glucose sensor having a bioprotective domain comprising a silicone end group-containing polyurethane, including about 19% silicone by weight, blended with PVP may substantially block or attenuate the effect or influence of a known interferent, acetaminophen, as compared to a control sensor.

Example 2

Figure 5:
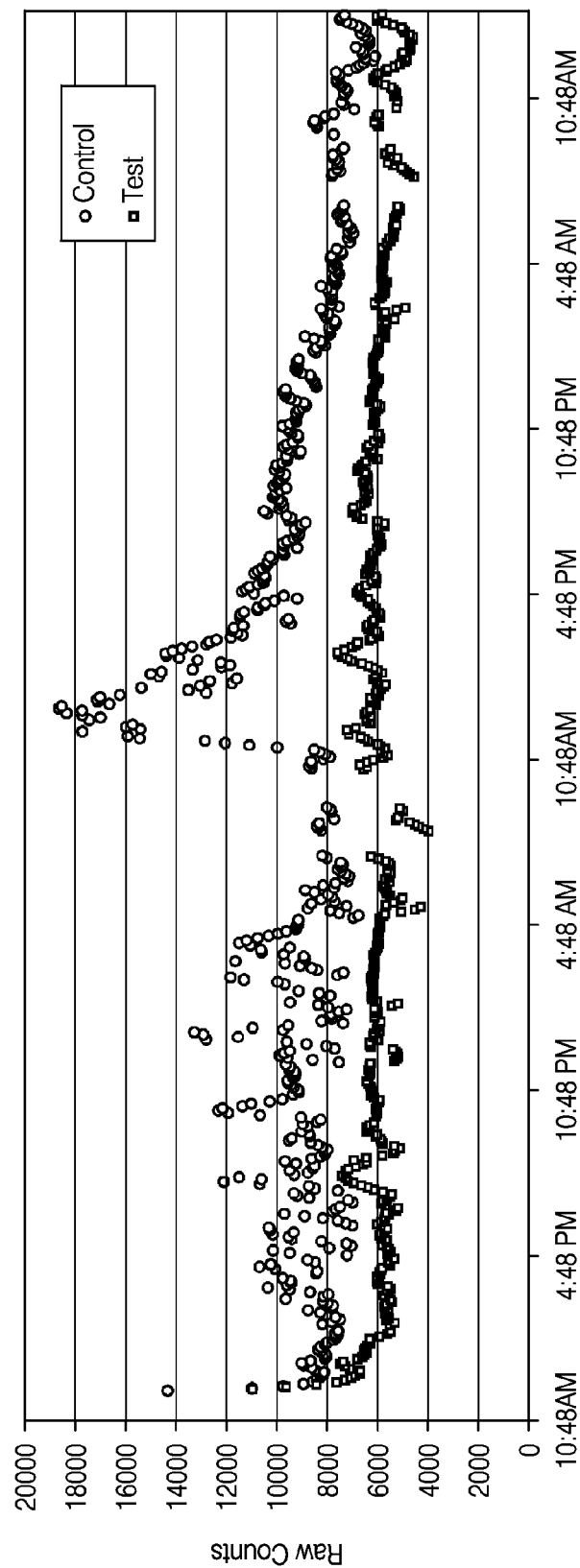
FIG. 5 is a graph illustrating in vivo test results comparing a control and test sensors bilaterally implanted in a human host, as described in Example 2.

Test and Control sensors as described with reference to Example 1, above, were implanted bilaterally in humans and the signal evaluated. FIG. 5 is a graph illustrating the continuous glucose sensor data from the bilaterally implanted sensors in one human host over about two days. The x-axis represents time; the y-axis represents signal amplitude in counts. Circles represent the data set obtained from a control sensor with the configuration of Example 1 implanted on a first side of the host. The squares represent the data set obtained from a test sensor with the configuration of Example 1 implanted on the other side of the same host. It can be seen that the control sensor exemplified a much higher level of (non-constant) noise than the test sensor, as evidenced by the sporadic rises and falls seen in the control sensor data during the first 24 hours, for example. These rises and falls are non-physiological in nature, as evidenced by their rate of change being above known physiological limits of glucose concentration in humans. After about 24 hours, the host ingested a therapeutic dose of acetaminophen. The spike (indicated by the arrow) in the control sensor data correlates with the acetaminophen ingestion while the time-corresponding test sensor data (associated with the timing of the acetaminophen ingestion) does not show a substantial change in the signal. Accordingly, a bioprotective domain comprising a silicone end group-containing polyurethane, including about 19% silicone by weight, substantially blocks or attenuates the affect and/or influence of a known chemical and biological non-constant noise-causing species.

Example 3

Figure 6A:
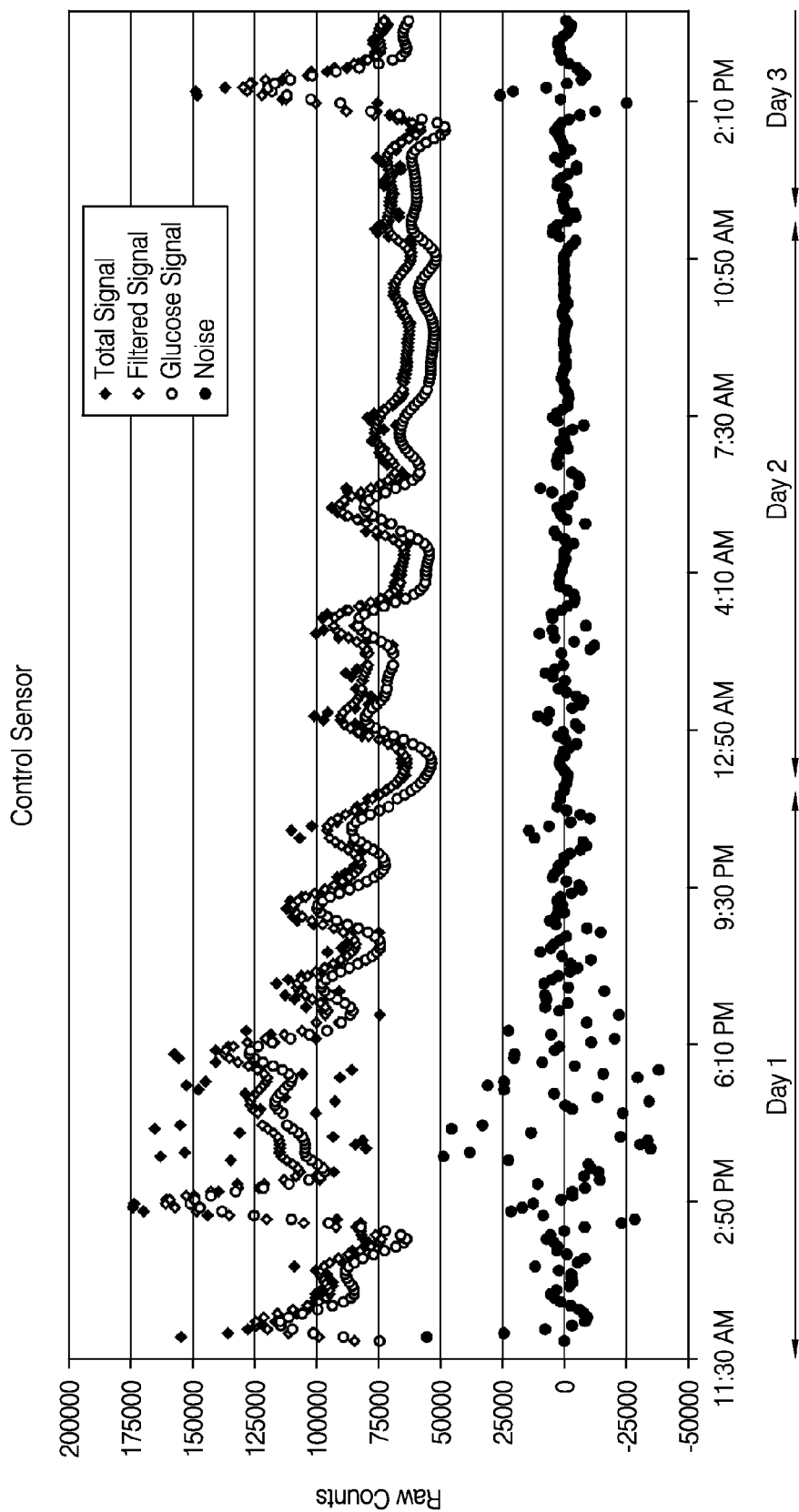
FIGS. 6A and 6B are graphs illustrating in vivo test results from control (FIG. 6A) and test (FIG. 6B) sensors implanted bilaterally into a rat, over a period of more than about 2 days.
Figure 6B:
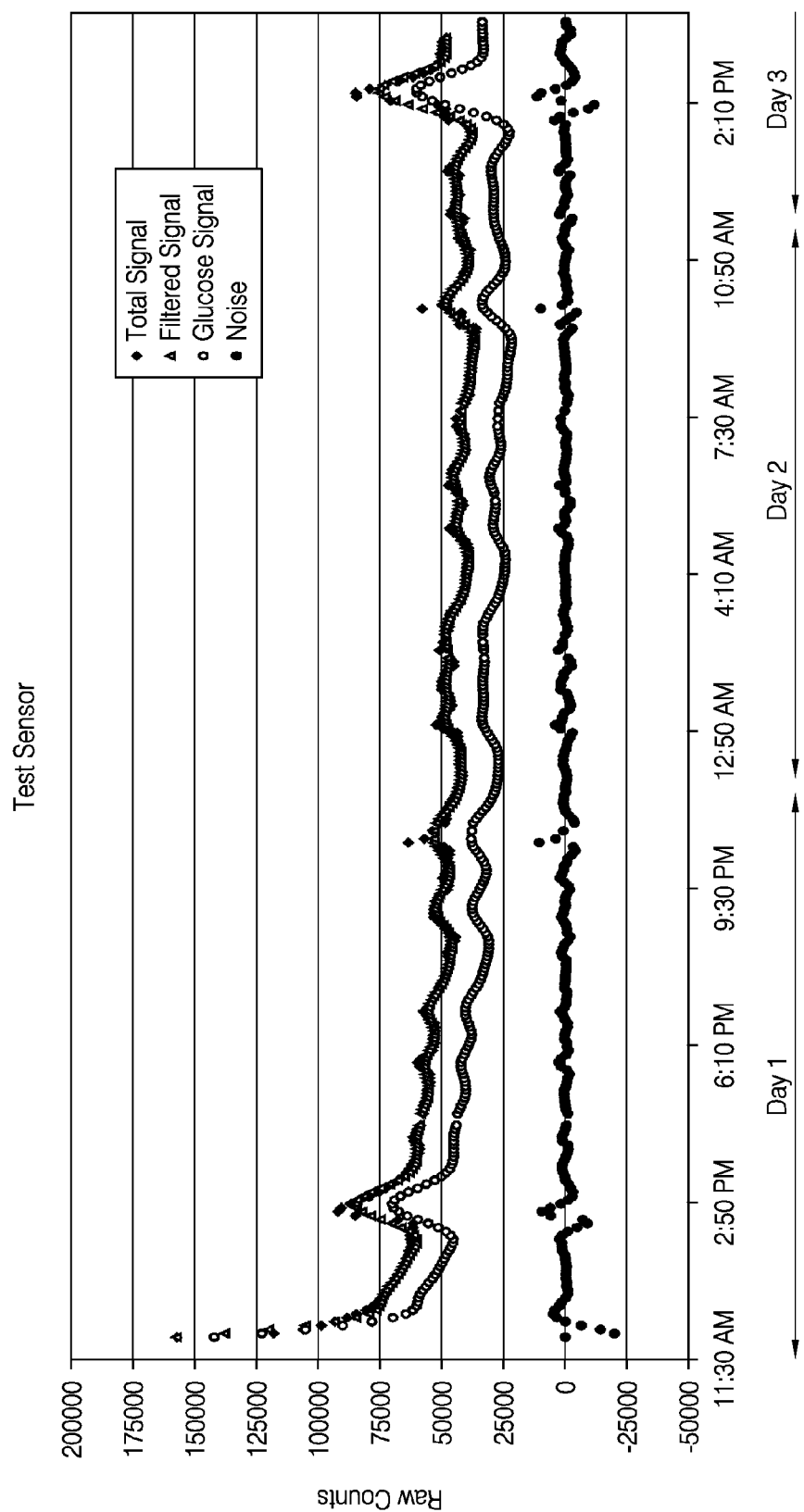

Test and Control sensors as described with reference to Example 1, above, were implanted bilaterally in diabetic rats for more than about 2 days. FIGS. 6A and 6B illustrate exemplary test results from a control sensor (FIG. 6A) and test sensor (FIG. 6B) implanted bilaterally in one rat, over a period more than about 2 days, after sensor break-in. The Y-axis represents signal amplitude (in counts). The X-axis represents time. Double-headed arrows approximately indicate the days of the study. The total signal detected by the test glucose sensor is shown as filled diamonds. To determine the signal components, the total signal, for each of the test and control data sets, was analyzed in the following manner. First, the total signal was filtered using an IIR filter to obtain the filtered signal (open diamonds). The non-constant noise component (filled circles) was obtained by subtracting the filtered signal from the total signal. Next, the filtered signal was calibrated using glucose values obtained from a finger-stick glucose meter (SMBG), as described as described in more detail elsewhere herein, to obtain the constant noise signal component (e.g., from the baseline of the calibration equation, not shown). Finally, the glucose component (open circles) of the total signal was obtained by subtracting the constant noise signal component from the filtered signal.

A severe noise episode can be seen on Day 1 (from about 15:30 to about 18:50) on the control sensor data set (FIG. 6A). During the noise episode the non-constant noise component of the signal from the control sensor was about 21.8% of the total signal as compared to the non-constant noise component of the signal from the test sensor was only about 2.4% of the total signal. Using the Root Mean Square (RMS) method with a window of about 3 hours and 15 minutes, it was determined that the non-constant noise signal component was no more than about 12% of the total signal for the test sensor (including the bioprotective domain of the preferred embodiments) at any time during the sensor session. Accordingly, it was shown that a sensor including a bioprotective domain of the preferred embodiments (including a silicone end group-containing polyurethane) can reduce the non-constant noise-component of the total signal by about 18% during a severe noise episode. Furthermore, it was shown that for a glucose sensor including a bioprotective domain of the preferred embodiments, the non-constant noise component of the signal is less than about 12% of the total signal over a period of more than about a 2-day sensor session.

Example 4

Figure 7:
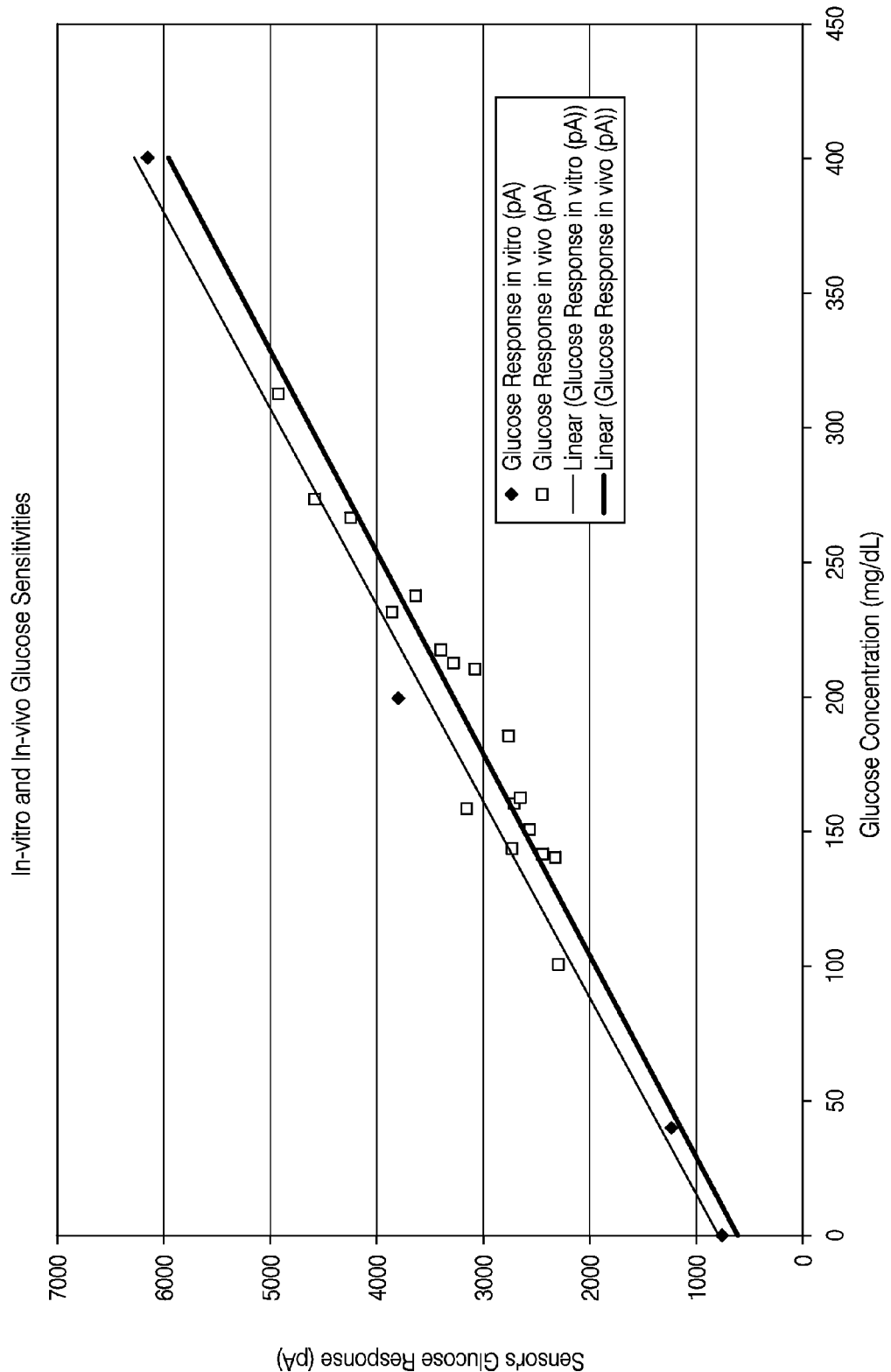
FIG. 7 is a graph comparing the in vivo glucose sensitivity of a sensor implanted in one rat with the in vitro glucose sensitivity of a sensor in glucose PBS solution, as described in Example 4.

An analysis was conducted on test sensors, which were built in substantially the same way as the test sensors described in Example 1, to determine whether a strong positive correlation exists between in vivo and in vitro sensor glucose measurements (e.g., sensitivity of glucose concentration readings). The test sensors were built with electrode, enzyme, and bioprotective domains. The bioprotective domain included a silicone-polycarbonate-urethane having about 20% silicone by weight, and further included PVP added thereto (about 17.5% by weight to provide glucose permeability to the membrane). A number of the test sensors were placed in glucose PBS (phosphate buffered saline) solution for calibration use, while a corresponding number of test sensors were then implanted in vivo into diabetic rats for more than about seven days to monitor their glucose levels. FIG. 7 illustrates a graph comparing the initial in vivo glucose sensitivity of a test sensor implanted in one rat with the in vitro glucose sensitivity of a test sensor in glucose PBS solution. As shown in FIG. 7, a linear regression was then performed to calculate the sensitivities of the test sensors in an in vivo environment and in an in vitro environment. The sensitivities of the in vivo and the in vitro test sensors were found to be about 13.37 and 13.73 pA/mg/dL, respectively. Accordingly, it can be determined that the ratio between in vivo and in vitro glucose sensitivities in this particular study was at least greater than 0.97 to 1, and about 1 to 1, with a standard deviation of about 0.1. The test data also showed that the correlation, i.e., $R^2$, between in vivo and in vitro glucose sensitivities of a fixed population of test sensors manufactured in substantially the same way to be about 0.98.

In similar studies, while the in vivo to in vitro sensitivity ratio was not found to be 1 to 1, the in vivo to in vitro sensitivity ratio was nonetheless found to be substantially fixed. In other words, in these studies, the ratio was found to be substantially consistent across a fixed population of test sensors manufactured in substantially the same way. In these studies, the ratios between in vivo and in vitro glucose sensitivities have been found in certain circumstances to be from about 1 to 1.5 to about 1 to 10, in other circumstances from about 1 to 0.1 and about 1 to 0.7. In these studies, the correlation between in vivo and in vitro glucose sensitivities was also found to be high, i.e., in certain circumstances greater than or about 0.7, in other circumstances greater than or about 0.8, in still other circumstances greater than or about 0.9, in certain circumstances, greater than or about 0.95, and in still other circumstances greater than or about 0.98.

Example 5

Dual-electrode sensors were built to test the ability of a silicone end group-containing polyurethane blended with PVP to reduce or block non-constant noise on a glucose sensor signal. The dual-electrode sensors were each built to include an electrode layer, an enzyme layer and a bioprotective layer. (As described below, in some instances, some or all of the enzyme layer did not include enzyme). More specifically, the dual-electrode sensors were constructed from two platinum wires, each coated with a layer of polyurethane to form the electrode layer. Exposed electroactive windows were cut into the wires by removing a portion thereof. The sensors were trimmed to a length. A solution with the glucose oxidase enzyme was then applied to one electrode (i.e., the enzymatic electrode) to form an enzyme layer, while the same solution, but without glucose oxidase, was then applied to the other electrode (i.e., the non-enzymatic electrode) to form a non-enzyme layer. After the sensors were dried, a bioprotective layer was deposited onto each sensor and then dried. Depending on whether a particular sensor was assigned as a control sensor or as a test sensor, the material deposited onto the sensor to form the bioprotective layer was different. With control sensors, the bioprotective layer was formed of a conventional polyurethane membrane. In contrast, with test sensors, the bioprotective layer was formed of a blend of silicone-polycarbonate-urethane (approximately 84% by weight) and polyvinylpyrrolidone (16% by weight). The platinum wires were then laid next to each other such that the windows are offset (e.g., separated by a diffusion barrier). The bundle was then placed into a winding machine and silver wire was wrapped around the platinum electrodes. The silver wire was then chloridized to produce a silver/silver chloride reference electrode.

FIG. 8 illustrates the results from one in vivo experiment comparing the signals received from the enzymatic electrodes of the test and control sensors. During testing, the test and control sensors were incorporated into catheters connected to human patients and to an intravenous blood glucose monitoring system, and a 1,000 mg dose of acetaminophen was administered orally to the patients. As illustrated in FIG. 8, the patients linked to the control and test sensors were each administered with the acetaminophen dose at approximately 11:48 AM. As also illustrated, after the patient linked to the test sensor was administered acetaminophen, the signals received from the enzymatic electrode ascended from readings of about 105-115 mg/dL to readings of about 185-195 mg/dL. From this, it can be estimated that for the control sensor in this particular experiment, the equivalent peak glucose response of the enzymatic electrode to a 1,000 mg dose of acetaminophen administered to the patient is at least about 80 mg/dL. To compare, as also illustrated in FIG. 8, after the other patient linked with the control sensor was administered acetaminophen, the baseline signals received from the enzymatic electrode quickly increased from readings of about 70-80 mg/dL to readings of about 390-400 mg/dL. From this, it can be estimated that for test sensor in this particular experiment, the equivalent peak glucose response of the enzymatic electrode to a 1,000 mg dose of acetaminophen administered to the patient is at least about 320 mg/dL. Collectively, these results appear to indicate that the use of a polymer comprising a blend of a silicone-polycarbonate-urethane base polymer with polyvinylpyrrolidone can provide a mechanism for reducing the flux of interferents (e.g., acetaminophen) through the membrane.

Example 6

An in vivo analysis was conducted to compare the glucose-signal-to-baseline-signal ratios of the control and test sensors described in Example 5. As previously described, the dual-electrode sensors in this experiment each comprise one electrode configured to be enzymatic and a corresponding electrode configured to be non-enzymatic. The enzymatic electrode is configured to measure a total signal comprising glucose and baseline signals, and the non-enzymatic electrode is configured to measure a baseline signal consisting of the baseline signal only. In this way, the baseline signal can be determined and subtracted from the total signal to generate a difference signal, i.e., a glucose-only signal that is substantially not subject to fluctuations in the baseline or interfering species on the signal.

Figure 9A:
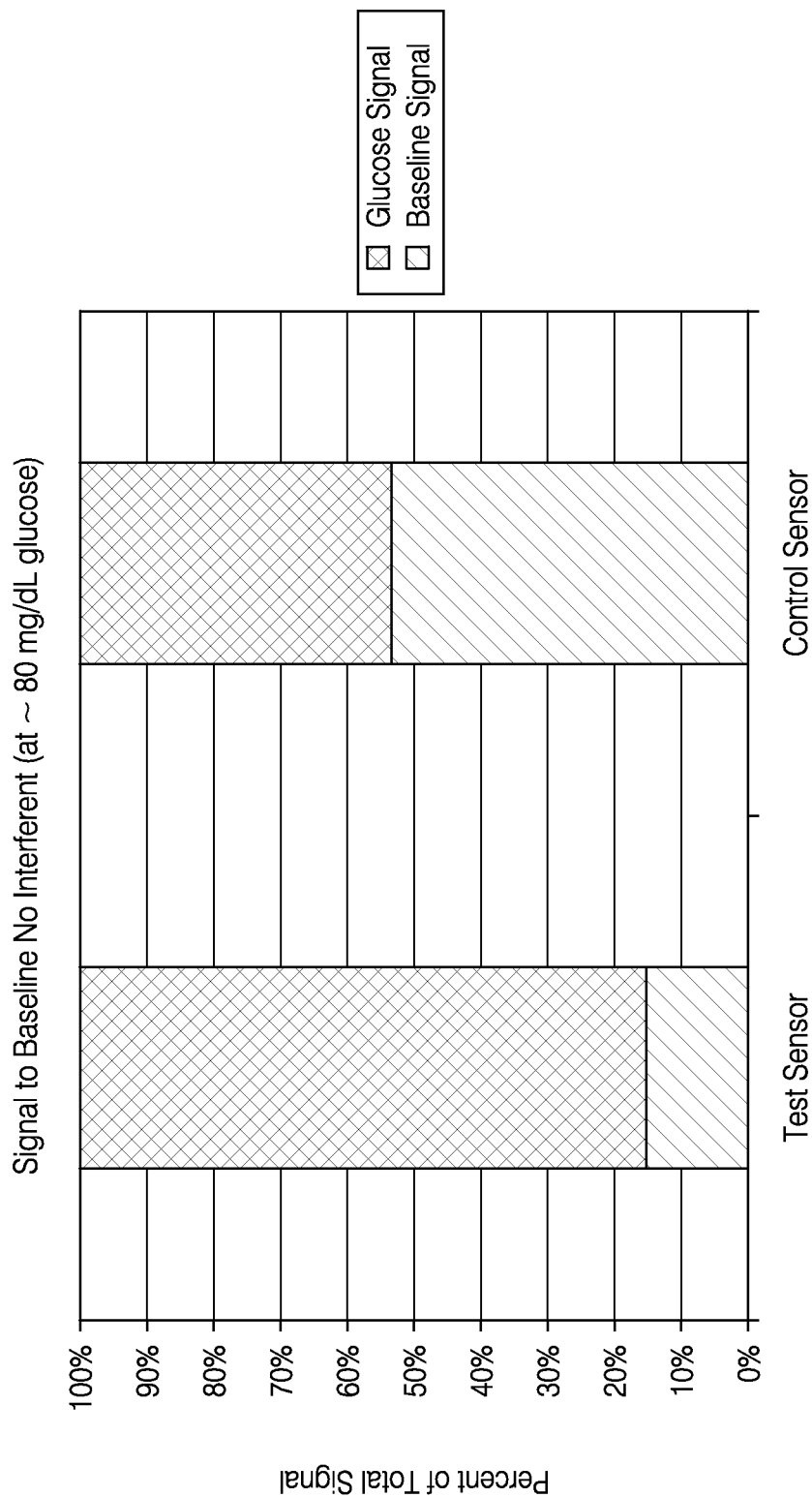
FIGS. 9A and 9B are graphs illustrating the percentages of baseline signal to total signal under various environments, as described in Example 6.
Figure 9B:
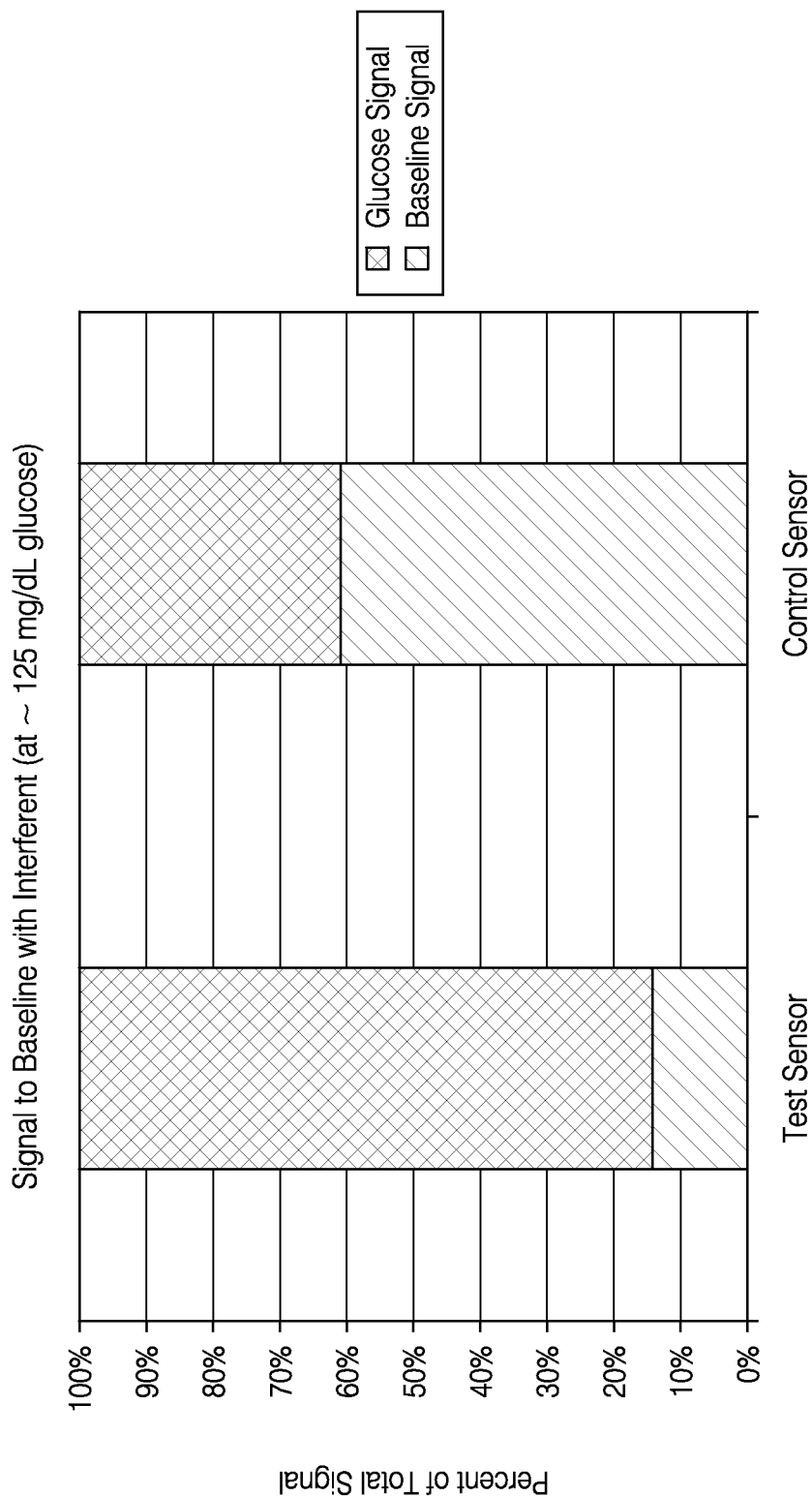

To provide a basis for comparing the two sensors, data were taken at the same glucose concentration for both sensors. In this particular experiment, sensor data in the normal glucose range, i.e., approximately 80-125 mg/dL were selected. In a first experiment, for both the control and test sensors, the glucose-signal-to-baseline-signal ratios were calculated and compared in an environment where the glucose concentration is approximately 80 mg/dL and where acetaminophen was not detectably present, as illustrated in FIG. 9A. In a second experiment, for both the control and test sensors, the glucose-signal-to-baseline-signal ratios were calculated and compared in an environment where the glucose concentration is approximately 125 mg/dL and where acetaminophen was present at a concentration of approximately 1-3 mg/dL, as illustrated in FIG. 9B. As shown in FIGS. 9A and 9B, under both above-described environments, the test sensor had considerably higher glucose-signal-to-baseline-signal ratios than the control sensor. For instance, as shown in FIG. 9A, under an environment where glucose concentration was approximately 80 mg/dL and where there was no acetaminophen detectably present, the baseline signal of the test sensor was found to be approximately 15% of the total signal (corresponding to a glucose-signal-to-baseline-signal ratio of approximately 5.7 to 1), whereas the baseline signal of the control sensor was found to be approximately 53% of the total signal (corresponding to a glucose-signal-to-baseline-signal ratio of approximately 0.9 to 1). As also shown in FIG. 9B, under an environment where glucose concentration was approximately 125 mg/dL and where acetaminophen was present at a concentration of approximately 1-3 mg/dL, the baseline signal of the test sensor was found to be approximately 15% of the total signal (corresponding to a glucose-signal-to-baseline-signal ratio of approximately 5.7 to 1), whereas the baseline signal of the control sensor was found to be approximately 61% of the total signal (corresponding to a glucose-signal-to-baseline-signal ratio of approximately 0.64 to 1). In other similar experiments, a glucose-signal-to-baseline-signal ratio of approximately 2 to 1, 3 to 1, 4 to 1, 5 to 1, 6 to 1, 7 to 1, 8 to 1, 9 to 1, and 10 to 1 have been obtained.

Example 7

In vitro tests were also conducted to evaluate the ability of the test sensors described in Examples 5 and 6 to reduce the interference effects of various interferents, specifically, acetaminophen, albuterol, ascorbic acid, atenolol, haloperidol, lidocaine, mataproterenol, metoprolol, phenylephrine, propofol, and uric acid. During testing, each test sensor underwent a calibration check, after which, it was immersed in a solution comprising a test concentration of the interferent. The resulting signal from the enzymatic electrode of each test sensor was then monitored. Based on known sensitivities of each test sensor, an estimated equivalent glucose signal was then calculated. The estimated equivalent glucose signals from the tests performed on the different interferents are summarized in Table 1 below.

TABLE 1

| Interferent | Test Concentration (mg/dL) | Equivalent Glucose Signal (mg/dL) |
|---|---|---|
| Acetaminophen | ~3 | ~30 |
| Albuterol | ~0.04 | ~~3 |
| Ascorbic Acid | ~6 | ~17 |
| Atenolol | ~1 | ~1 |
| Haloperidol | ~0.1 | ~~5 |
| Lidocaine | ~1.2 | ~~3 |
| Metaproterenol | ~0.001 | ~1 |
| Metoprolol | ~0.5 | ~~1 |
| Phenylephrine | ~4 | ~10 |
| Propofol | ~0.65 | ~0 |
| Uric Acid | ~6 | ~25 |

Example 8

Five transcutaneous glucose sensors were built to evaluate the level of accuracy (with respect to glucose concentration measurements) that can be attained from using a silicone-containing polyurethane blended with PVP, with the bioprotective domain of each sensor having a different percentage of PVP. The five sensors were then implanted into five different human hosts.

Table 2 below summarizes the levels of accuracy, in terms of mean absolute relative difference (MARD), attained by four of the five above-described sensors. MARD was calculated by measuring the average relative difference between each of the above-described sensors and their corresponding reference measurements, on a percentage basis. The reference measurements associated with calculation of the mean absolute relative difference were determined by analysis of blood.

TABLE 2

| Sensor No. | Overall MARD (40 mg/dL-400 mg/dL, Days 1-7) | Low Glucose MARD (40 mg/dL-80 mg/dL) | Low Glucose MAD (40 mg/dL-80 mg/dL) (in units of mg/dL) |
|---|---|---|---|
| Sensor 1 | 6.8% | 13.7% | 7 |
| Sensor 2 | 16.1% | 4.9% | 3 |
| Sensor 3 | 9.6% | 9.6% | 6.5 |
| Sensor 4 | 9.6% | 6% | 4.3 |

As illustrated above, with Sensor 1, the MARD calculated for measurements of glucose concentrations from about 40 mg/dL to about 400 mg/dL was measured to be about 6.8% and that from about 40 mg/dL to about 80 mg/dL was measured to be about 13.7%. The mean absolute difference (MAD) for Sensor 1 was about 7 mg/dL. With Sensor 2, the MARD calculated for measurements of glucose concentrations from about 40 mg/dL to about 400 mg/dL was about 16.1% and that from about 40 mg/dL to about 80 mg/dL was measured to be about 4.9%. The MAD for Sensor 2 was about 3 mg/dL. With Sensor 3, the MARD calculated for measurements of glucose concentrations from about 40 mg/dL to about 80 mg/dL and that from about 40 mg/dL to about 80 mg/dL were about the same, i.e., at about 9.6%. The MAD for Sensor 3 was about 4.3 mg/dL. With Sensor 4, the MARD (6%) calculated for measurements of glucose concentrations from about 40 mg/dL to about 80 mg/dL and was lower than that (9.6%) from about 40 mg/dL to about 400 mg/dL. The MAD for Sensor 4 was about 4.3 mg/dL. As can be seen from the table, by employing the above-described method for fabricating a bioprotective domain, it was possible to achieve a sensor capable of providing a low glucose concentration accuracy associated with MARD that was substantially the same. A fifth sensor (not listed in Table 2), which was configured to have a sensor session of at least about 10 days and configured to enhance accuracy at the end of the sensor session was found to have a 10th day-accuracy level corresponding to a MARD of about 6.5%.

Methods and devices that are suitable for use in conjunction with aspects of the preferred embodiments are disclosed in U.S. Pat. No. 4,757,022; U.S. Pat. No. 6,702,857; U.S. Pat. No. 7,632,228; U.S. Pat. No. 7,471,972; U.S. Pat. No. 6,001,067; U.S. Pat. No. 7,226,978; U.S. Pat. No. 7,134,999; U.S. Pat. No. 7,192,450; U.S. Pat. No. 7,599,726; U.S. Pat. No. 7,583,990; U.S. Pat. No. 7,379,765; U.S. Pat. No. 7,108,778; U.S. Pat. No. 7,074,307; U.S. Pat. No. 6,931,327; U.S. Pat. No. 7,276,029; U.S. Pat. No. 7,081,195; U.S. Pat. No. 7,519,408; U.S. Pat. No. 7,364,592; U.S. Pat. No. 7,591,801; U.S. Pat. No. 7,460,898; U.S. Pat. No. 7,467,003; U.S. Pat. No. 7,366,556; U.S. Pat. No. 7,424,318; U.S. Pat. No. 7,637,868; U.S. Pat. No. 7,657,297; U.S. Pat. No. 7,497,827; U.S. Pat. No. 7,310,544; U.S. Pat. No. 7,654,956; U.S. Pat. No. 7,651,596; U.S. Pat. No. 7,494,465; U.S. Pat. No. 7,640,048; U.S. Pat. No. 7,613,491; U.S. Pat. No. 7,615,007; U.S. Pat. No. 6,741,877; U.S. Pat. No. 7,110,803; U.S. Pat. No. 6,558,321; U.S. Pat. No. 6,862,465; U.S. Pat. No. 7,136,689; and U.S. Pat. No. 4,994,167.

Methods and devices that are suitable for use in conjunction with aspects of the preferred embodiments are disclosed in U.S. Patent Publication No. US-2009-0045055-A1; U.S. Patent Publication No. US-2005-0177036-A1; U.S. Patent Publication No. US-2006-0258761-A1; U.S. Patent Publication No. US-2006-0086624-A1; U.S. Patent Publication No. US-2006-0200022-A1; U.S. Patent Publication No. US-2006-0224108-A1; U.S. Patent Publication No. US-2006-0211921-A1; U.S. Patent Publication No. US-2005-0031689-A1; U.S. Patent Publication No. US-2006-0198864-A1; U.S. Patent Publication No. US-2006-0204536-A1; U.S. No. US-2005-0027463-A1; U.S. Patent Publication No. US-2009-0192745-A1; U.S. Patent Publication No. US-2009-0143659-A1; U.S. Patent Publication No. US-2008-0194936-A1; U.S. Patent Publication No. US-2006-0200019-A1; U.S. Patent Publication No. US-2007-0197890-A1; U.S. Patent Publication No. US-2006-0189856-A1; U.S. Patent Publication No. US-2005-0187720-A1; U.S. Patent Publication No. US-2008-0183061-A1; U.S. Patent Publication No. US-2008-0183399-A1; U.S. Patent Publication No. US-2008-0189051-A1; U.S. Patent Publication No. US-2008-0021666-A1; U.S. Patent Publication No. US-2008-0306368-A1; U.S. Patent Publication No. US-2009-0012379-A1; U.S. Patent Publication No. US-2005-0027180-A1; U.S. Publication No. US-2005-0043598-A1; U.S. Patent Publication No. US-2010-0036222-A1; U.S. Patent Publication No. US-2010-0036223-A1; U.S. Patent Publication No. US-2010-0036215-A1; U.S. Patent Publication No. US-2010-0030053-A1; U.S. Patent Publication No. US-2010-0036225-A1; U.S. Patent Publication No. US-2010-0036216-A1; U.S. Patent Publication No. US-2010-0036224-A1; U.S. Patent Publication No. US-2007-0032706-A1; U.S. Patent Publication No. US-2009-0124877-A1; U.S. Patent Publication No. US-2009-0124878-A1; U.S. Patent Publication No. US-2008-0045824-A1; U.S. Patent Publication No. US-2005-0203360-A1; U.S. Patent Publication No. US-2009-0062635-A1; U.S. Patent Publication No. US-2009-0043181-A1; U.S. Patent Publication No. US-2010-

0010324-A1; U.S. Patent Publication No. US-2010-0030484-A1; U.S. Patent Publication No. US-2010-0022855-A1; U.S. Patent Publication No. US-2010-0016687-A1; U.S. Patent Publication No. US-2010-0010331-A1; U.S. Patent Publication No. US-2010-0010332-A1; U.S. Patent Publication No. US-2010-0030038-A1; U.S. Patent Publication No. US-2010-0030485-A1; U.S. Patent Publication No. US-2009-0043541-A1; U.S. Patent Publication No. US-2009-0043542-A1; U.S. Patent Publication No. US-2009-0043525-A1; U.S. Patent Publication No. US-2009-0036758-A1; U.S. Patent Publication No. US-2009-0043182-A1; U.S. Patent Publication No. US-2009-0204341-A1; U.S. Patent Publication No. US-2009-0203981-A1; U.S. Patent Publication No. US-2009-0299162-A1; U.S. Patent Publication No. US-2005-0176136-A1; U.S. Patent Publication No. US-2008-0287765-A1; U.S. Patent Publication No. US-2010-0016698-A1; U.S. Patent Publication No. US-2008-0287764-A1; U.S. Patent Publication No. US-2008-0287766-A1; U.S. Patent Publication No. US-2008-0262469-A1; U.S. Patent Publication No. US-2009-0299276-A1; U.S. Patent Publication No. US-2005-0143635-A1; U.S. Patent Publication No. US-2009-0099436-A1; U.S. Patent Publication No. US-2008-0214918-A1; U.S. Patent Publication No. US-2009-0182217-A1; U.S. Patent Publication No. US-2009-0062633-A1; U.S. Patent Publication No. US-2005-0242479-A1; U.S. Patent Publication No. US-2009-0030294-A1; U.S. Patent Publication No. US-2006-0015024-A1; U.S. Patent Publication No. US-2008-0194938-A1; U.S. Patent Publication No. US-2006-0036142-A1; U.S. Patent Publication No. US-2006-0020188-A1; U.S. Patent Publication No. US-2006-0036141-A1; U.S. Patent Publication No. US-2006-0020190-A1; U.S. Patent Publication No. US-2009-0076361-A1; U.S. Patent Publication No. US-2006-0036143-A1; U.S. Patent Publication No. US-2006-0036140-A1; U.S. Patent Publication No. US-2006-0019327-A1; U.S. Patent Publication No. US-2006-0020186-A1; U.S. Patent Publication No. US-2008-0214915-A1; U.S. Patent Publication No. US-2008-0194935-A1; U.S. Patent Publication No. US-2008-0071156-A1; U.S. Patent Publication No. US-2008-0275313-A1; U.S. Patent Publication No. US-2006-0020191-A1; U.S. Patent Publication No. US-2008-0188731-A1; U.S. Patent Publication No. US-2009-0156919-A1; U.S. Patent Publication No. US-2009-0143660-A1; U.S. Patent Publication No. US-2009-0163790-A1; U.S. Patent Publication No. US-2006-0142651-A1; U.S. Patent Publication No. US-2007-0059196-A1; U.S. Patent Publication No. US-2006-0155180-A1; U.S. Patent Publication No. US-2006-0270923-A1; U.S. Patent Publication No. US-2009-0036763-A1; U.S. Patent Publication No. US-2006-0258929-A1; U.S. Patent Publication No. US-2006-0257996-A1; U.S. Patent Publication No. US-2007-0173709-A1; U.S. Patent Publication No. US-2006-0253012-A1; U.S. Patent Publication No. US-2006-0036144-A1; U.S. Patent Publication No. US-2009-0216103-A1; U.S. Patent Publication No. US-2008-0242961-A1; U.S. Patent Publication No. US-2009-0124879-A1; U.S. Patent Publication No. US-2006-0222566-A1; U.S. Patent Publication No. US-2006-0192724-A1; U.S. Patent Publication No. US-2006-0183985-A1; U.S. Patent Publication No. US-2009-0163791-A1; U.S. Patent Publication No. US-2006-0195029-A1; U.S. Patent Publication No. US-2008-0296155-A1; U.S. Patent Publication No. US-2008-0208025-A1; U.S. Patent Publication No. US-2009-0287073-A1; U.S. Patent Publication No. US-2007-0197889-A1; U.S. Patent Publication No. US-2008-0119703-A1; U.S. Patent Publication No. US-2008-0119704-A1; U.S. Patent Publication No. US-2008-0119706-A1; U.S. Patent Publication No. US-2008-0086042-A1; U.S. Patent Publication No. US-2008-0086044-A1; U.S. Patent Publication No. US-2009-0287074-A1; U.S. Patent Publication No. US-2007-0235331-A1; U.S. Patent Publication No. US-2008-0306434-A1; U.S. Patent Publication No. US-2008-0306444-A1; U.S. Patent Publication No. US-2008-0306435-A1; U.S. Patent Publication No. US-2009-0076360-A1; U.S. Patent Publication No. US-2009-0192751-A1; U.S. Patent Publication No. US-2009-0192366-A1; U.S. Patent Publication No. US-2009-0192722-A1; U.S. Patent Publication No. US-2009-0156924-A1; U.S. Patent Publication No. US-2009-0299155-A1; U.S. Patent Publication No. US-2009-0299156-A1; U.S. Patent Publication No. US-2009-0240120-A1; U.S. Patent Publication No. US-2009-0240193-A1; U.S. Patent Publication No. US-2009-0240128-A1; U.S. Patent Publication No. US-2009-0247856-A1; U.S. Patent Publication No. US-2009-0247855-A1; U.S. Patent Publication No. US-2009-0242399-A1; U.S. Patent Publication No. US-2009-0242425-A1; U.S. Patent Publication No. US-2007-0016381-A1; U.S. Patent Publication No. US-2008-0033254-A1; U.S. Patent Publication No. US-2009-0192380-A1; U.S. Patent Publication No. US-2007-0213611-A1; U.S. Patent Publication No. US-2008-0083617-A1; U.S. Patent Publication No. US-2009-0076356-A1; U.S. Patent Publication No. US-2007-0163880-A1; U.S. Patent Publication No. US-2007-0027370-A1; U.S. Patent Publication No. US-2007-0203966-A1; U.S. Patent Publication No. US-2007-0208245-A1; U.S. Patent Publication No. US-2007-0208246-A1; U.S. Patent Publication No. US-2007-0208244-A1; U.S. Patent Publication No. US-2007-0173708 A9; U.S. Patent Publication No. US-2009-0018424-A1; U.S. Patent Publication No. US-2008-0197024-A1; U.S. Patent Publication No. US-2008-0200788-A1; U.S. Patent Publication No. US-2008-0200789-A1; U.S. Patent Publication No. US-2008-0200791-A1; U.S. Patent Publication No. US-2009-0178459-A1; U.S. Patent Publication No. US-2009-0131769-A1; U.S. Patent Publication No. US-2009-0131768-A1; U.S. Patent Publication No. US-2009-0131777-A1; U.S. Patent Publication No. US-2009-0137887-A1; U.S. Patent Publication No. US-2009-0131776-A1; U.S. Patent Publication No. US-2009-0124964-A1; U.S. Patent Publication No. US-2009-0137886-A1; U.S. Patent Publication No. US-2007-0032718-A1; U.S. Patent Publication No. US-2005-0033132-A1; U.S. Patent Publication No. US-2008-0228054-A1; and U.S. Patent Publication No. US-2008-0228051-A1.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Terms and phrases used in this document, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps; the term 'example' is used to provide exemplary instances of the item in discussion, not an exhaustive or limiting list thereof; and adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A device for in vivo measurement of a glucose concentration, the device comprising:
   a transcutaneous sensor configured to measure a signal indicative of a glucose concentration in a host, wherein the sensor comprises an electroactive surface; and
   a membrane located over the sensor, wherein the membrane comprises:
   a second domain comprising a polymer comprising a plurality of repeating hard segments and repeating soft segments, wherein a soft segment of the plurality of repeating soft segments has a molecular weight from about 200 Daltons to about 50,000 Daltons, wherein a hard segment of the plurality of repeating hard segments has a molecular weight from about 160 Daltons to about 10,000 Daltons, wherein the polymer comprises a hydrophilic segment, wherein the second domain comprises both hydrophilic and hydrophobic regions, whereby diffusion of glucose and oxygen through the second domain is controlled; and
   sensor electronics operably connected to the sensor, wherein the sensor electronics are configured to measure a current flow produced by the sensor to generate sensor data indicative of glucose concentration.

2. The device of claim 1, wherein the polymer is a polyurethaneurea.

3. The device of claim 1, wherein the hydrophilic segment comprises acrylate.

4. The device of claim 1, wherein the membrane comprises a third domain configured to reduce permeation therethrough of an interfering species.

5. The device of claim 4, further comprising a first domain comprising an enzyme configured to react with glucose to produce a measured species, wherein the third domain is located between the sensor and the first domain.

6. The device of claim 4, wherein the third domain comprises a polymer comprising ionic components.

7. The device of claim 4, wherein the third domain is configured to limit diffusion of interfering species with a molecular weight greater than a molecular weight of hydrogen peroxide.

8. The device of claim 1, wherein the polymer is polyurethaneurea, wherein the hydrophilic segment comprises acrylate.

9. The device of claim 1, wherein the polymer is polyurethaneurea, wherein the hydrophilic segment comprises acrylate, wherein the membrane comprises a third domain configured to reduce permeation therethrough of an interfering species.

10. The device of claim 1, further comprising a first domain comprising an enzyme configured to react with glucose to produce a measured species, wherein the polymer is polyurethaneurea, wherein the hydrophilic segment comprises acrylate, wherein the membrane comprises a third domain configured to reduce permeation therethrough of an interfering species, wherein the third domain is located between the sensor and the first domain.

11. The device of claim 1, wherein the hydrophilic segment is selected from the group consisting of: polyvinyl acetate, poly(ethylene glycol), polyacrylamide, acetates, polyethylene oxide, polyvinylpyrrolidone, and poly ethyl acrylate.

12. The device of claim 1, wherein the polyurethane polymer comprises silicone.

13. The device of claim 12, wherein the polymer comprises from about 10% to about 50% silicone by weight.

14. The device of claim 13, wherein the polymer comprises from about 20% to about 40% silicone by weight.

15. The device of claim 1, wherein the polymer is polyurethaneurea, wherein the hydrophilic segment comprises acrylate, wherein the polyurethane polymer comprises silicone.

16. The device of claim 1, wherein the polymer comprising the hydrophilic segment comprises from about 5% to about 50% by weight of the blend.

17. The device of claim 1, wherein the polyurethane polymer is polyurethaneurea, wherein the hydrophilic segment comprises acrylate, wherein the polymer comprising the hydrophilic segment comprises from about 5% to about 50% by weight of the blend.

18. The device of claim 1, wherein the device is configured to have a sensor session from 5 to 10 days.

19. The device of claim 1, wherein the sensor is configured to continuously measure a signal indicative of a glucose concentration in a host.

* * * * *

UNITED STATES PATENT AND TRADEMARK OFFICE
CERTIFICATE OF CORRECTION

PATENT NO. : 9,693,721 B2
APPLICATION NO. : 14/742137
DATED : July 4, 2017
INVENTOR(S) : Robert J. Boock It is certified that error appears in the above-identified patent and that said Letters Patent is hereby corrected as shown below:

On the Title Page

In Column 2 (page 7, item (56)) at Line 25, Under Other Publications, change "hypoglycaemic" to --hypoglycemic--.

In Column 2 (page 7, item (56)) at Line 51, Under Other Publications, change "Senso" to --Sensor--.

In Column 1 (page 8, item (56)) at Line 38, Under Other Publications, change "glusose" to --glucose--.

In Column 1 (page 8, item (56)) at Line 64, Under Other Publications, change "reliablity" to --reliability--.

In Column 2 (page 8, item (56)) at Line 10, Under Other Publications, change "Enzymlology" to --Enzymology--.

In Column 2 (page 8, item (56)) at Line 39, Under Other Publications, change "DuPont" to --DuPont[1]--.

In Column 2 (page 8, item (56)) at Line 45, Under Other Publications, change "your and your" to --you and your--.

In Column 2 (page 8, item (56)) at Line 48, Under Other Publications, change "H202." to --H2O2.--.

In Column 2 (page 8, item (56)) at Line 70, Under Other Publications, change "Therapeuticsr" to --Therapeutics--.

In Column 1 (page 9, item (56)) at Line 9, Under Other Publications, change "Hypoglycaemia" to --Hypoglycemia--.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*

In Column 1 (page 9, item (56)) at Line 33, Under Other Publications, change "Type I" to --Type 1--.

In Column 1 (page 10, item (56)) at Line 7, Under Other Publications, change "biotelemeter" to --biotelemetry--.

In Column 1 (page 10, item (56)) at Line 65, Under Other Publications, change "activitiy" to --activity--.

In Column 2 (page 10, item (56)) at Line 30, Under Other Publications, change "iunsulin interaaction in tyhpe" to --insulin interaction in type--.

In Column 2 (page 10, item (56)) at Line 48, Under Other Publications, change "Electronanalysis" to --Electroanalysis--.

In Column 1 (page 11, item (56)) at Line 38, Under Other Publications, change "middionline" to --mddionline--.

In Column 2 (page 11, item (56)) at Line 6, Under Other Publications, change "termistor" to --thermistor--.

In Column 1 (page 12, item (56)) at Line 3, Under Other Publications, change "Bromedical" to --Biomedical--.

In Column 1 (page 12, item (56)) at Line 45, Under Other Publications, change "peroxice" to --peroxide--.

In Column 1 (page 13, item (56)) at Line 12, Under Other Publications, change "Diabetic" to --Diabetes--.

In Column 1 (page 13, item (56)) at Line 30, Under Other Publications, change "of" to --for--.

In Column 2 (page 14, item (56)) at Line 30, Under Other Publications, change "H202" to --H2O2--.

In Column 2 (page 14, item (56)) at Line 32, Under Other Publications, change "H202" to --H2O2--.

In Column 2 (page 14, item (56)) at Line 38, Under Other Publications, change "H202" to --H2O2--.

In the Specification

In Column 5 at Line 52, Change "andrenostenedione;" to --androstenedione;--.

In Column 6 at Line 1, Change "diptheria/" to --diphtheria/--.

In Column 6 at Line 8, Change "perioxidase;" to --peroxidase;--.

In Column 6 at Line 17, Change "sissomicin;" to --sisomicin;--.

CERTIFICATE OF CORRECTION (continued)
U.S. Pat. No. 9,693,721 B2

In Column 6 at Line 21, Change "duodenalisa," to --duodenalis,--.

In Column 6 at Line 29, Change "Trepenoma pallidium," to --Treponema pallidum,--.

In Column 6 at Line 30, Change "stomatis" to --stomatitis--.

In Column 6 at Line 52, Change "(barbituates," to --(barbiturates,--.

In Column 6 at Line 67, Change "(FHIAA)." to --(5-HIAA).--.

In Column 7 at Line 7, Change "and or" to --and/or--.

In Column 12 at Line 16, Change "Bellafonte," to --Bellefonte,--.

In Column 29 at Line 35, Change "gluteraldehyde" to --glutaraldehyde--.

In Column 36 at Line 1, Change "aliphate" to --aliphatic--.

In Column 38 at Line 42 (approx.), Change "bisiguanides" to --bisbiguanides--.

In Column 38 at Line 43 (approx.), Change "iodophores" to --iodophors--.

In Column 39 at Line 11, Change "acetometaphen," to --acetaminophen,--.

In Column 39 at Line 17, Change "melenamic" to --mefenamic--.

In Column 39 at Line 21, Change "betamethesone," to --betamethasone,--.

In Column 39 at Line 36, Change "infiximab)," to --infliximab),--.

In Column 39 at Line 39, Change "methothrexate," to --methotrexate,--.

In Column 39 at Line 40, Change "vincristing, mitomycine," to --vincristine, mitomycin,--.

In Column 39 at Line 42, Change "batimstat," to --batimastat,--.

In Column 39 at Line 47, Change "Tesosentan," to --Tezosentan,--.

In Column 39 at Line 47, Change "Cerivasttin)," to --Cerivastatin),--.

In Column 39 at Line 57, Change "aminoclycosides," to --aminoglycosides,--.

In Column 41 at Line 3, Change "glenipin," to --genipin,--.

In Column 43 at Line 10, Change "'sustained" to "'sustained'".

CERTIFICATE OF CORRECTION (continued)
U.S. Pat. No. 9,693,721 B2

In Column 44 at Line 50, Change "does" to --doses--.

In Column 48 at Line 58, Change "mataproterenol," to --metaproterenol,--.

In Column 50 at Line 38, Change "U.S. No." to --U.S. Patent Publication No.--.

In Column 50 at Line 52 (approx.), Change "U.S. Publication No.--." to --U.S. Patent Publication No.--.

In Column 52 at Line 44, Change "0173708 A9;" to --0173708-A9;--.

In the Claims

In Column 54 at Line 58, In Claim 12, after "wherein the" delete "polyurethane".

In Column 54 at Line 66, In Claim 15, after "wherein the" delete "polyurethane".

In Column 55 at Line 4, In Claim 17, after "wherein the" delete "polyurethane".